(12) United States Patent
Maras et al.

(10) Patent No.: US 9,278,972 B2
(45) Date of Patent: Mar. 8, 2016

(54) SYNTHESIS OF TRIAZOLOPYRIMIDINE COMPOUNDS

(71) Applicant: Lek Pharmaceuticals d.d., Ljubljana (SI)

(72) Inventors: Nenad Maras, Ljubljana (SI); Ivana Gazic Smilovic, Ljubljana (SI); Damjan Sterk, Ljubljana (SI)

(73) Assignee: Lek Pharmaceuticals d.d. (SI)

( * ) Notice: Subject to any disclaimer, the term of this patent is extended or adjusted under 35 U.S.C. 154(b) by 0 days.

(21) Appl. No.: 14/366,764

(22) PCT Filed: Dec. 20, 2012

(86) PCT No.: PCT/EP2012/076458
§ 371 (c)(1),
(2) Date: Jun. 19, 2014

(87) PCT Pub. No.: WO2013/092900
PCT Pub. Date: Jun. 27, 2013

(65) Prior Publication Data
US 2014/0371449 A1 Dec. 18, 2014

(30) Foreign Application Priority Data

Dec. 23, 2011 (EP) .................................... 11195508
May 24, 2012 (EP) .................................... 12169185

(51) Int. Cl.
| | | |
|---|---|---|
| C07D 487/00 | (2006.01) | |
| C07D 487/04 | (2006.01) | |
| C07C 271/24 | (2006.01) | |
| C07D 239/48 | (2006.01) | |
| C07D 317/44 | (2006.01) | |

(52) U.S. Cl.
CPC ............ *C07D 487/04* (2013.01); *C07C 271/24* (2013.01); *C07D 239/48* (2013.01); *C07D 317/44* (2013.01); *C07B 2200/07* (2013.01); *C07C 2101/08* (2013.01); *C07C 2101/10* (2013.01)

(58) Field of Classification Search
None
See application file for complete search history.

(56) References Cited

U.S. PATENT DOCUMENTS 9,056,838 B2 * 6/2015 Kansal et al.

FOREIGN PATENT DOCUMENTS

| WO | 00-34283 A1 | 6/2000 |
| WO | 2010-030224 A1 | 3/2010 |
| WO | 2011-017108 A2 | 2/2011 |
| WO | 2012-139455 A1 | 10/2012 |

OTHER PUBLICATIONS

Francis A. Carey, Richard J. Sundberg; Advanced Organic Chemistry: Part B: Reaction and Synthesis (2007) pp. 267-272.*
http://www.organic-chemistry.org/synthesis/N1H/reductionsnitrocompounds.shtm (last accessed Jun. 22, 2015).*
Francis A. Carey, Richard J. Sundberg; Advanced Organic Chemistry: Part B: Reaction and Synthesis (2007) pp. 390-395.*
Springthorpe, "From ATP to AZD6140: The discovery of an orally active reversible P2Y12 receptor antagonist for the prevention of thrombosis," Science Direct, Bioorganic & Medicinal Chemistry Letters 17 (2007) 6013-6018.
Hong Ye, et al, "Carba-nucleosides as Potent Antagonists of the Adenosine 5'-Diphosphate (ADP) Purinergic Receptor (P2Y12) on Human Platelets", CHEMMEDCHEM, vol. 3, No. 5, May 19, 2008, pp. 732-736.

* cited by examiner

*Primary Examiner* — Jeffrey H Murray
(74) *Attorney, Agent, or Firm* — Luedeka Neely Group, P.C.

(57) ABSTRACT

The present invention relates to the field of organic synthesis and describes the synthesis of specific intermediates suitable for the preparation of triazolopyrimidine compounds such as ticagrelor.

7 Claims, No Drawings

SYNTHESIS OF TRIAZOLOPYRIMIDINE COMPOUNDS

This application is a national phase entry of PCT International application number PCT/EP2012/076458, filed Dec. 20, 2012. This application also claims the benefit of the earlier filing dates of: (1) EP11195508.2, filed Dec. 23, 2011; and (2) EP12169185.1, filed May 24, 2012.

The present invention relates to the field of organic synthesis, in particular to the synthesis of specific triazolopyrimidine compounds and intermediates thereof as well as related derivatives.

An important triazolopyrimidine compound is ticagrelor (TCG; Brilinta®; 3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1S,2S,3R,5S)-1,2-cyclopentanediol) having the following structural formula.

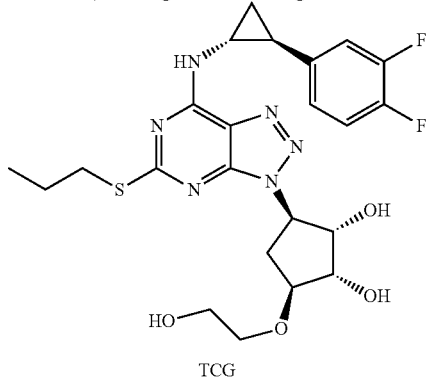 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

TCG

Ticagrelor shows pharmaceutical activity by functioning as a P2Y12 receptor antagonist and thus is indicated for the treatment or prevention of thrombotic events, for example stroke, heart attack, acute coronary syndrome or myocardial infection with ST elevation, other coronary artery diseases and arterial thrombosis as well as other disorders related to platelet aggregation (WO 00/34283).

The synthesis of ticagrelor (TCG) is demanding. There are five to six known synthetic variants, which are described in the basic patent application WO 00/34283, an improved one in patent application WO 01/92263, and a further improved one in patent application WO 10/030224 respectively derived from the originator AstraZeneca, while two are published in a "deutero" patent application WO 11/017108 of Auspex Pharmaceuticals. Further, there is one synthetic path published in a scientific journal (*Bioorg. Med. Chem. Lett.* 2007, 17, 6013-6018).

The first synthesis of TCG as described in WO 00/34283 is depicted in scheme 1 below.

Scheme 1: Synthesis of ticagrelor (TCG) as described in WO 00/34283

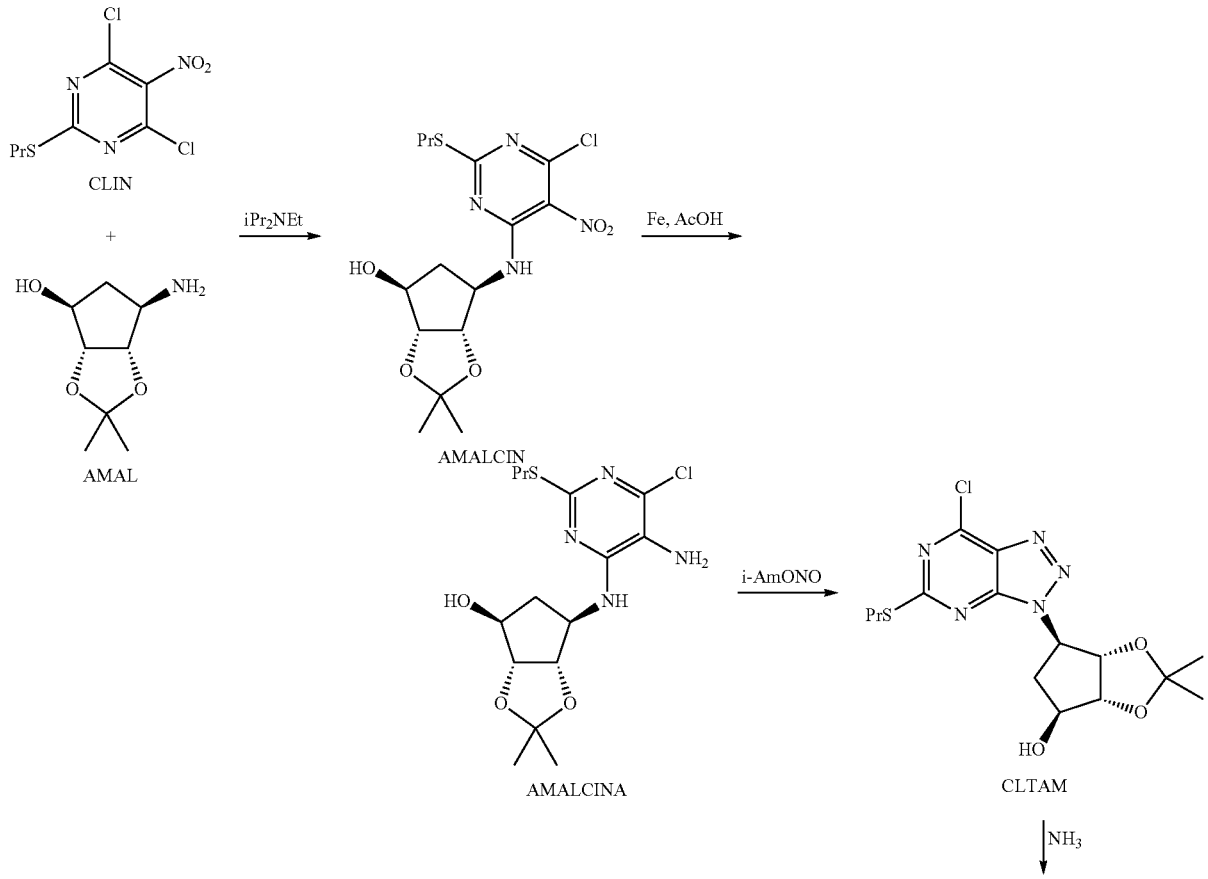

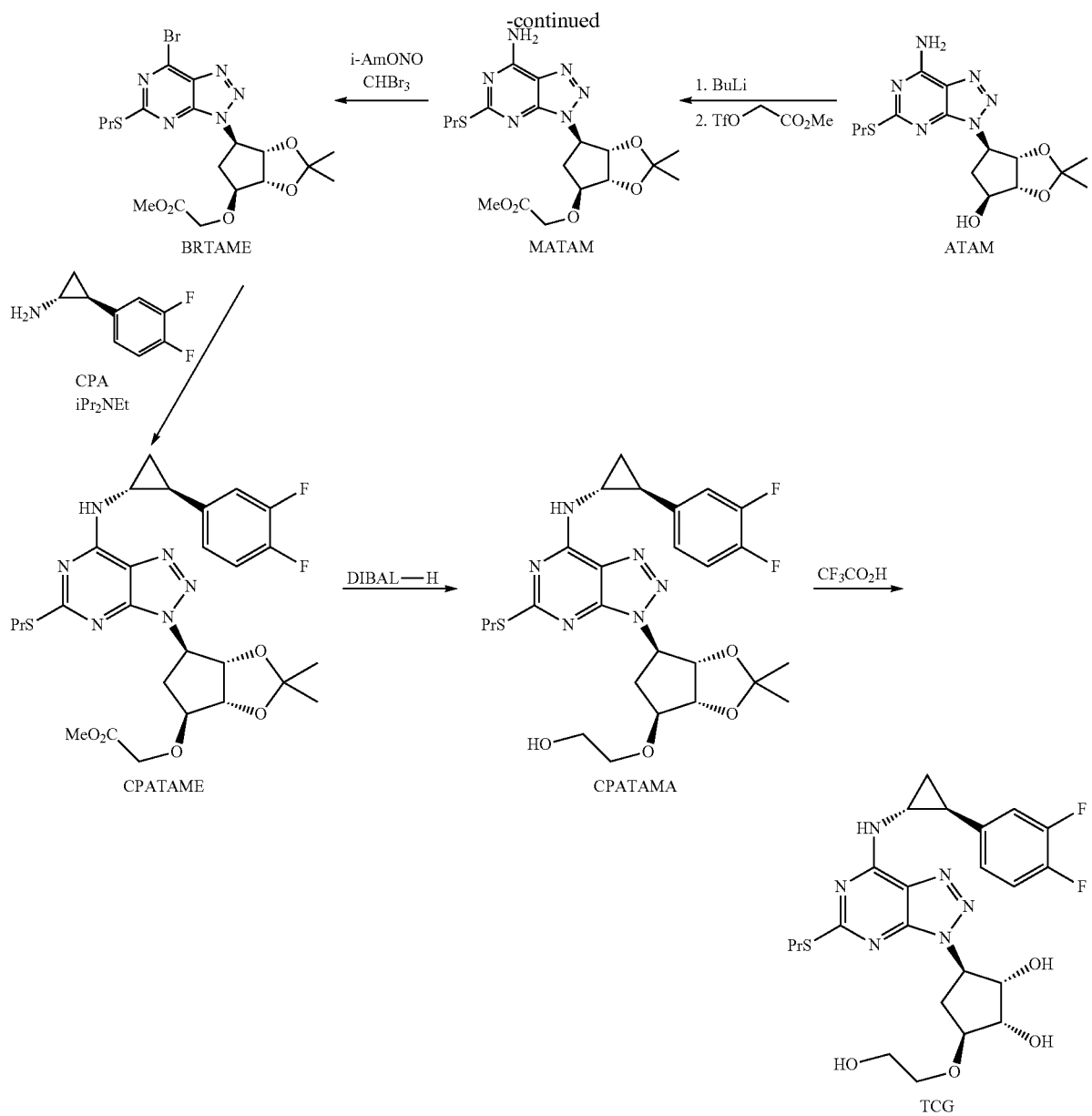

This nine step synthesis of ticagrelor (TCG) as described in WO 00/34283 (Scheme 1) starts with a reaction between CLIN and AMAL. In the presence of diisopropylethylamine (iPr₂Net) AMALCIN is formed, which is in then reduced with iron (Fe) in acetic acid to AMALCINA. In the next step CLTAM is formed using isopentyl nitrite (iAmONO). Next, ATAM was prepared using ammonia, and side chain was introduced (MATAM) using n-butyllithium and methyl 2-(((trifluoromethyl)sulfonyl)oxy)acetate, which was previously prepared by reaction between methyl glycolate and triflic anhydride. In next step BRTAME is formed using iAmONO and CHBr₃, followed by the nucleophilic aromatic substitution of Br with CPA in the presence of iPr₂NEt to form CPATAME. This is then reduced to CPATAMA using DIBAL-H. Deprotection of diol group in the presence of trifluoroacetic acid in the final step leads to TCG.

This synthetic path is very long (9 steps, not including reagents preparation) and uses toxic compounds like CHBr₃, triflic anhydride, and methyl 2-(((trifluoromethyl)sulfonyl) oxy)acetate. The introduction of the methoxycarbonylmethyl group (reaction from ATAM to MATAM) is very difficult due to poor chemoselectivity, as the amino group also reacts with 2-(((trifluoromethyl)sulfonyl)oxy)acetate.

An improved synthesis of ticagrelor (TCG) is described in WO 01/92263 (see Scheme 2). In this process the hydroxyethyl side chain is introduced at the beginning of the synthesis by a three step reaction path from AMAL to AMALA, which is then reacted with CLINA (prepared from CLIDA) in presence of triethylamine (Et₃N) to form AMALCINAA. The triazole ring of CLTAM is formed with NaNO₂ in acetic acid, and then Cl is exchanged with CPA to form CPATAMA. In the final step TCG is prepared via deprotection using HCl.

This improved process still has substantial length (7-8 steps). In AMALA synthesis the benzyloxycarbonyl protection (Cbz) is used, which is then removed in the third step using hydrogenation with Pd/C as a catalyst. Hydrogenation with Pt/C as a catalyst is also used in the reduction of CLIDA to CLINA.

Scheme 2: Synthesis of ticagrelor (TCG) as described in WO 01/92263.

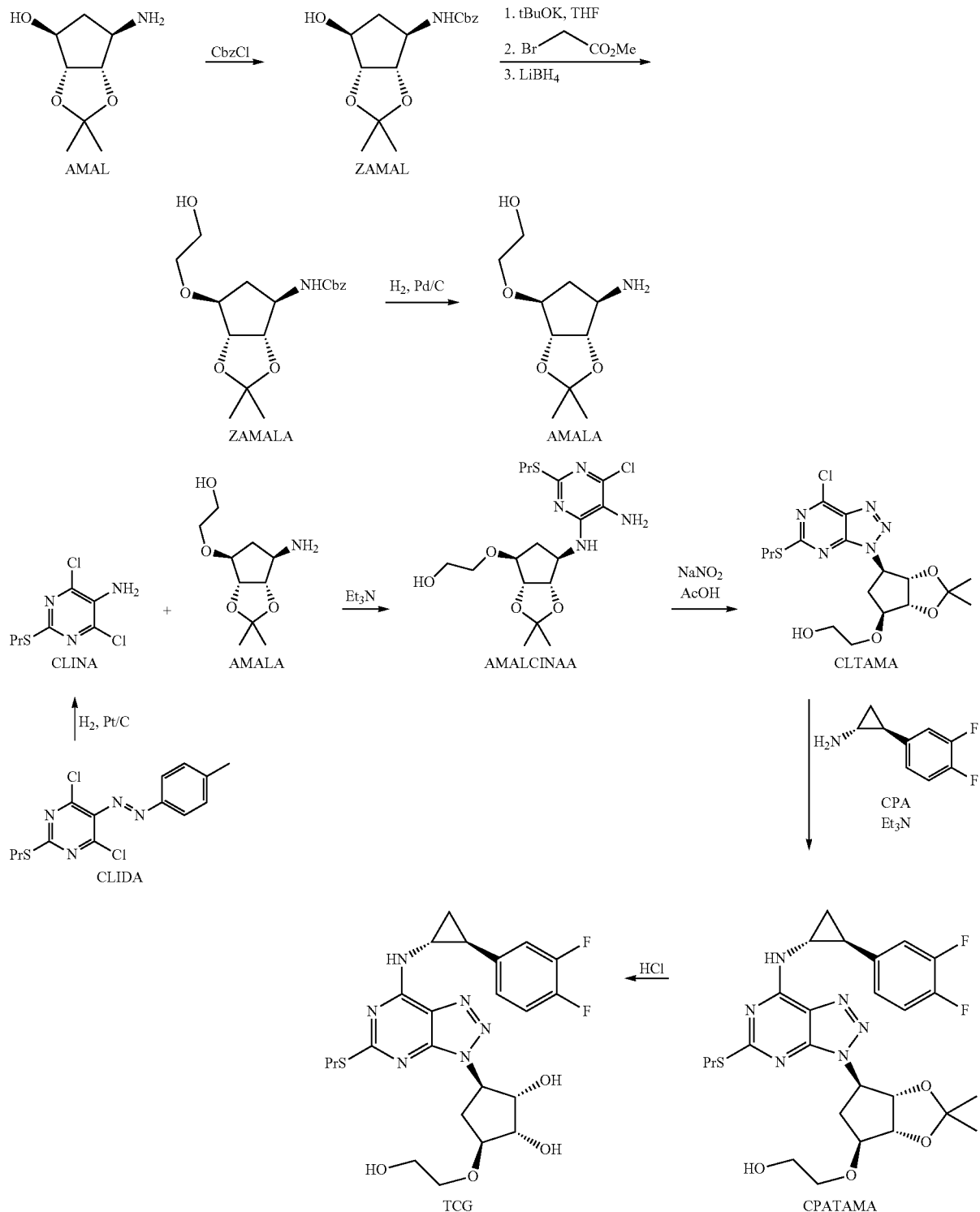

Another improved synthetic path is described in WO 10/030224 (Scheme 3). The key steps in this process are reduction of CLIN to CLINA or AMALCINO to AMALCINAA using hydrogen gas and platinum vanadium catalyst. The introduction of the hydroxyethyl side chain to AMAL to form AMALA, cyclization, substitution of Cl atom of CLTAMA with CPA and final acidic deprotection are the same as in WO 01/92263.

This further improved process to TCG has 8 reaction steps. Like in WO 01/92263, there are used the Cbz protecting group and heavy metals as catalysts like Pd, Pt and/or V.

Scheme 3: Synthesis of ticagrelor (TCG) as described in WO 10/030224.
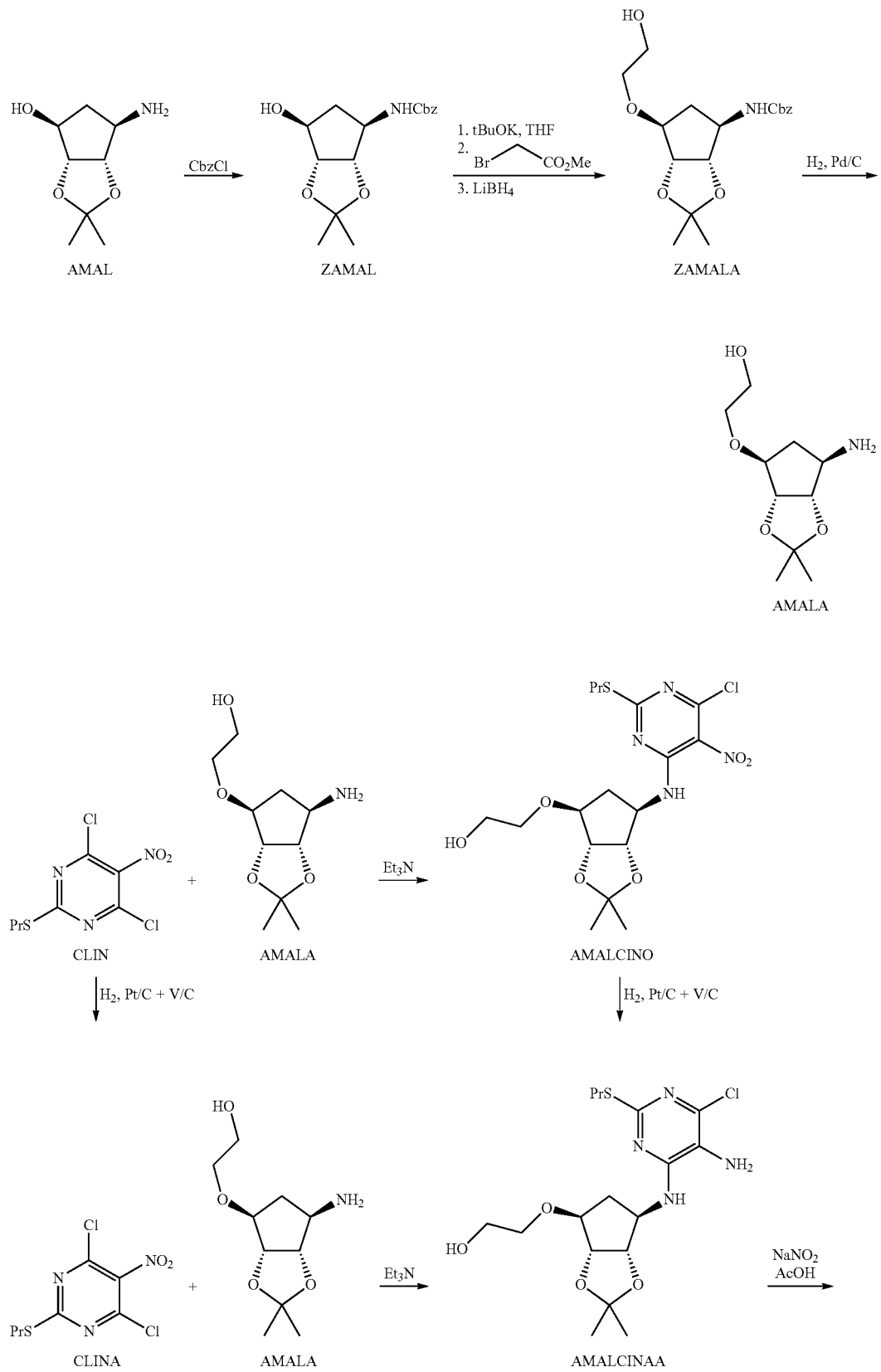

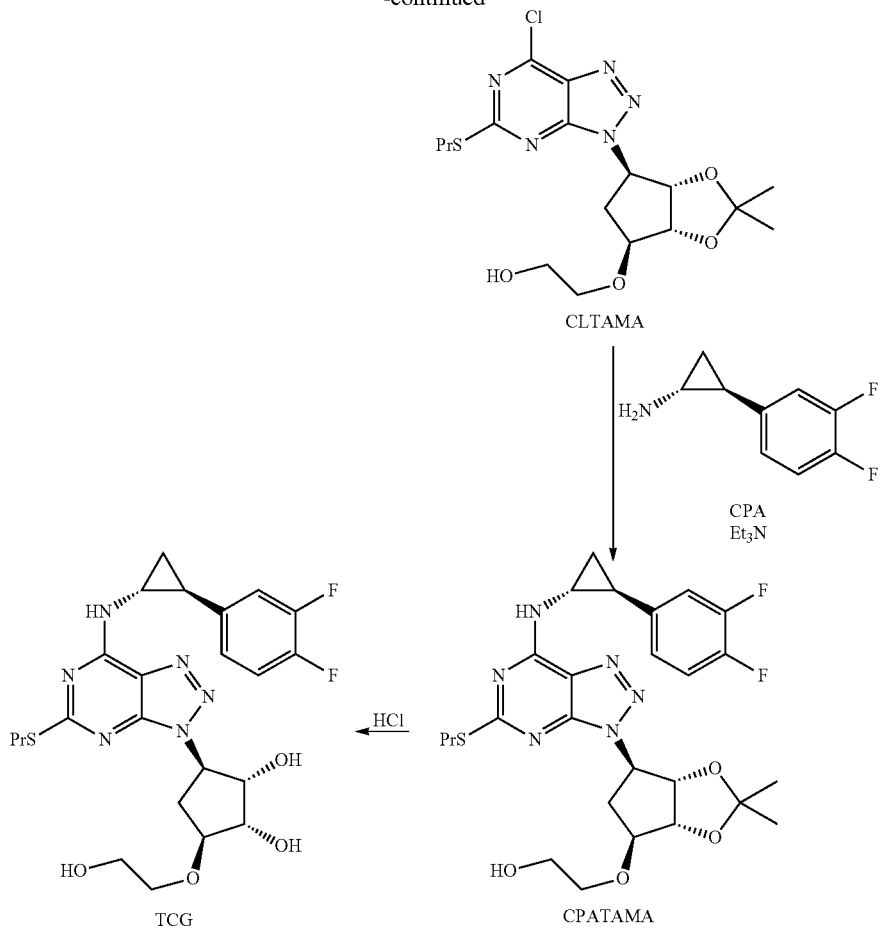
AstraZeneca published a synthetic path (Scheme 4) to ticagrelor (TCG) in *Bioorg. Med. Chem. Lett.* 2007, 17, 6013-6018. Intermediates in this process are similar to those described in WO 01/92263. There is difference in formation of triazolo ring of CLTAMA where iAmONO is used, and difference in deprotection in the last step.
Scheme 4: Synthesis of ticagrelor (TCG) as described in Bioorg. Med. Chem. Lett. 2007, 17, 6013-6018.
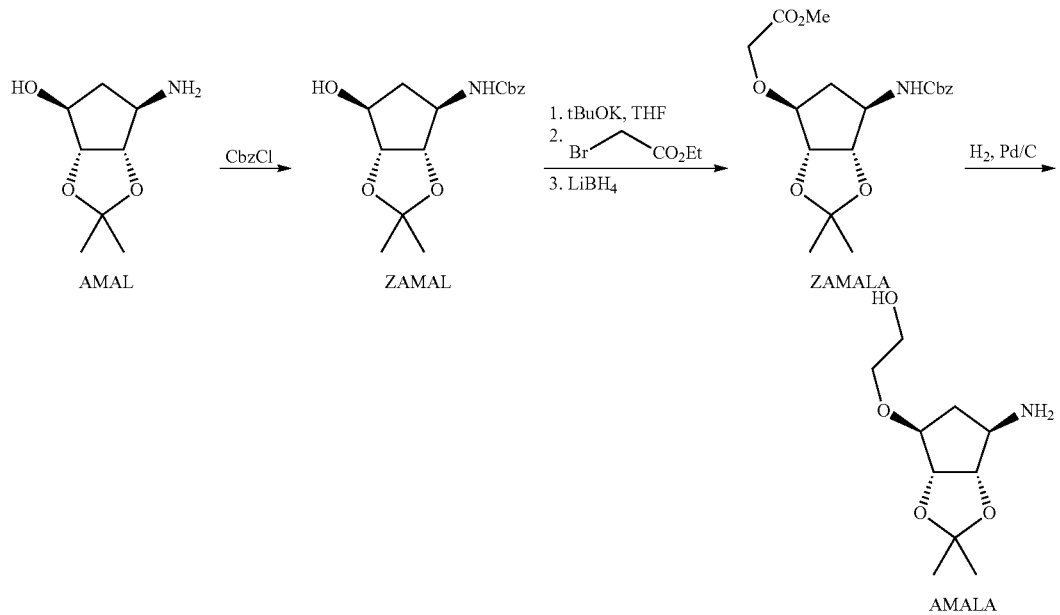

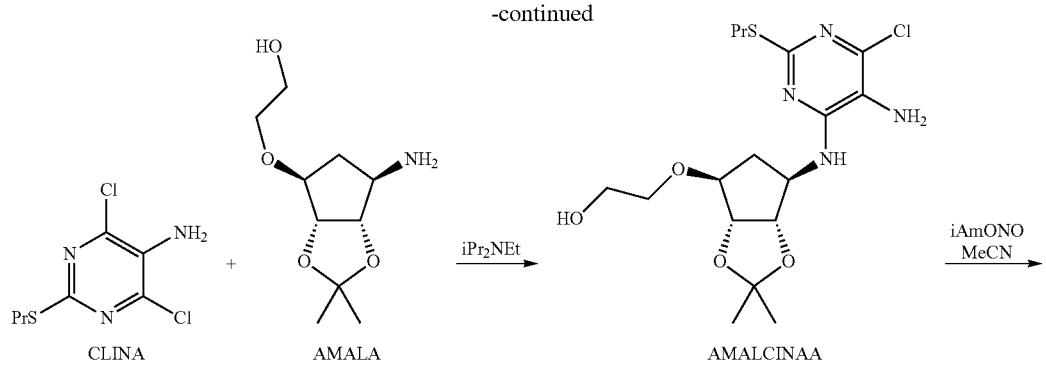

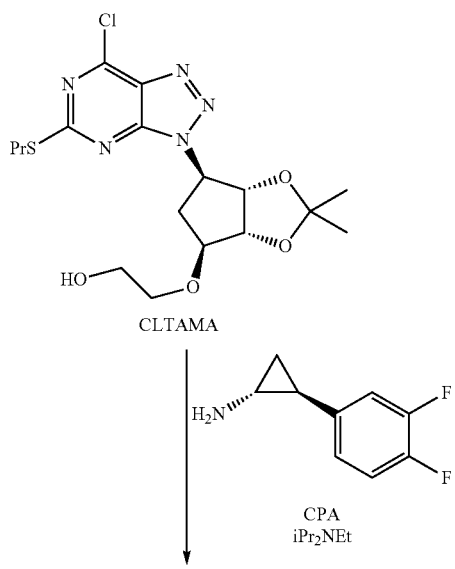

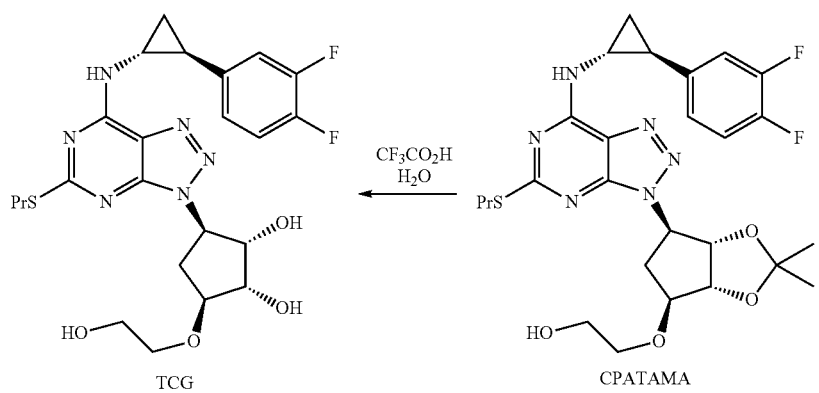

Another synthetic variant (Scheme 5) to ticagrelor (TCG) is described in WO 11/017108 by Auspex Pharmaceuticals. In nine step synthesis they prepared AMALE through deprotection of ZAMALE using hydrogen gas and Pd/C, which was then reduced to AMALA with LiAlH₄. AMALCINO was prepared without presence of base, further steps are similar to those published in WO 01/92263.

Still another synthetic variant (Scheme 6) to obtain ticagrelor with deuterated hydroxyethyl group (TCGD) is also described in WO 11/017108 by Auspex Pharmaceuticals.

Scheme 5: Synthesis of ticagrelor (TCG) as described in "deutero" patent WO 11/017108.
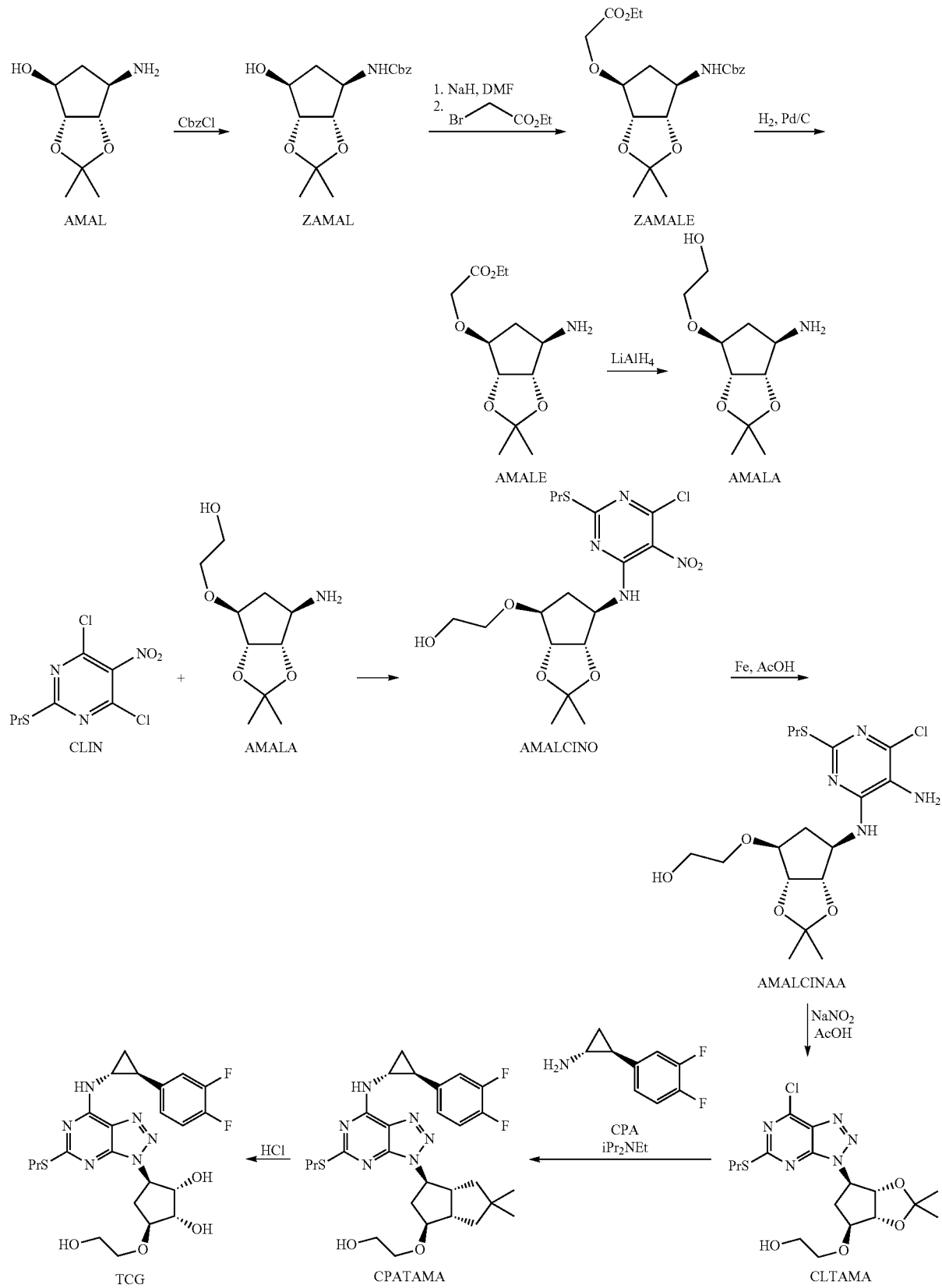

Scheme 6: Synthesis of ticagrelor with deuterated hydroxyethyl group (TCGD) as described in "deutero" patent WO 11/017108.
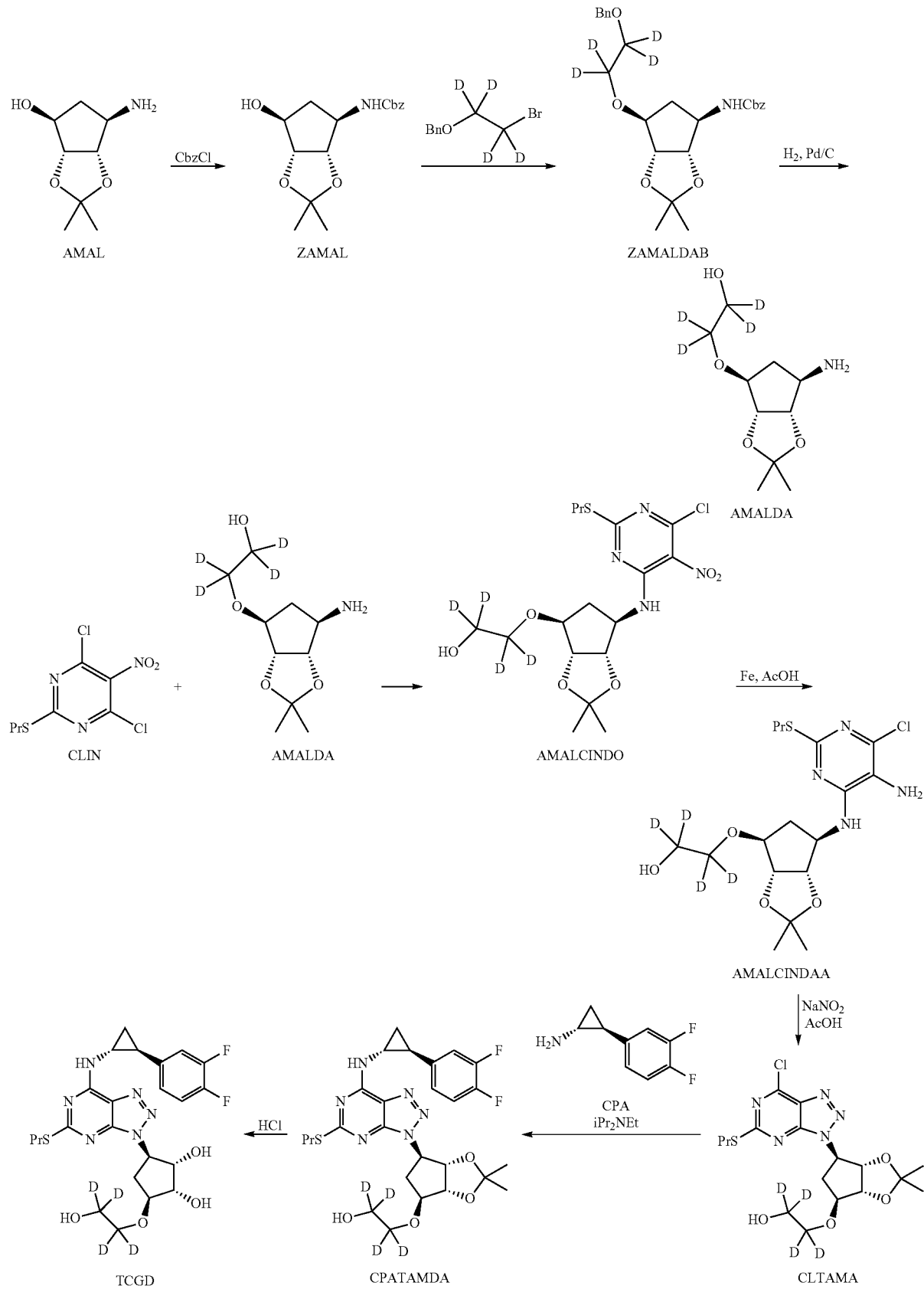

As becomes apparent from the above, a major drawback of the hitherto known synthesis schemes for the preparation of ticagrelor is that the synthesis is long.

SUMMARY OF THE INVENTION

The object of the present invention was to provide an industrially applicable and economically improved process for obtaining ticagrelor.

The present invention provides a process for the preparation of a compound of formula XI (Ticagrelor) or pharmaceutically acceptable salt thereof

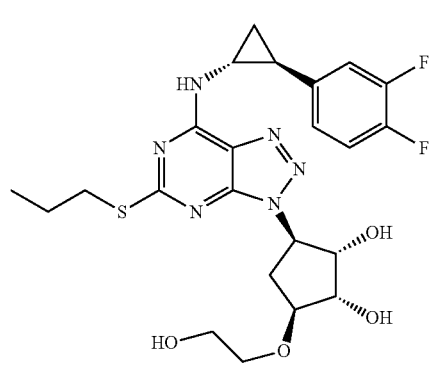

XI comprising the steps of:
(i) contacting a compound of formula VI or a salt thereof

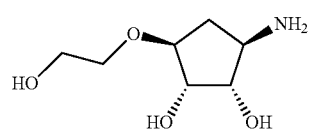

VI with a compound of formula VII or VII'

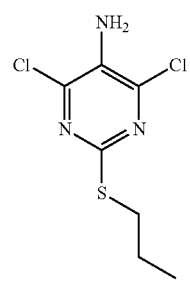

VII

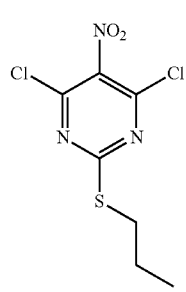

VII' to obtain a compound of formula VIII or VIII', respectively

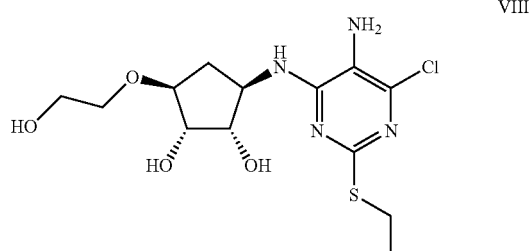

VIII

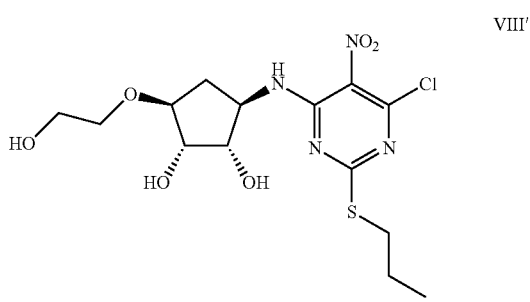

VIII'

(ii) optionally, if a compound of formula VIII' is obtained, reducing the compound of formula VIII' to a compound of formula VIII, (iii) converting a compound of formula VIII by nitrosation to a compound of formula IX or a compound of formula IX'

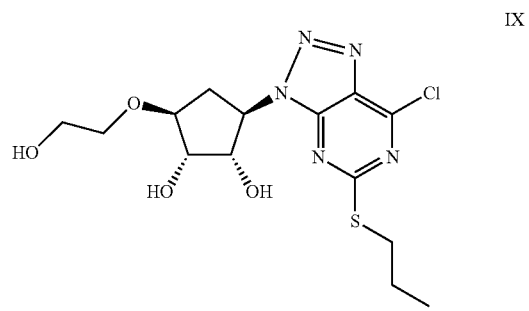

IX

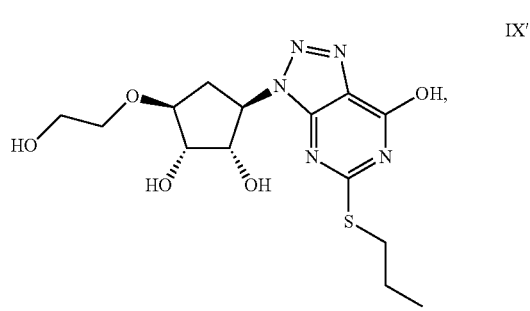

IX' and (iv) coupling the compound of formula IX or IX' with a compound of formula X

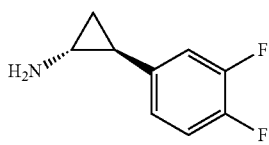

or a salt thereof in a presence of a base to provide a compound of formula XI or a pharmaceutically acceptable salt thereof.

The process defined above allows for preparation or synthesis of ticagrelor with an industrially applicable and economically improved process. Preferred embodiments will be described below. The present invention further provides novel compounds that are highly useful as key intermediates in the preparation or synthesis of ticagrelor.

According to a further aspect, the present invention provides novel and useful process alternatives (i), (ii) and (iii) to prepare a compound of formula VI or a salt thereof,

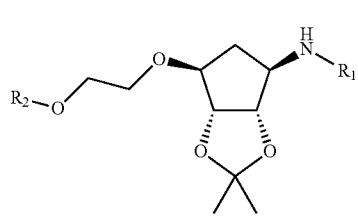

which process alternatives (i), (ii) and (iii) respectively comprises the steps of:

(i) either:

(0-1) providing a compound of formula III or a salt thereof

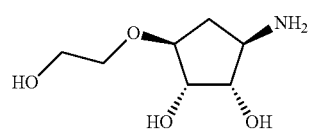

wherein $R_1$ is tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, preferably tert-butyl (t-Bu), or mono, di- or triphenyl substituted methyl, preferably benzyl (Bn), and $R_2$ is benzyl (Bn), tert-butyl (t-Bu), tert-butyldimethylsilyl (TBDMS), methoxymethyl (MOM), trityl (Tr), acetyl (Ac) or benzoyl (Bz);

(0-2) directly converting a compound of formula III to a compound of formula VI, and (0-3) optionally converting a compound of formula VI to a salt thereof;

(ii) or:

(0-1') providing a compound of formula III or a salt thereof

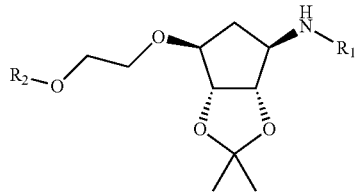

wherein $R_1$ and $R_2$ is as defined above, (0-2') converting a compound of formula III to a compound of formula IV

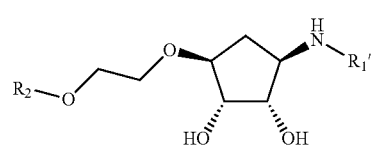

wherein $R_1$' is hydrogen, Boc, Cbz, TFA, Tr, TCA, CHO, Ac, Bz, Fmoc, $C_4$-$C_5$-tert-alkyl, preferably t-Bu, or mono, di- or triphenyl substituted methyl, preferably Bn, and $R_2$ is as defined above, and (0-3') converting a compound of formula IV to a compound of formula VI, (0-4') optionally converting a compound of formula VI to a salt thereof;

(iii) or:

(0-1") providing a compound of formula III or a salt thereof

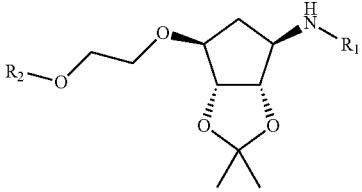

wherein $R_1$ is tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, preferably tert-butyl (t-Bu), or mono, di- or triphenyl substituted methyl, preferably benzyl (Bn), and $R_2$ is as defined above, (0-2") converting a compound of formula III to a compound of formula V

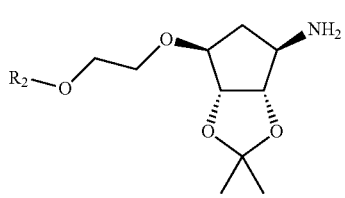

wherein $R_2$ is as defined above, and (0-3") converting a compound of formula V to a compound of formula VI, (0-4") optionally converting a compound of formula VI to a salt thereof.

For the above alternative embodiments (i), (ii) and (iii), the compound of formula III or a salt thereof may preferably be prepared by comprising the steps of:

providing a compound of formula I

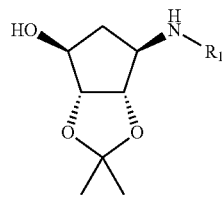

I wherein $R_1$ is Boc, Cbz, TFA, Tr, TCA, CHO, Ac, Bz, Fmoc, $C_4$-$C_5$-tert-alkyl, preferably t-Bu, or mono, di- or triphenyl substituted methyl, preferably Bn, reacting the compound of formula I with a compound of formula II

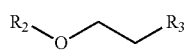

II wherein $R_2$ is Bn, t-Bu, TBDMS, MOM, Tr, Ac or Bz, and $R_3$ is TsO (tosylate), MsO (mesylate), Br or Cl to yield a compound of formula III, and optionally converting the compound of formula III to a salt thereof.

This further aspect of the invention allows a very short process for introduction of hydroxyethyl side chain to amino carbasugar (2-3 steps), while at the same time using cheap, non-toxic and basic reagents.

Moreover, introduction of hydroxyethyl side chain based on such concept allows to make beneficial use thereof in other synthesis routes to finally obtain obtaining triazolopyrimidine compounds and specifically ticagrelor, as it facilitates introduction (and optionally "pulling through" in subsequent synthetic steps) of a structural moiety "convertible to hydroxyethyl" at any time of the total synthesis desired.

Therefore, another aspect of the present invention resides in that the compound

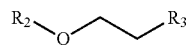

wherein $R_2$ is benzyl (Bn), tert-butyl (t-Bu), tert-butyldimethylsilyl (TBDMS), methoxymethyl (MOM), trityl (Tr), acetyl (Ac) or benzoyl (Bz) and $R_3$ is TsO, MsO, Br or Cl, is used to introduce "hydroxyethyl convertible" groups into, or to modify, intermediate compounds at desired steps of the synthesis of ticagrelor. Specifically, in such uses and process steps, a structural group denoted as "Z" and defined in the following

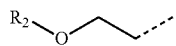

can be used and is regarded as a "group convertible to hydroxyethyl", noting that the hatched bond indicated in the aforementioned formula will be bound to the corresponding oxygen atom of the cyclopentyl ring that is present in each of the intermediate compounds of interest in the synthesis of ticagrelor, corresponding to the following general structural moiety (where the coupling to the above Z="group convertible to hydroxyethyl" is correspondingly shown by a dashed line, while other structural annexes of the respective intermediate compounds of interest are indicated by wavy lines for the ease of illustration):

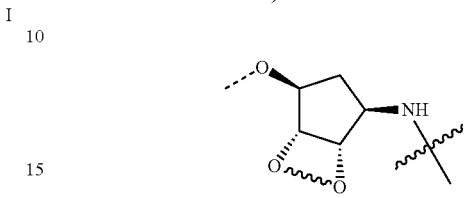

DESCRIPTION OF THE INVENTION AND OF PREFERRED EMBODIMENTS

Aspects, advantageous features and preferred embodiments of the present invention will be described in further detail below, noting however that such aspects, advantages features as well as embodiments and examples are presented for illustrative purposes only and shall not limit the invention in any way.

Use of intermediate VI as a starting reagent in the synthetic preparation of ticagrelor is a significant feature of the present invention, as it has been found that it allows for a shorter synthesis. This crucial point of using this intermediate distinguishes over intermediate AMALA used in the prior art synthesis in the fact that AMALA bears an acetonide protecting group, while the hydroxyl groups of the cyclopentane ring of the intermediate VI are not protected. As a consequence, a deprotection step otherwise required in the last step of the preparation of ticagrelor is thus omitted. The omission of said deprotection step, which is conducted in an acidic medium (aq. HCl), does not only result in shortening the synthesis for one reaction step, but also prevents formation of side products, which can be formed if the conventionally used prescribed reaction time and conditions are not followed precisely, for example products of undesired epimerizations.

Further, contrary to the prior art syntheses, the process of the current invention allows the possibility of providing solid crystalline intermediates, which is of significant advantage for enhancing purity of the product of interest. With this preferred embodiment a tedious step of additional purification, which is needed if the final intermediate is not solid (as is the case with known syntheses), can be omitted.

The above advantages are particularly important for preparation of compounds such as ticagrelor. Ticagrelor has 6 stereogenic centers (64 possible isomers), therefore the control of the stereoisomeric impurities during the synthesis is of great significance. If the intermediate entering the final step of the reaction can preferably be isolated in a solid form, the stereoisomeric impurities introduced with the starting material, or formed during the previous steps, can be substantially removed, which offers the possibility of obtaining ticagrelor of improved purity.

A further significant advantage of the present invention resides in the possibility that several steps can, if desired, be performed through one-pot conversions, without the need of isolation or separation of intermediate compounds, which one-pot system therefore constitutes a preferred embodiment of the present invention.

Accordingly, the possibility of reducing the number of required reaction steps and of simplifying reactions respectively strongly contributes to provide an improved industrially applicable and economically beneficial process for obtaining triazolopyrimidine compounds and specifically ticagrelor.

According to a preferred embodiment, the compound of formula VI or a salt thereof is prepared by comprising the steps of (0-1) providing a compound of formula III or a salt thereof

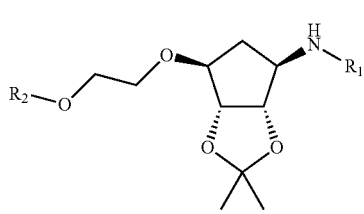

III wherein R₁ is tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, preferably tert-butyl (t-Bu), or mono, di- or triphenyl substituted methyl, preferably benzyl (Bn), and R₂ is benzyl (Bn), tert-butyl (t-Bu), tert-butyldimethylsilyl (TBDMS), methoxymethyl (MOM), trityl (Tr), acetyl (Ac) or benzoyl (Bz);

(0-2) directly converting a compound of formula III to a compound of formula VI, and (0-3) optionally converting a compound of formula VI to a salt thereof.

Alternatively, the compound of formula VI or a salt thereof can be obtained by first carrying out a deprotection reaction of the cyclopentane hydroxyl group and subsequently converting the compound of formula IV to a compound of formula VI, by comprising the steps of:

(0-1') providing a compound of formula III or a salt thereof

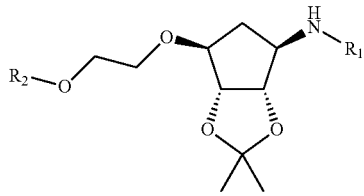

III wherein R₁ and R₂ is as defined above, (0-2') converting a compound of formula III to a compound of formula IV

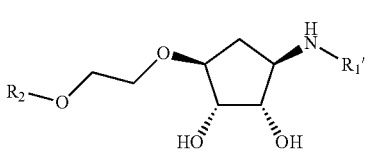

IV wherein R₁' is hydrogen, Boc, Cbz, TFA, Tr, TCA, CHO, Ac, Bz, Fmoc, $C_4$-$C_5$-tert-alkyl, preferably t-Bu, or mono, di- or triphenyl substituted methyl, preferably Bn, and R₂ is as defined above, and (0-3') converting a compound of formula IV to a compound of formula VI, (0-4') optionally converting a compound of formula VI to a salt thereof.

Alternatively, the compound of formula VI or a salt thereof can be obtained by first carrying out a deprotection reaction of the amino group and subsequently converting the compound of formula V to a compound of formula VI, by comprising the steps of:

(0-1'') providing a compound of formula III or a salt thereof

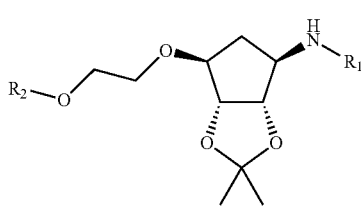

III wherein R₁ is tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, preferably tert-butyl (t-Bu), or mono, di- or triphenyl substituted methyl, preferably benzyl (Bn) and R₂ is as defined above, (0-2'') converting a compound of formula III to a compound of formula V

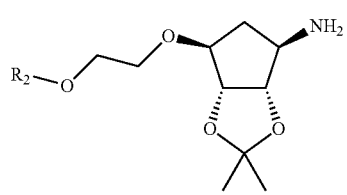

V wherein R₂ is as defined above, and (0-3'') converting a compound of formula V to a compound of formula VI, (0-4'') optionally converting a compound of formula VI to a salt thereof.

A summary of the afore-mentioned ways to prepare the compound of formula VI is shown in the following scheme 7 below.

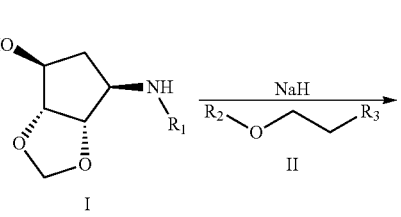

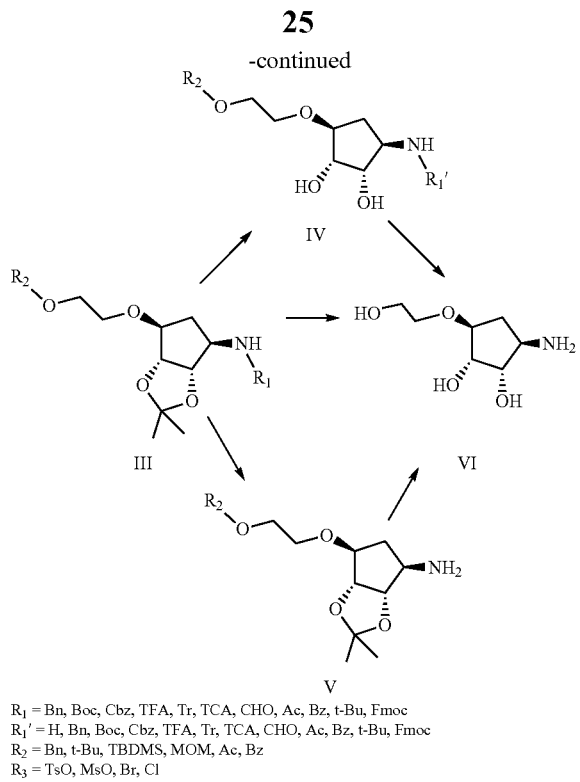

R₁ = Bn, Boc, Cbz, TFA, Tr, TCA, CHO, Ac, Bz, t-Bu, Fmoc
R₁' = H, Bn, Boc, Cbz, TFA, Tr, TCA, CHO, Ac, Bz, t-Bu, Fmoc
R₂ = Bn, t-Bu, TBDMS, MOM, Ac, Bz
R₃ = TsO, MsO, Br, Cl Scheme 7 showing process embodiments of the present invention.

Alternatively, a compound of formula VI can be prepared for example by acid hydrolysis from AMALA (Scheme 8), which can be prepared as described in WO 01/92263.

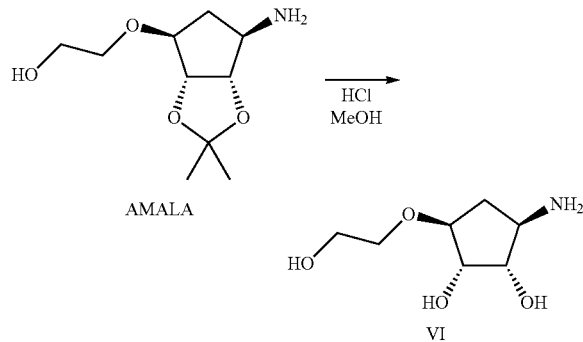

Scheme 8 showing alternative way of preparing compound of formula VI.

In another embodiment of the present invention presented in scheme 7, the compound of formula III or a salt thereof is prepared by comprising the steps of (i) providing a compound of formula I

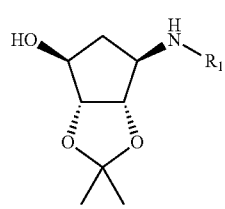

wherein $R_1$ is Boc, Cbz, TFA, Tr, TCA, CHO, Ac, Bz, Fmoc, $C_4$-$C_5$-tert-alkyl, preferably t-Bu, or mono, di- or triphenyl substituted methyl, preferably Bn, (ii) reacting the compound of formula I with a compound of formula II

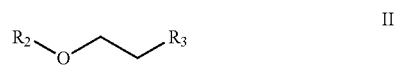

wherein $R_2$ is Bn, t-Bu, TBDMS, MOM, Tr, Ac or Bz, and $R_3$ is tosylate (TsO), mesylate (MsO), Br or Cl to yield a compound of formula III, and (iii) optionally converting the compound of formula III to a salt thereof.

Such a preferred preparation of compound III is advantageous, when the protection of amino group is introduced during the cyclopentane ring construction. Thus, according to J. Chem. Soc. Perkin Trans. 1, 1994, 613, the compound Ia ($R_1$=Bn) is a direct product of the synthesis from D-ribose and no subsequent protection is needed.

The substituent $R_1$ as mentioned above can be any suitable amino protecting group known to a skilled person, for example such a group can be selected from the group consisting of tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, for example tert-butyl (t-Bu), or mono, di- or triphenyl substituted methyl, for example benzyl (Bn). Preferred $C_4$-$C_5$-tert-alkyl is tert-butyl (t-Bu). Preferred mono, di- or triphenyl substituted methyl is benzyl (Bn).

The substituent $R_2$ as mentioned above can be any suitable hydroxyl protecting group known to a skilled person, for example such a group can be selected from the group consisting of benzyl (Bn), tert-butyl (t-Bu), tert-butyldimethylsilyl (TBDMS), methoxymethyl (MOM), trityl (Tr), acetyl (Ac) and benzoyl (Bz).

The substituent $R_3$ according to the present invention can be any suitable leaving group known to a skilled person, for example sulfonate such as tosylate (TsO) or mesylate (MsO), or halogen such as Br and Cl.

A suitable salt of intermediates III, IV, V and VI is a salt of organic acid, for example an organic achiral acid such as acetic, trifluoroacetic, oxalic, maleic, fumaric or p-toluenesulphonic acid, or an organic chiral acid such as L-tartaric acid, dibenzoyl-L-tartaric acid or di-p-toluoyl-L-tartaric acid. Preferred salts of intermediates III, IV, V and VI are fumarate, maleate and oxalate. Preparation of a solid salt offers an opportunity for purification of intermediates in order to prepare the compound of formula VI (OLA) and consequently ticagrelor of high purity. A further advantage of this preferred possibility of using respective salts resides in that the salts of the intermediately obtained compound of formula VI (OLA) are amendable to being used in further subsequent reaction steps according to preferred embodiments and also in an optional one-pot process without intermittent isolation procedures, thereby additionally benefiting from the possibility of further ease and efficiency of final isolation/purification.

In another embodiment of the present invention the compound of formula I is prepared by comprising the steps of (i) providing a compound of formula A

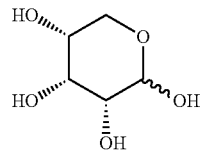

A (ii) contacting the compound of formula A with acetone or acetone ketals and methanol in acidic medium to obtain a compound of formula B

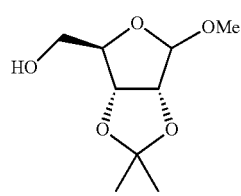

B (iii) contacting the compound of formula B with chlorides or anhydrides of sulfonic acids to give a compound of formula C

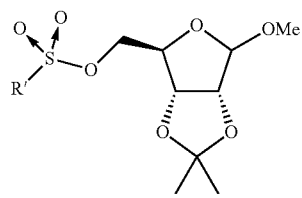

C wherein R' is unsubstituted or fluoro substituted $C_1$-$C_4$-alkyl, unsubstituted or methyl, methoxy, bromo, nitro substituted phenyl, or 10-camphoryl;

(iv) optionally purifying the compound of formula C by recrystallization, (v) treating the compound of formula C with metal or quaternary ammonium halides thereby converting it into a compound of formula D

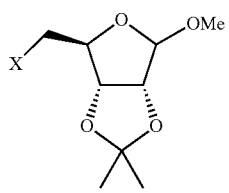

D wherein X is iodo, bromo or chloro, (vi) reducing the compound of formula D with activated zinc, optionally in the presence of copper to give the compound of formula E

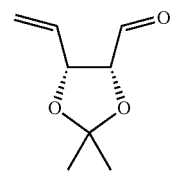

E (vii) treating the compound of formula E with N-monosubstituted hydroxylamines to give a compound of formula F

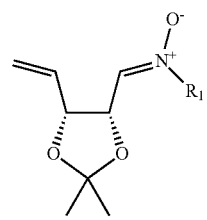

F wherein $R_1$ is $C_4$-$C_5$-tert-alkyl or mono, di- or triphenyl substituted methyl, (viii) thermally transforming the obtained compound of formula F to yield a compound of formula G

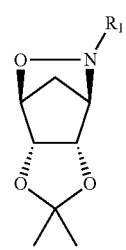

G wherein $R_1$ is as defined above, and either (ix) reducing the compound of formula G to yield the compound of formula I, wherein $R_1$ is $C_4$-$C_5$-tert-alkyl or mono, di- or triphenyl substituted methyl, or (x) reducing the compound of formula G to yield the compound of formula H (AMAL)

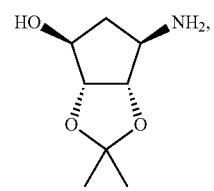

H and

N-substituting the compound of formula H to yield the compound of formula I.

In the first step of the reaction towards the compound of formula I the compound of formula A (D-ribose) is converted into a crystalline sulfonated compound of formula C

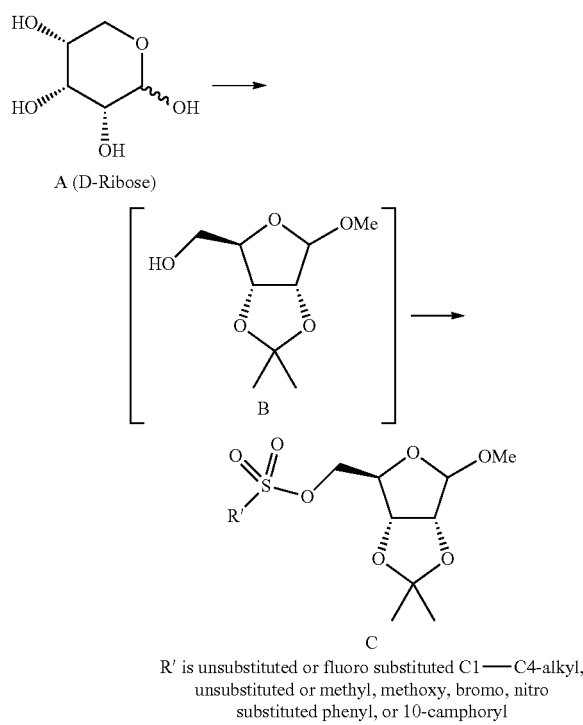

A (D-Ribose)

B

C

R' is unsubstituted or fluoro substituted C1—C4-alkyl, unsubstituted or methyl, methoxy, bromo, nitro substituted phenyl, or 10-camphoryl In the first part of the transformation the glycol group of ribose is protected using 2,2-dimethoxy propane and/or acetone in methanol in the presence of catalytic amounts of acid. The intermediate ((3aR,4R,6aR)-6-methoxy-2,2-dimethyltetrahydrofuro[3,4-d][1,3]dioxol-4-yl)-methanol (B) is not isolated in a pure state, but the reaction is treated by a base, preferably selected from the base used in the next step, most preferably pyridine. Most of volatile compounds solvents are then removed, the residue is extracted by an organic solvent selected from chlorinated hydrocarbons, esters or ethers, preferably by methyl tert-butyl ether, the extract is optionally dried and solution is concentrated and diluted by a pyridine type solvent, selected from pyridine, picolines or lutidine, preferably by pyridine. The obtained mixture is sulfonated by an addition of a chloride or anhydride of a sulfonic acid selected from unsubstituted or fluoro substituted $C_1$-$C_4$-alkanesulfonic acids, or unsubstituted or methyl, methoxy, bromo, nitro substituted, preferably para substituted benzenesulfonic acids, or camphor-10-sulfonic acid, followed by demoisturing with drying agent such as sodium or magnesium sulfate and removal of solvent under reduced pressure. The sulfonates of formula C, such as ((3aR,4R,6aR)-6-methoxy-2,2-dimethyltetrahydrofuro[3,4-d][1,3]dioxol-4-yl)methyl 4-methylbenzenesulfonate (C', compound C, R'=p-tolyl) or ((3aR,4R,6aR)-6-methoxy-2,2-dimethyl-tetrahydrofuro[3,4-d][1,3]dioxol-4-yl)methyl methanesulfonate (C", compound C, R'=Me) are solid crystalline materials, which are optionally purified by recrystallization from appropriate solvent such as 2-propanol to give very pure compounds.

In the further step of the invention sulfonates of Formula C are converted to halo derivatives of Formula D, wherein X is chloro, bromo or iodo, preferably bromo, and iodo, by treating with corresponding metal or quaternary ammonium halides, preferably by tetrabutylammonium chloride, lithium bromide or sodium iodide.

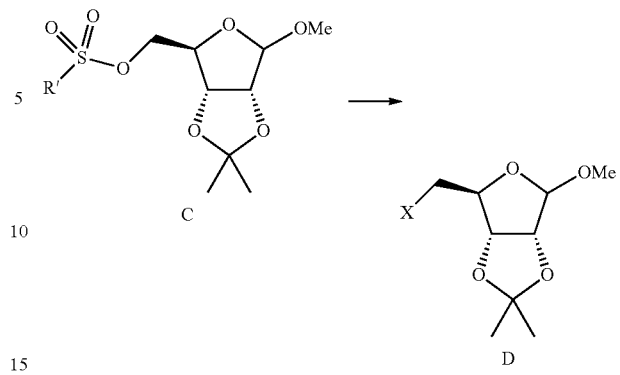

C

D

The conversion is carried out in a medium consisting of a polar solvent, selected from nitriles, amides or ketones, preferably in ketones, most preferably in butanone. All three representatives are oily materials. There is an advantage of using solid sulfonated derivatives of formula C in comparison to the methods, which use oily material such as the compound of formula B. Solid material can be recrystallized in order to enhance the purity which further leads to preparation of liquid bromo derivative of formula D with enhanced purity in the next step. Such material can be used in further steps without low pressure distillation or column chromatography. Furthermore, the intermediate D can be simply isolated by washing out inorganic salts with further evaporation of solvent. The solvent does not need to be completely evaporated as minor amounts of the solvent do not influence further reaction procedure.

The next technological step of the invention consists of two reaction steps. The first step includes the reduction-elimination opening of tetrahydrofuran ring to give compound E. The reducing agent is selected from organolithium compounds or elementary metals, preferably magnesium or zinc. The reactivity for this conversion is considerably diminishing from iodo to chloro derivatives. Using prior art procedures, such as butyl lithium in THF (Eur. J. of Org. Chem. 2001, 1293-1308) at low temperatures or zinc in refluxing alcohols (J. Org. Chem. 1995, 60, 7849-56, Tetrahedron: Asymmetry 2010, 21, 216-221), D' (X=I) is converted to E in high yields, while D" (X=Br) gives poor yields and D"' (X=Cl) is practically not converted. We surprisingly found that in situ activation of zinc by acid such as hydrochloric acid makes the wanted conversion of D' in alcohol at room temperature (20-30° C.). Zinc is activated by an acid such as hydrochloric acid or acetic acid. Furthermore, we surprisingly found that addition of catalytic amounts of copper salts to activated zinc or the use of activated zinc-copper couple in place of zinc alone enhances the conversion of D" to E in acceptable yields at 20-40° C.

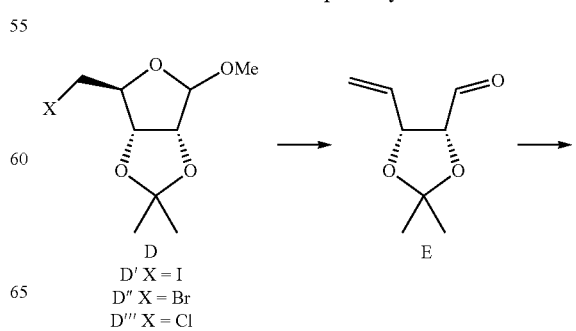

D
D' X = I
D" X = Br
D"' X = Cl

E

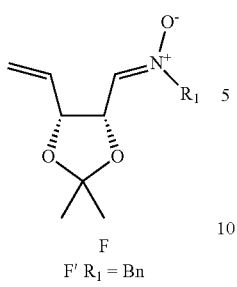

F
F' R₁ = Bn

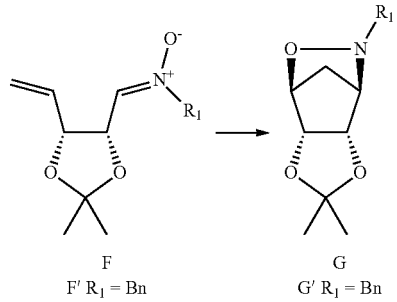

F                    G
F' R₁ = Bn           G' R₁ = Bn

Intermediate E is unstable oil, so it can be further transformed without isolation with N-monosubstituted hydroxylamines into the compound of Formula F, wherein $R_1$ is selected from $C_4$-$C_5$-tert-alkyl, for example tert-butyl (t-Bu), or mono, di- or triphenyl substituted methyl, for example benzyl (Bn). Preferably N-(((4S,5R)-2,2-dimethyl-5-vinyl-1,3-dioxolan-4-yl)methylene)-1-phenylmethanamine oxide (F') is prepared by first reacting it with N-benzylhydroxylamine or its salt in water miscible solvents preferably selected from $C_1$-$C_4$-alcohols, most preferably methanol and water, optionally (if salt of the N-benzylhydroxylamine is used) in the presence of a base, and subsequent crystallization from water. F' is isolated directly from reaction mixture of E after removal of excess zinc by precipitation with water after solvent removal.

F' can then be thermally transformed into (3aS,4S,7R,7aS)-6-benzyl-2,2-dimethyltetrahydro-3aH-4,7-methano[1,3]dioxolo[4,5-d][1,2]oxazine (G') by heating F' in appropriate solvent such as toluene, chlorobenzene or xylenes at elevated temperatures. Surprisingly, toluene as a more industry friendly solvent gives even better results than prior art chlorobenzene isolating crude G' almost quantitatively.

In one option intermediate H can be obtained by reduction of G, for example G', in the presence of hydrogen and metal catalyst such as palladium on charcoal (J. Org. Chem. 2005, 70 6884-90) or Raney nickel in a solvent such as methanol.

In another option G, for example G', is only partially reduced to yield directly the compound of formula I wherein $R_1$ is $C_4$-$C_5$-tert-alkyl or mono, di- or triphenyl substituted methyl, for example N-benzyl derivative by zinc in appropriate solvent (J. Chem. Soc. Perkin Trans. I., 1994, 613-14), which can be further debenzylated to H by reduction with hydrogen or hydrogen donor, such as ammonium formate, and metal catalyst such as palladium on charcoal or Raney nickel and in an appropriate solvent such as methanol.

The compound of formula I, wherein $R_1$ is selected from $C_4$-$C_5$-tert-alkyl, mono-, di-, or triphenyl substituted methyl, tert-butyloxycarbonyl (Boc), benzyloxycarbonyl (Z), trifluoroacetyl (TFA), trichloroacetyl (TCA), formyl, acetyl (Ac), benzoyl (Bz), or fluorenylmethyloxycarbonyl (Fmoc), are prepared from H by corresponding substituting reagents according to well-known approaches from literature or optionally from corresponding analogues of formula F. Optionally some analogues, such as t-butyl or trityl can be prepared from corresponding compounds of formula G (Scheme 9).

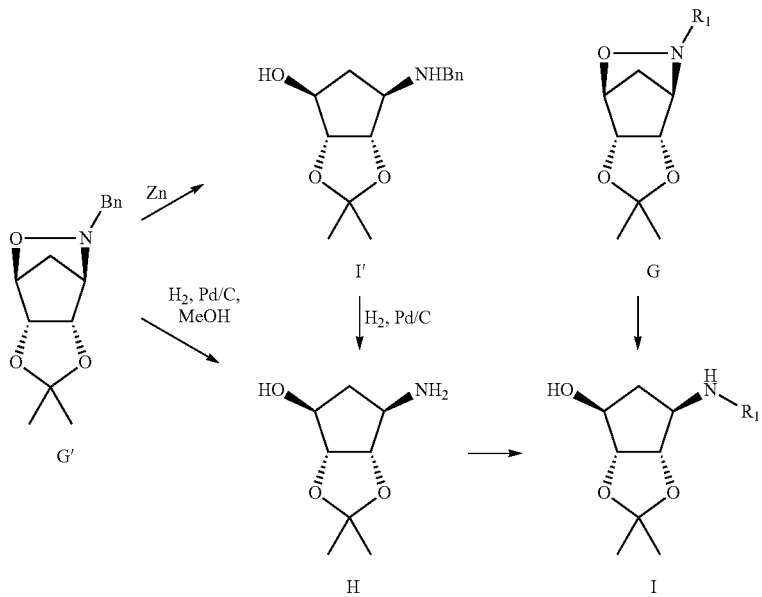

Scheme 9 showing alternative way of preparing compound of formula I.

In another embodiment of the present invention, the compound of formula VI in its racemic form, VI$_r$,

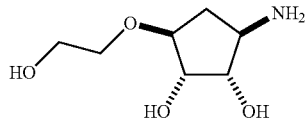

VI$_r$ is prepared by comprising the steps of:
(i) providing a compound of formula J$_r$

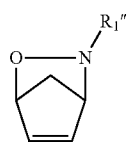

J$_r$ wherein R$_1$" represents a group selected from —CO—R', —CS—R', SO—R', —SO$_2$—R', —PO(R$_x$')(R$_y$'), wherein R', R$_x$', R$_y$' are the same or different and are selected from substituted or unsubstituted (C$_1$-C$_6$)-alkyl, benzyl or aryl; (C$_1$-C$_6$)-alkyloxy, benzyloxy; (C$_1$-C$_6$)-alkylthio; NR$_x$"R$_y$", wherein R$_x$" and R$_y$" are the same or different and selected from (C$_1$-C$_6$)-alkyl, benzyl, aryl, or are coupled to C$_4$-C$_6$-alkylene, 3-oxa-1,5-pentylene, 3-aza or 3-(C$_1$-C$_4$)alkylaza-1,5-pentylene;
(ii) reacting the compound of formula J$_r$ with a compound of formula Z

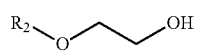

Z wherein R$_2$ is Bn, t-Bu, TBDMS, MOM, Tr, Ac or Bz, to yield a compound of formula K$_r$

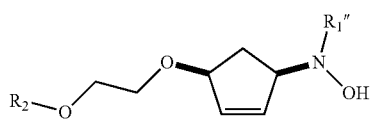

K$_r$ wherein R$_1$" and R$_2$ are as defined above
(iii) oxidising the compound of formula K$_r$ to obtain a compound of formula L$_r$

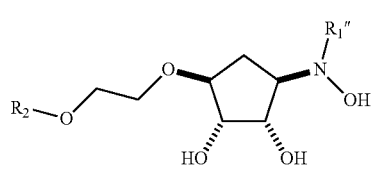

L$_r$ wherein R$_1$" and R$_2$ are as defined above (iv) reducing the hydroxyamino moiety of formula L$_r$ to obtain a compound of formula IV$_r$

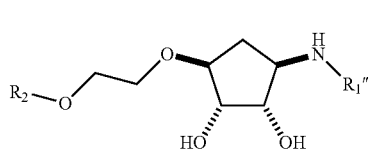

IV$_r$ wherein R$_1$" and R$_2$ are as defined above
(v) converting a compound of formula IV$_r$ to a compound of formula VI$_r$ by removing protecting groups R$_1$ and R$_2$, optionally in two steps via intermediates of formula M$_r$ or N$_r$.

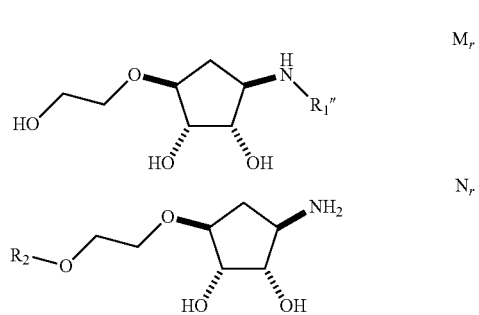

M$_r$

N$_r$ wherein the substituents R$_1$" or R$_2$ remain as above,
(vi) optionally converting a compound of formula VI$_r$ to a salt thereof.

In an alternative option of this embodiment the step (iii) is followed by
(iv') removing protecting groups R$_1$ and R$_2$ from the compound of formula L$_r$, optionally via intermediates of formula P$_r$, or O$_r$.

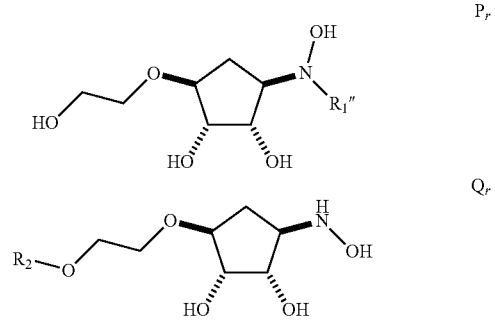

P$_r$

Q$_r$ wherein R$_1$" or R$_2$ remain as above, to give the compound S$_r$

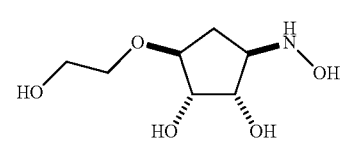

S$_r$ (v') reducing the hydroxyamino moiety of formula S$_r$ to obtain the compound of formula VI$_r$.

(vi') optionally converting a compound of formula VI$_r$ to a salt thereof.

In yet another alternative option of this embodiment, wherein R$_1$ is reductively cleavable protecting group the step (iii) is followed by (iv") removing the protecting group R$_1$" and reducing the hydroxyamino moiety simultaneously in the same reaction mixture to give the compound III$_r$

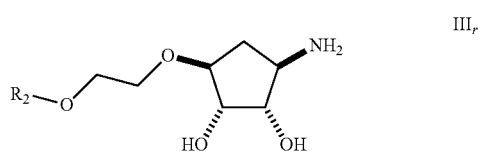

III$_r$ wherein R$_2$ is as defined above (v") removing the protecting group R$_2$ to obtain the compound of formula VI$_r$, (vi") optionally converting a compound of formula VI$_r$ to a salt thereof.

In the most preferred option of this embodiment, wherein R$_1$" and R$_2$ are reductively cleavable protecting group the step (iii) is followed by a single step:

(vii) removing protecting groups R$_1$" and R$_2$, and reducing the hydroxyamino moiety simultaneously in the same reaction mixture to obtain the compound of formula VI$_r$.

(viii) optionally converting a compound of formula VI$_r$ to a salt thereof.

In yet another alternative option of this embodiment, the steps (iii) to (vi) are replaced by:

(ix) reducing the hydroxyamino moiety of formula K$_r$ to obtain a compound of formula T$_r$

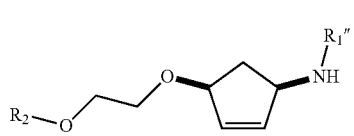

T$_r$ wherein R$_1$" and R$_2$ are as defined above (x) removing protecting groups R$_1$" and R$_2$ in two steps to via an intermediate of formula T$_r$, wherein one of the substituents R$_1$" or R$_2$ is hydrogen, and the remaining is defined as above, or in one step to give the compound U$_r$.

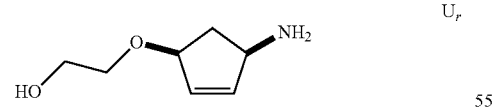

U$_r$ (xi) oxidising the compound of formula U$_r$ to obtain a compound of formula VI$_r$, (xii) optionally converting a compound of formula VI$_r$ to a salt thereof.

Enantiomerically pure intermediate of formula VI (OLA) can be prepared by separation of enantiomers with chiral chromatography of any intermediate of formula J$_r$, K$_r$, L$_r$, M$_r$, N$_r$, P$_r$, or Q$_r$, respectively, and following the same further steps as for racemic compounds.

The racemic compound J$_r$ can be obtained from cyclopentadiene by Diels-Alder reaction with nitroso derivatives in one to three steps, depending whether the protecting group is introduced directly or it is exchanged by a more appropriate one (Tetrahedron 37, 629 (1981), Tetrahedron Lett., 33, 3583 (1992), Tetrahedron, 53, 3347 (1997), Tetrahedron Lett., 41, 9537 (2000), J. Org. Chem., 66, 2466 (2001), Org. Lett., 7, 3605 (2005), Org. Lett., 13, 3442 (2011).

In a preferred option of this embodiment the process starts with enantiomerically pure compound of formula J

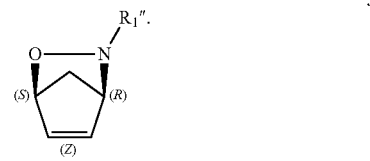

J

Enantiomerically enriched compound of formula J or enantiomerically pure compound of formula J with high enantiomerical excess can be prepared as described in the art (Tetrahedron Lett., 29, 6173 (1988), Synlett, 1989, 32, Tetrahedron Lett., 36, 7535 (1995), J. Org. Chem. 62, 3806 (1997), Tetrahedron, 54, 10537 (1998), Bioorg. Med. Chem. Lett., 16, 3966 (2006), J. Org. Chem., 63, 885 (1998), and WO 11/023374A1) by introducing a chiral group R$_1$ of appropriate chirality to generate 1(S),4(R)-enantiomer.

Using a chiral starting compound of formula J, the process of the invention follows the same steps as described above when starting from the racemic starting material, providing the analogous chiral intermediates of formula K, L, M, N, P, Q, S, T, and U:

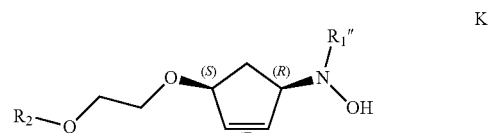

K

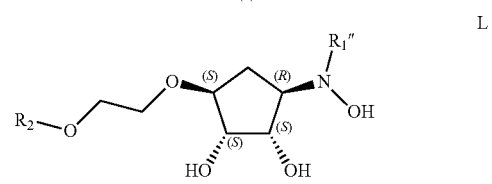

L

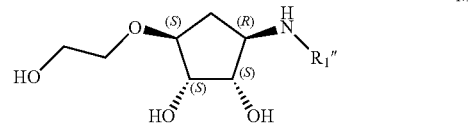

M

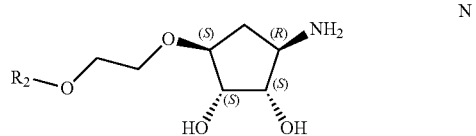

N

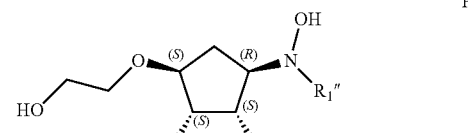

P

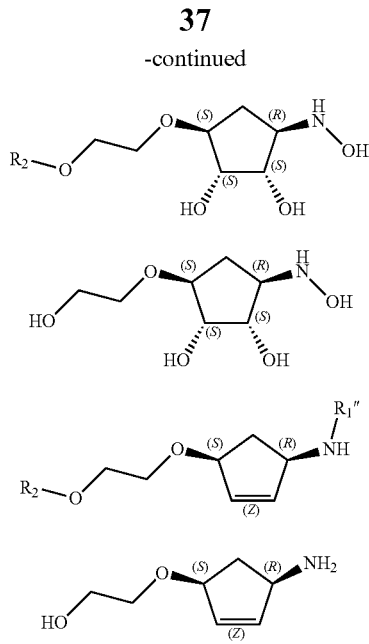

to give the compound of formula VI

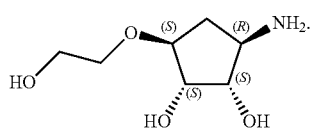

The compound of formula VI (OLA) obtained in this manner can optionally be further converted to a salt thereof as described above.

The preferred group $R_1''$ in the compound of formula J is selected from the group consisting of benzyloxycarbonyl (Cbz), substituted benzyloxycarbonyl and tert-butyloxycarbonyl (BOC), and the preferred group $R_2$ in the compound of formula Z is selected from the group selected from benzyl (Bn), tert-butyldimethylsilyl (TBDMS) and trityl (Tr).

Step (ii) of the reaction described above is carried out in a weakly polar to non-polar solvent, for example toluene, in the presence of a metal salt, such as palladium dichloride, iron (III) chloride, copper(II) sulfate or copper(II) chloride, to give a compound of formula K or $K_r$. A preferential syn opening of compounds of formula J or $J_r$ with simple alcohols, for example methanol, 2-propanol or tert-butanol, in toluene by use of copper (II) chloride, copper(II) sulfate or iron(III) chloride is described in J. Org. Chem. 66, 2466 (2001). The syn opening is a sensitive transformation, dependent on stereo environment, being favoured in more bulky alcohols. Ethylene glycol, for example, predominantly leads to anti product:

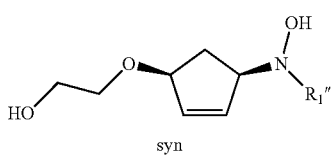
syn

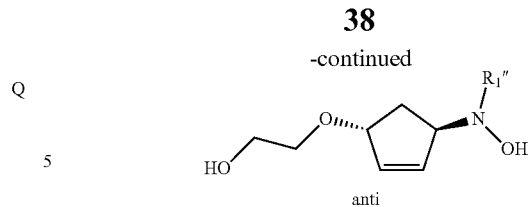
anti

Surprisingly, a reaction with mono O-substituted glycols of formula Z leads to products of formula K or $K_r$ with good syn selectivity, despite the fact that glycols do not possess a bulky α-C atom.

In step (iii) the compound of formula K or $K_r$ is oxidized to a compound of formula L or $L_r$ respectively by the use of common reagents and/or catalysts for cis-dihydroxylation, such as potassium permanganate or osmium tetroxide, with cooxidant, such as N-methylmorpholine-N-oxide (NMO), in an appropriate solvent (Chem. Soc. Rev., 40, 114, 2011).

In step (iv) the hydroxyamino group in the compound of formula L or $L_r$ is reduced by a transition metal in a lower oxidation state, preferably by elemental iron or zinc in acidic condition, or by catalytic hydrogenation, preferably on palladium on a supporter, such as palladium on charcoal. If the protecting groups $R_1''$ and $R_2$ are inert to the reduction, this step leads to the compound of formula IV or $IV_r$, respectively.

The protecting groups $R_1''$ and $R_2$ are removed in step (v) by a chemical reaction typical for the deprotection of the particular protecting group. If both groups are sensitive in these conditions, the transformation leads directly to the compound of formula VI or $VI_r$, while if they need different conditions the deprotection is carried out in two steps via intermediates of formula M or $M_r$ and N or $N_r$, respectively. For example if $R_1''$ is Boc and $R_2$ is tert-butyldimethylsilyl, the compound can be first submitted to the reaction with fluoride anion to decouple the silyl protection followed by hydrolytic removal of Boc group, or the transformation is performed by reverse order of steps. But for example if $R_1''$ is Boc and $R_2$ is trityl, both groups can be decoupled in hydrolytic conditions.

Alternatively, if protecting groups are inert to reduction, the deprotection process can be performed before the reduction following the steps (iv') and (v') to give intermediates of formula P or $P_r$, Q or $Q_r$, and S or $S_r$, which are finally reduced to the product of formula VI or $VI_r$.

In a process, wherein one protecting group, preferably $R_1''$, is cleavable, the process of reduction of hydroxyamino group follows the step order (iv'') and (v'') to give the same product of formula VI or $VI_r$. For example if $R_1''$ is benzyloxycarbonyl (Cbz) the group is decoupled simultaneously by catalytic hydrogenation to give the compound of formula III or Such conversion can also be carried out in a reverse step order.

The protecting groups $R_1''$ and $R_2$ are most preferably selected in such way that they can be removed simultaneously in unique reaction conditions together with the reduction of hydroxyamino group. Preferably, $R_1''$ is benzyloxycarbonyl (Cbz) or substituted benzyloxycarbonyl, and $R_2$ is unsubstituted or substituted benzyl. Both $R_1''$ and $R_2$ are removed with catalytic hydrogenation on palladium on charcoal.

The specifically preferred process according to the invention, wherein $R_1''$ is Cbz and $R_2$ is Bn is shown in Scheme 10

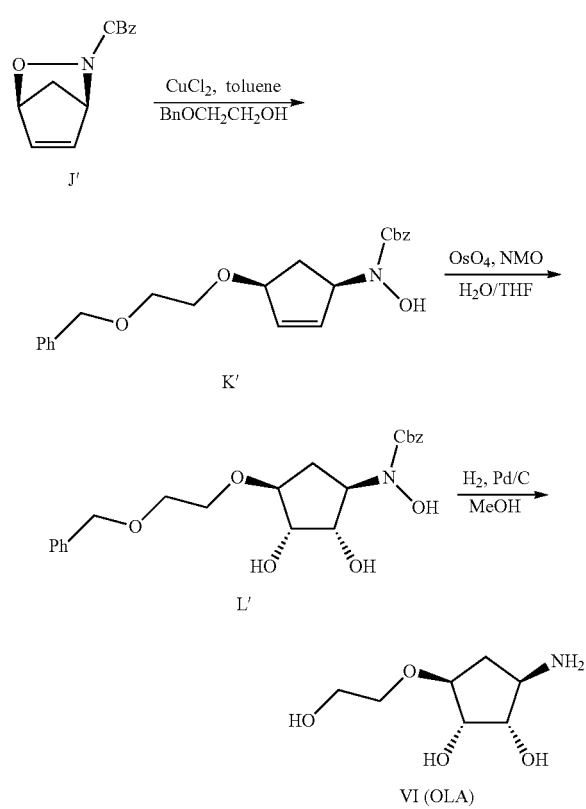

Scheme 10 showing preferred embodiments of the process of the present invention.

The compound of formula J' is treated by an excess of benzyloxyethanol, preferably in 1 to 8 fold molar excess in the presence of cupric chloride in aprotic solvents such as toluene or xylene at 0-40° C., preferably at room temperature for at least 6 hours, preferably from 12 to 20 hours. Copper salts are removed by washing the organic solvent with water after optional complexation with EDTA and the product of formula K' is recovered by evaporation.

The cyclopentene intermediate of formula K' is oxidized by catalytic amount of osmium tetroxide, preferably in 1-8 molar % amount in the presence of the excess amount of cooxidant N-methylmorpholine-N-oxide in a wet ether solvent at 0-40° C. preferably at room temperature from 12 to 64 hours preferably from 16 to 24 hours. Reagents are removed by water; the product of formula L' is re-extracted with an organic solvent, preferably tetrahydrofuran and recovered by evaporation.

In the final step, the compound of formula L' is converted to a compound of formula VI by simultaneous cleaving of the Cbz and Bn groups and reducing the N—OH group to NH group using catalytic hydrogenation over palladium. The catalytic hydrogenation can be carried out over palladium on support, such as charcoal and by the use of hydrogen or hydrogen donor such as formic acid or salts of formic acid in an inert solvent, preferably selected from alcohols, such as methanol, optionally in the presence of a short chain aliphatic acid, preferably acetic acid, at 10 to 50° C., preferably at 30 to 40° C., for 1 to 10 days, preferably 2 to 3 days. The suspended residues are filtered off and the product of formula VI is recovered by evaporation and optionally purified by column chromatography.

The preparation of the compound of formula VI (OLA) according to the present invention needs only 3 steps from the compound of formula J and only about 5 steps from cyclopentadiene. It is considerably shorter than the state of the art process from cyclopentadiene, which is about 10-12 steps long. It is also shorter than the synthesis from D-ribose, which needs 8-10 steps. It is even shorter than the most advantageous synthesis of the protected intermediate AMALA, which is a common intermediate in the synthesis of ticagrelor. The number of steps is an important feature in the overall synthesis of ticagrelor, wherein the number of steps including the synthesis of pyrimidine part and the cyclopropane part exceeds 20 steps.

In another embodiment, the compound of formula AMALA can be easily prepared from the intermediates prepared by the present invention, by protection of glycolic part according to the state of the art as shown in Scheme 11.

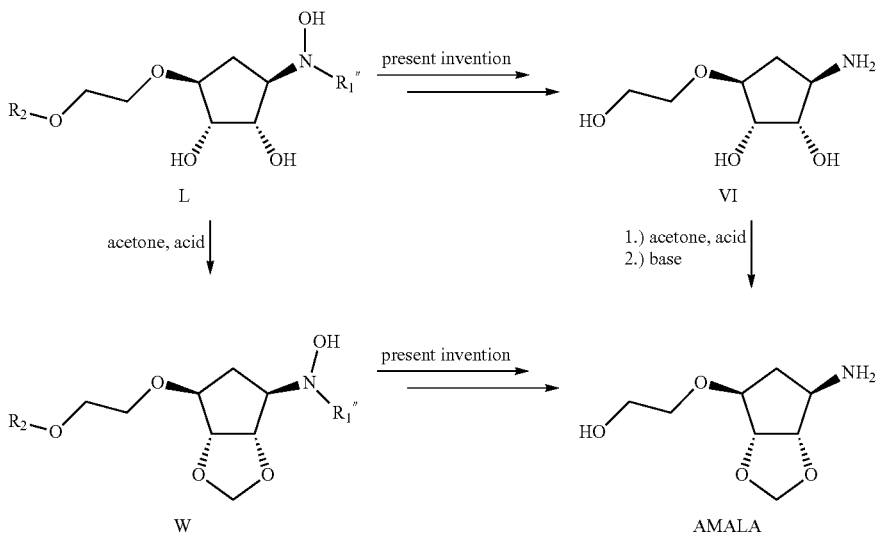

Scheme 11 showing process of preparing AMALA from intermediates of the present invention.

The particularly preferred embodiment of the present invention is a process for preparing a compound of formula XI (ticagrelor, TCG), which is presented in scheme 12.

The starting reactant in the process as illustrated in Scheme 12, i.e. the compound of formula VI (OLA), or a salt thereof, is preferably prepared according to one of the processes described above.

Scheme 12 showing process embodiments of the present invention.

The free base aminoalcohol OLA is viscous syrup that has poor solubility in aprotic solvents such as acetone, acetonitrile, tetrahydrofuran, ethyl acetate, dichloromethane and toluene, but is very soluble in lower alcohols and water. It is also relatively well soluble in very polar aprotic solvents such as dimethyl sulfoxide (DMSO), N,N-dimethylformamide (DMF) and N-methylpyrrolidin-2-one (NMP), or in a solvent

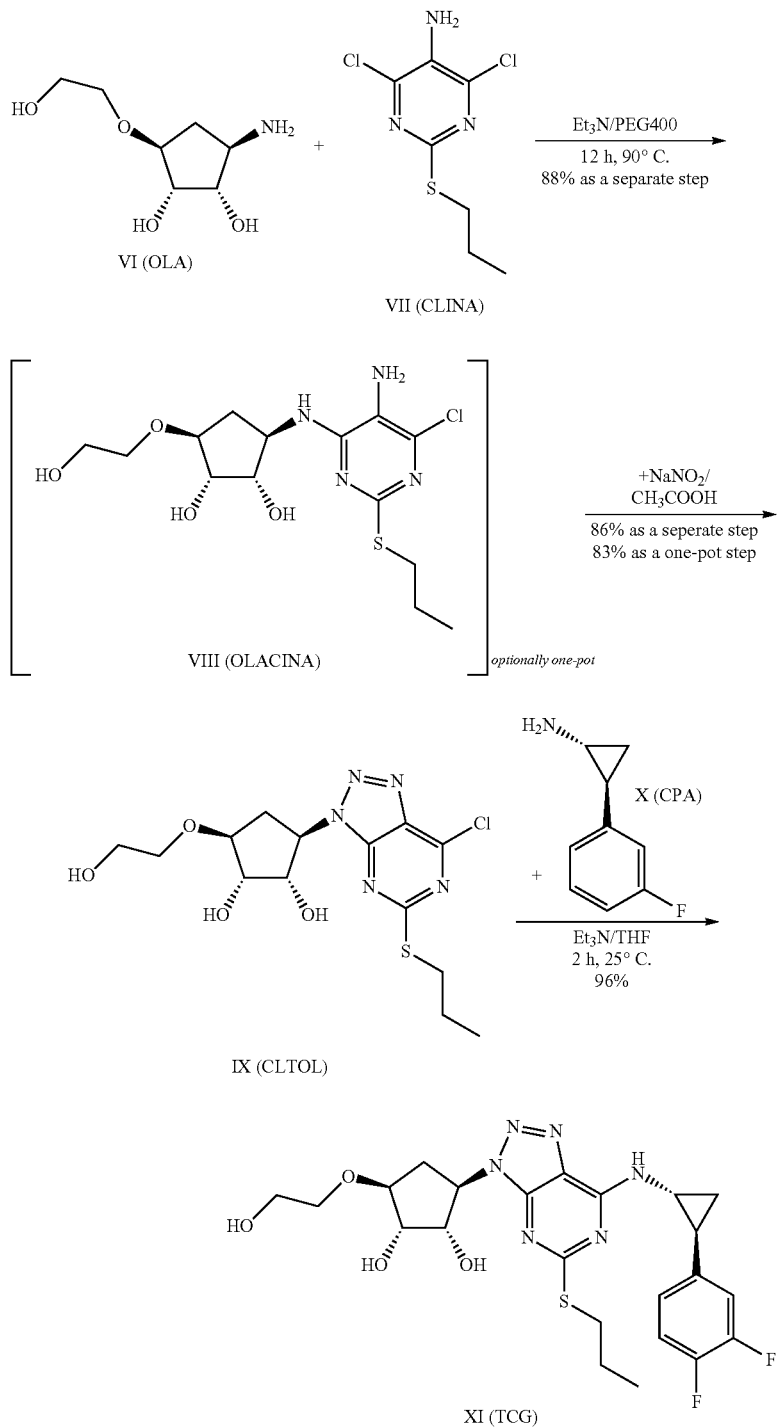

such as polyethyleneglycol (PEG). In particular, a certain amount of polyethyleneglycol to solubilize OLA, CLINA and triethylamine was found suitable as a solvent system for the initial N-arylation reaction. Alternatively, alcohols such as 2-propanol, butanols or pentanols can be used. Polyethyleneglycol is a non-toxic, inexpensive and non-volatile solvent that can be easily removed by an aqueous wash. This solvent also allows for the use of bases other than triethylamine, such as sodium or potassium carbonates or bicarbonates. Generally, 1 to 1.5 equivalents of base is used. If a salt of OLA is chosen, then 2 to 2.5 equivalents of base is used. The reaction can also be efficiently performed in the absence of any added solvent by using triethanolamine as a base. Triethanolamine is a tertiary amine that is miscible with both other reactants, OLA and CLINA. The formation of OLACINA requires temperatures of 60 to 100° C. to achieve a satisfactory reaction time. All these bases, triethylamine, triethanolamine and alkali (bi)carbonates, with their pertaining reaction modifications, are suitable for the one-pot integration of the subsequent nitrosation of the formed OLACINA. In this respect, it is not necessary to isolate OLACINA, because yields are improved when applying the one-pot protocols for the synthesis of CLTOL and its impurity profile is not substantially affected. The nitrosation is performed by diluting the reaction mixture with acetic acid and slowly adding sodium nitrite while cooling to about 20° C. The product CLTOL is isolated by dilution with water and extraction. If required, it can be purified by either precipitation from its solutions using an antisolvent such as n-heptane, or recrystallized from solvents such as for example methyl tert-butyl ether or similar. The reaction of CLTOL with the cyclopropylamine CPA is rapid already at ambient temperature (25° C.) and gives ticagrelor in a nearly quantitative yield. Solvent used for this reaction step is for example tetrahydrofuran to which triethylamine as a scavenger for the formed HCl can be added. Instead of CPA base, salts of CPA can also be directly used in this reaction step. For example, CPA mandelate in acetonitrile, with sodium carbonate as a base, gives ticagrelor in a 93% yield. Overall, the total yield of ticagrelor starting from OLA is about 80%.

Alternatively, the N-arylation of OLA can also be performed with the nitropyrimidine CLIN to give crystalline intermediate OLACIN in a 70% yield (Scheme 13). While the selectivity for the monosubstitution of a single chlorine in the nucleophilic aromatic substitution on CLIN is slightly reduced, the advantage of using the nitropyrimidine CLIN is in its high reactivity allowing the reaction to take place in matter of minutes even at 0° C. With reduction of the nitro group, the common intermediate OLACINA is obtained in a pure form without resorting to chromatography. The reduction of the nitro group can be performed by the hydrogenation of OLACIN in acetic acid. The so obtained solution of OLACINA in acetic acid is easily nitrosated by the use of sodium nitrite to give the pyrimidinotriazole intermediate CLTOL. For example, the solution of OLACINA is nitrosated by 1-1.5 molar excess of sodium nitrite in acetic acid or isopentyl nitrite in an organic solvent to give the pyrimidinotriazole intermediate CLTOL. The nitrosation with sodium nitrite in acetic acid is carried out at the temperature lower than 25° C., preferably at 0-5° C. for 20 to 180 minutes. In this manner, CLTOL is obtained in a 71% overall yield from OLACIN by what is essentially a one-pot process. Ticagrelor is then prepared from CLTOL and CPA using the same method as in the original synthetic variant (48% total yield from OLA).

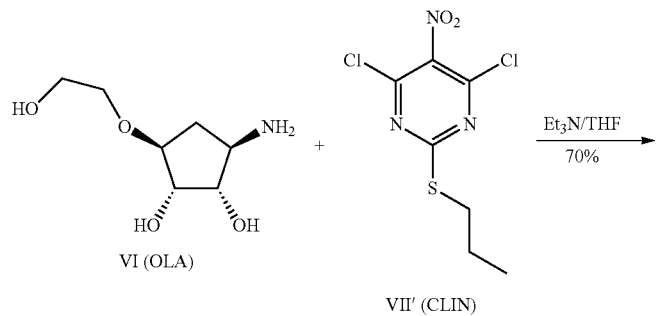

VI (OLA)    VII' (CLIN)

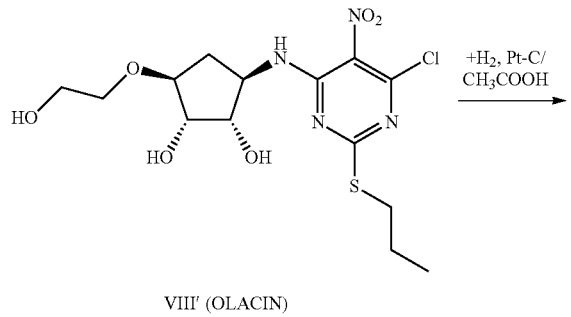

VIII' (OLACIN)

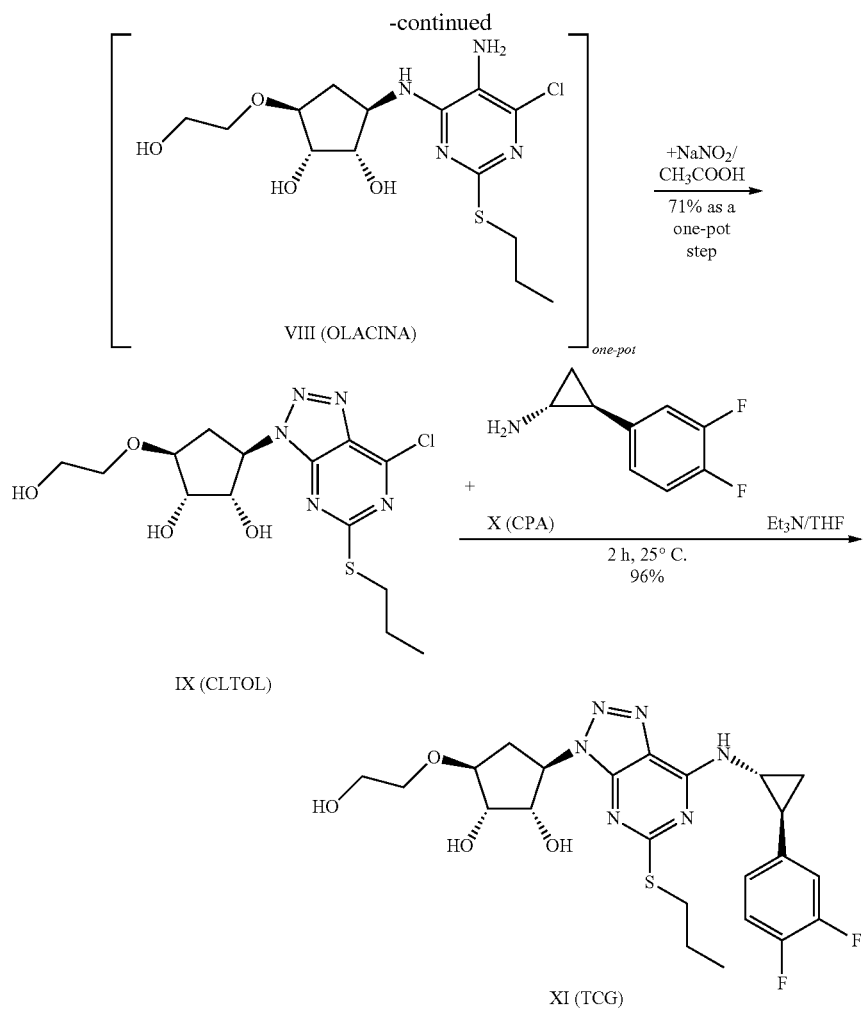

Scheme 13 showing process embodiments of the present invention.

In an alternative embodiment illustrated in Scheme 14 the reaction of nitrosation of OLACINA with sodium nitrite in acetic acid is carried out by at least 1.6 molar excess, preferably 1.8 to 4 molar excess of sodium nitrite in water, for at least 6 hours at the temperature higher than 20° C., preferably at 25° C. to give a new intermediate of formula OHTOL. OHTOL is further converted to ticagrelor by using a coupling reagent, preferably selected from carbodiimides, isouronium salts, such as O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(6-Chlorobenzotriazol-1-yl)-N,N,N',N'-tetramethyluronium hexafluorophosphate (HCTU), 1-[Bis(dimethylamino)methylene]-1H-1,2,3-triazolo[4,5-b]pyridinium 3-oxid hexafluorophosphate (HATU), or oxyphosphonium salts, such as benzotriazol-1-yloxy)tris(dimethylamino) phosphonium hexafluorophosphate (BOP), benzotriazol-1-yloxy)tripyrrolidinophosphonium hexafluorophosphate (PyBOP) in the presence of a base such as DBU, N,N-diisopropylethylamine in a polar aprotic solvent such as dimethylformamide (DMF), dimethylacetamide, acetonitrile and CPA in the form of base or its salt.

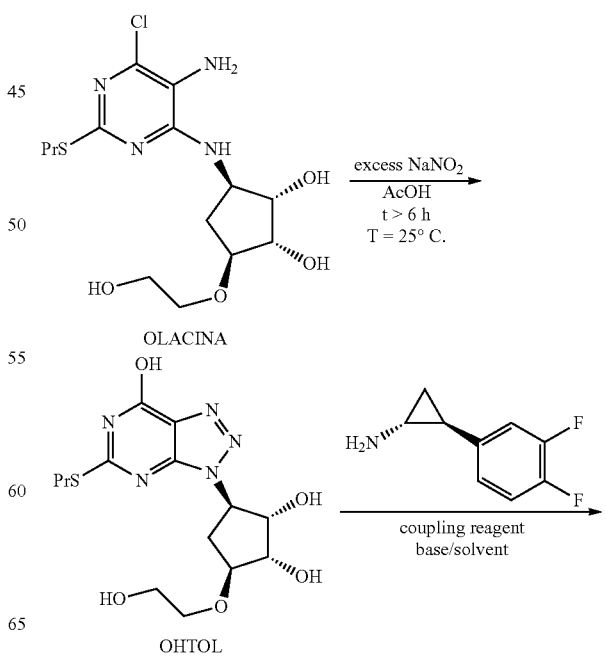

-continued

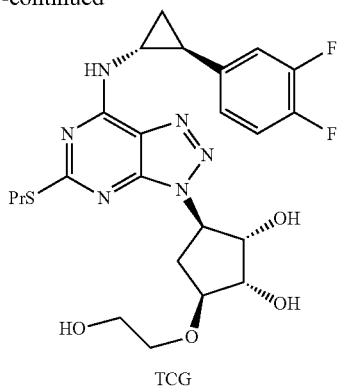

TCG

Scheme 14 showing preparation of ticagrelor via OHTOL.

As set forth above, it is possible and corresponds to a particularly preferred embodiment of the present invention that the intermediate VIII is not isolated. Thus, while of course separation or isolation of the intermediate compound of formula VIII can be carried out to obtain such compound as useful intermediate compound, this can be beneficially dispensed with if desired. This preferred embodiment is not only economically beneficial by the feature that one-pot synthesis is made possible; it is especially advantageous due to the generally amorphous nature of the intermediate compounds, which would make the purification difficult using non-chromatographic means, while the use of chromatographic means would again render the whole process less economically acceptable.

One-pot procedures often cumulate side products. Such procedures, though chemically possible, cannot bring benefits if the product is not efficiently purified. Use of OLA (compound VI) as starting material for the synthesis of ticagrelor offers intermediates, such as OLACIN and CLTOL, which are crystalline. Such phenomenon, which is not predictable, enables purification by recrystallization and consequently one pot transformations without cumulating of side products, which would be removed in case of ticagrelor not earlier than with purification of the final product. The unexpected physical properties of the intermediates make the process of the present invention advantageous to ones described in the state of the art, as the analogous glycol protected intermediates coming from AMALA are all oily materials.

Moreover, as described above, intermediate OLA (compound VI) can be prepared in several ways. According to a preferred process illustrated in Scheme 10, OLA can be prepared in just a few synthetic steps, which shortens the overall number of synthetic steps to ticagrelor. The preferred synthetic approach starting from intermediate J' to ticagrelor is illustrated in Scheme 15. The process of preparing ticagrelor as described herein therefore represents improvement in comparison to the prior art synthetic approaches, in which the intermediate AMALA is used as the starting point in the synthesis of ticagrelor.

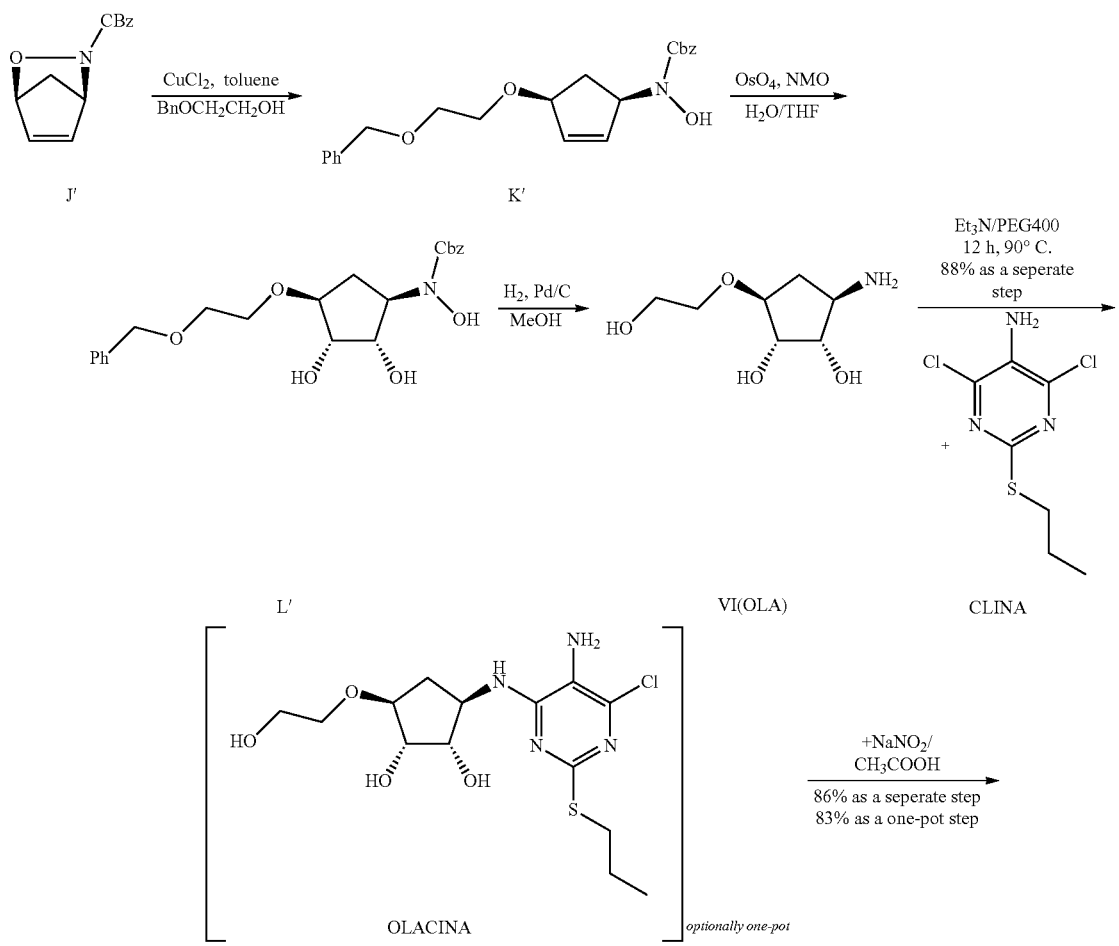

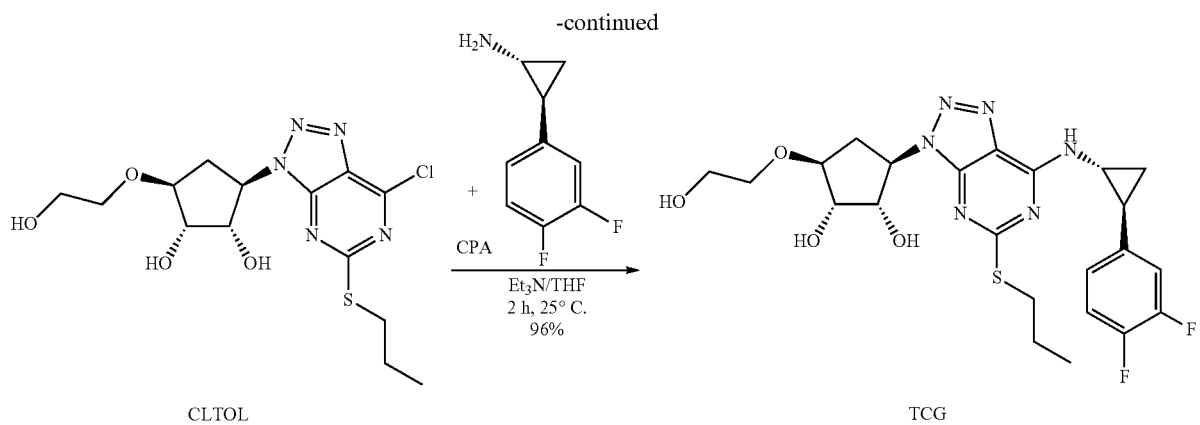

CLTOL + CPA → TCG

Et₃N/THF
2 h, 25° C.
96%

Scheme 15 showing a preferred process embodiment of the present invention.

The ticagrelor compound prepared according to the invention may be used or administered on its own, preferably it is administered as a pharmaceutical composition comprising ticagrelor and a pharmaceutically acceptable excipient and/or carrier. Further, the ticagrelor compound prepared according to the invention may be combined with other drugs, especially drugs having activity against platelet aggregation or thrombolytic events.

In a further aspect of the present invention, a pharmaceutical composition comprising the compound of formula XI (ticagrelor, TCG) or a salt thereof is prepared by comprising the steps of preparing the compound of formula VIII or a salt thereof as described above, and mixing the compound of formula XI or a salt thereof with a pharmaceutically acceptable carrier and/or excipient. The administration form can be suitably chosen, e.g. a form suitable for oral, parenteral, rectal administration and/or administration by inhalation, and the dosage form may be solid, liquid, or powdery. Therefore, the pharmaceutical composition comprising ticagrelor compound prepared according to the invention may suitably be in the form of tablets, pills, capsules, syrups, powders or granules for oral administration; or as sterile parenteral or subcutaneous solutions, suspensions for parenteral administration; or as suppositories for rectal administration.

Suitable excipients and/or carriers include, without being limited to, diluents, binders, disintegrants, lubricants, etc. For example, the compound or a finely divided form thereof, or particles comprising the compound, are mixed with a carrier or binder substance, e.g. a mono-, di- or polysaccharide such as sugars and starch, a sugar alcohol or another polyol. For example, lactose, saccharose, sorbitol, mannitol, starch, cellulose derivatives, a binder such as polyvinylpyrrolidone, and a lubricant such as magnesium stearate, calcium stearate, polyethylene glycol, waxes, paraffin, and the like are mixed, and then compressed into tablets. The compound or a finely divided form thereof or particles containing the same may be coated by another substance. The powder mixture or particles containing the compound may also be dispensed into capsules.

The pharmaceutical composition comprising ticagrelor prepared according to the invention in a desired dose is generally suitable to treat a disease or condition of a patient in need thereof, specifically to display a desired activity against platelet aggregation, or in the treatment or prophylaxis of thrombolytic events.

Further aspects of the present invention reside in the provision of valuable intermediate compounds III to V, K, L, T and salts thereof, and intermediate compounds VIII, VIII', IX and IX', all useful in the synthesis of a compound of formula XI (ticagrelor, TCG):

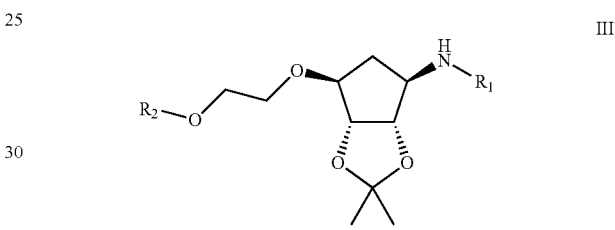

III wherein $R_1$ is tert-butoxycarbonyl (Boc), benzyloxycarbonyl (Cbz), trifluoroacetyl (TFA), trityl (Tr), trichloroacetyl (TCA), formyl (CHO), acetyl (Ac), benzoyl (Bz), fluorenylmethoxycarbonyl (Fmoc), $C_4$-$C_5$-tert-alkyl, preferably tert-butyl (t-Bu), or mono, di- or triphenyl substituted methyl, preferably benzyl (Bn), and $R_2$ is benzyl (Bn), tert-butyl (t-Bu), tert-butyldimethylsilyl (TBDMS), methoxymethyl (MOM), trityl (Tr), acetyl (Ac) or benzoyl (Bz);

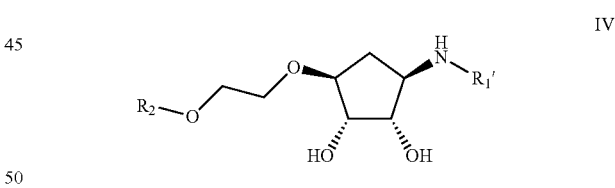

IV wherein $R_1'$ is hydrogen, Boc, Cbz, TFA, Tr, TCA, CHO, Ac, Bz, Fmoc, $C_4$-$C_5$-tert-alkyl, preferably t-Bu, or mono, di- or triphenyl substituted methyl, preferably Bn, and $R_2$ is benzyl (Bn), tert-butyl (t-Bu), tert-butyldimethylsilyl (TBDMS), methoxymethyl (MOM), trityl (Tr), acetyl (Ac) or benzoyl (Bz);

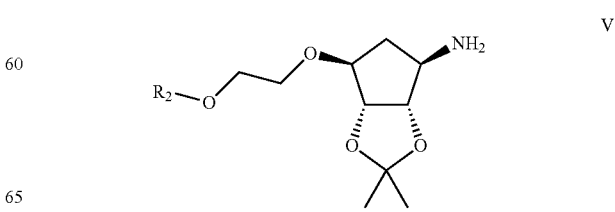

V wherein R₂ is benzyl (Bn), tert-butyl (t-Bu), tert-butyldimethylsilyl (TBDMS), methoxymethyl (MOM), trityl (Tr), acetyl (Ac) or benzoyl (Bz);

K

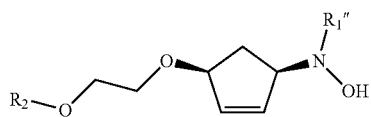

wherein R₁" is hydrogen, —CO—R', —CS—R', SO—R', —SO₂—R', —PO(Rₓ')(R_y'), wherein R', Rₓ', R_y' are the same or different and are selected from substituted or unsubstituted (C₁-C₆)-alkyl, benzyl or aryl; (C₁-C₆)-alkyloxy, benzyloxy; (C₁-C₆)-alkylthio; NRₓ"R_y", wherein Rₓ" and R_y" are the same or different and selected from (C₁-C₆)-alkyl, benzyl, aryl, or are coupled to C₄-C₆-alkylene, 3-oxa-1,5-pentylene, 3-aza or 3-(C₁-C₄)alkylaza-1,5-pentylene, and wherein R₂ is hydrogen, benzyl (Bn), tert-butyl (t-Bu), tert-butyldimethylsilyl (TBDMS), methoxymethyl (MOM), trityl (Tr), acetyl (Ac) or benzoyl (Bz);

L

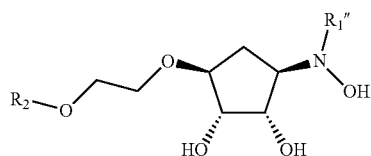

wherein R₁" is hydrogen, —CO—R', —CS—R', SO—R', —SO₂—R', —PO(Rₓ')(R_y'), wherein R', Rₓ', R_y' are the same or different and are selected from substituted or unsubstituted (C₁-C₆)-alkyl, benzyl or aryl; (C₁-C₆)-alkyloxy, benzyloxy; (C₁-C₆)-alkylthio; NRₓ"R_y", wherein Rₓ" and R_y" are the same or different and selected from (C₁-C₆)-alkyl, benzyl, aryl, or are coupled to C₄-C₆-alkylene, 3-oxa-1,5-pentylene, 3-aza or 3-(C₁-C₄)alkylaza-1,5-pentylene, and wherein R₂ is hydrogen, benzyl (Bn), tert-butyl (t-Bu), tert-butyldimethylsilyl (TBDMS), methoxymethyl (MOM), trityl (Tr), acetyl (Ac) or benzoyl (Bz);

T

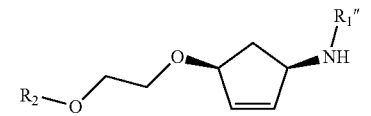

wherein R₁" is hydrogen, —CO—R', —CS—R', SO—R', —SO₂—R', —PO(Rₓ')(R_y'), wherein R', Rₓ', R_y' are the same or different and are selected from substituted or unsubstituted (C₁-C₆)-alkyl, benzyl or aryl; (C₁-C₆)-alkyloxy, benzyloxy; (C₁-C₆)-alkylthio; NRₓ"R_y", wherein Rₓ" and R_y" are the same or different and selected from (C₁-C₆)-alkyl, benzyl, aryl, or are coupled to C₄-C₆-alkylene, 3-oxa-1,5-pentylene, 3-aza or 3-(C₁-C₄)alkylaza-1,5-pentylene, and wherein R₂ is hydrogen, benzyl (Bn), tert-butyl (t-Bu), tert-butyldimethylsilyl (TBDMS), methoxymethyl (MOM), trityl (Tr), acetyl (Ac) or benzoyl (Bz);

A suitable salt of intermediates III, IV, V, K, L and T is a salt of organic acid, for example an organic achiral acid such as acetic, trifluoroacetic, oxalic, maleic, fumaric or p-toluenesulphonic acid, or an organic chiral acid such as L-tartaric acid, dibenzoyl-L-tartaric acid or di-p-toluoyl-L-tartaric acid. Preferred salts of intermediates III, IV and V are fumarate, maleate and oxalate.

VIII

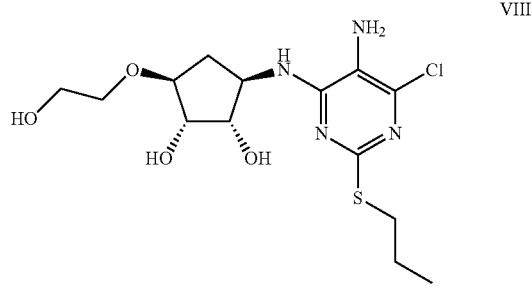

VIII'

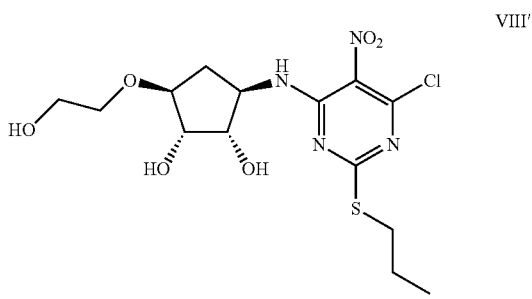

IX

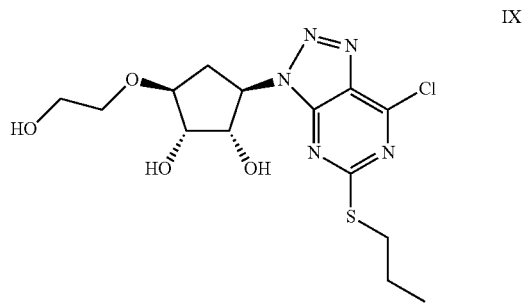

IX'

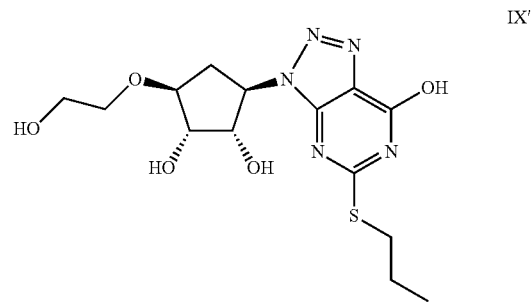

Particular examples of such useful intermediate compounds are listed by their respective formulas below:

| Formula | Chemical name |
|---|---|
| | (3aS,4R,6S,6aR)-N-Benzyl-6-(2-(benzyloxy)ethoxy)-2,2-dimethyltetrahydo-3aH-cyclopenta[d][1,3]dioxol-4-amine |
| | (3aS,4R,6S,6aR)-N-Benzyl-6-(2-(benzyloxy)ethoxy)-2,2-dimethyltetrahydo-3aH-cyclopenta[d][1,3]dioxol-4-amine fumarate |
| | (3aS,4R,6S,6aR)-N-Benzyl-6-(2-tert-butoxy)ethoxy)-2,2-dimethyltetrahydro-3aH-cyclopenta[d][1,3]dioxol-4-amine |
| | (3aS,4R,6S,6aR)-N-Benzyl-6-(2-tert-butoxy)ethoxy)-2,2-dimethyltetrahydro-3aH-cyclopenta[d][1,3]dioxol-4-amine fumarate |
| | tert-Butyl ((3aS,4R,6S,6aR)-6-(2-(benzyloxy)ethoxy)-2,2-dimethyltetrahydro-3aH-cyclopenta[d][1,3]dioxol-4-yl)carbamate |
| | tert-Butyl ((3aS,4R,6S,6aR)-6-(2-(tert-butoxy)ethoxy)-2,2-dimethyltetrahydro-3aH-cyclopenta[d][1,3]dioxol-4-yl)carbamate |

-continued

| Formula | Chemical name |
|---|---|
| | (3aS,4R,6S,6aR)-6-(2-(benzyloxy)ethoxy)-2,2-dimethyl-N-trityltetrahydro-3aH-cyclopenta[d][1,3]dioxol-4-amine |
| | (3aS,4R,6S,6aR)-6-(2-(tert-butoxy)ethoxy)-2,2-dimethyl-N-trityltetrahydro-3aH-cyclopenta[d][1,3]dioxol-4-amine |
| | (1S,2S,3R,5S)-3-(Benzylamino)-5-(2-(benzyloxy)ethoxy)cyclopentane-1,2-diol |
| | (3aS,4R,6S,6aR)-6-(2-(tert-butoxy)ethoxy)-2,2-dimethyltetrahydro-3aH-cyclopenta[d][1,3]dioxol-4-amine |
| | (1S,2S,3S,5R)-3-(2-(benzyloxy)ethoxy)-5-(tritylamino)cyclopentane-1,2-diol |
| | Benzyl ((1R,4S)-4-(2-(benzyloxy)ethoxy)cyclopent-2-en-1-yl)(hydroxy)carbamate |
| | Benzyl ((1R,2S,3S,4S)-4-(2-(benzyloxy)ethoxy)-2,3-dihydroxycyclopentyl)(hydroxy)carbamate |

-continued

| Formula | Chemical name |
|---|---|
| | (1S,2S,3R,5S)-3-((5-amino-6-chloro-2-(propylthio)pyrimidin-4-yl)amino)-5-(2-hydroxyethoxy)cyclopentane-1,2-diol |
| | (1S,2S,3R,5S)-3-((6-chloro-5-nitro-2-(propylthio)pyrimidin-4-yl)amino)-5-(2-hydroxyethoxy)cyclopentane-1,2-diol |
| | (1S,2S,3H,5S)-3-(7-chloro-5-(propylthio)-3H-[1,2,3]triazolo[4,5-d]pyrimidin-3-yl)-5-(2-hydroxyethoxy)cyclopentane-1,2-diol |
| | (1S,2S,3R,5S)-3-(7-hydroxy-5-(propylthio)-3H-[1,2,3]triazolo[4,5-d]pyrimidin-3-yl)-5-(2-hydroxyethoxy)cyclopentane-1,2-diol |

In the following the present invention will be described in further detail by illustrative, non-limiting examples.

EXAMPLES

Example 1

Preparation of ((3aR,4R,6aR)-6-methoxy-2,2-dimethyltetrahydrofuro[3,4-d][1,3]dioxol-4-ylmethanol (B)

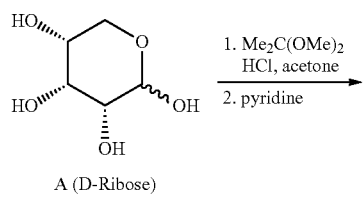

A (D-Ribose)

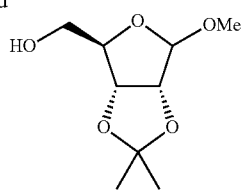

B

To a mixture of A (D-ribose) (100 g), acetone (2.0 L), 2,2-dimethoxypropane (200 mL) and methanol (300 mL) was added a saturated solution of hydrochloride in methanol (100 mL) and the resulting mixture was stirred at 25° C. for 22 hours. Pyridine (55 mL) was added and the solvent was removed under reduced pressure. The oily residue was added to a mixture of water (300 mL) and methyl tert-butyl ether (300 mL; MTBE). Phases were separated and the water phase was extracted two times by 300 mL of MTBE. All MTBE fractions were combined and washed twice with saturated aqueous solution of CuSO$_4$. Combined CuSO$_4$ fractions were extracted with MTBE (100 mL) and MTBE fractions were combined. Combined MTBE fractions were concentrated under reduced pressure and the product was distilled under reduced pressure (0.016 mbar, T=90-94° C.) to yield B (106.4 g, 78.2%) as colorless oil.

$^1$H NMR (CDCl$_3$): δ1.30 (s. 3H), 1.46 (s, 3H), 3.41 (s, 3H), 3.63 (m, 2H), 4.42 (m, 1H), 4.56 (d, 1H), 4.81 (m, 1H), 4.95 (s, 1H).

Example 2

Preparation of ((3aR,4R,6aR)-6-methoxy-2,2-dimethyltetrahydrofuro[3,4-d][1,3]dioxol-4-yl)methanol (B)

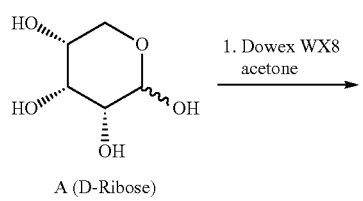

To a mixture of A (D-ribose) (150 g), acetone (0.75 L) and methanol (300 mL) was added a dry Dowex WX8 strongly acidic resin (30 g) and the resulting mixture was stirred at 25° C. for 3 days. Dowex was filtered off (washed with 30 mL of acetone) and sodium hydrogen carbonate (15 g) was added. The resulting mixture was stirred for 10 minutes, the solvents were removed, water (0.3 L) was added and the product was extracted into methyl tert-butyl ether (4×0.25 L). Combined MTBE fractions were dried over magnesium sulfate, filtered and concentrated under reduced pressure to yield B (184 g, 90%).

Example 3

Preparation of (3aS,4S,6aR)-4-(iodomethyl)-6-methoxy-2,2-dimethyltetrahydrofuro[3,4-d][1,3]dioxole (D')

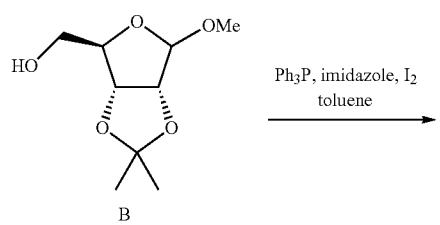

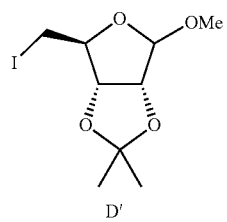

To a mixture of B (35.0 g, 0.171 mol), imidazole (28.0 g, 0.318 mol), triphenylphosphine (54.1 g, 0.206 mol) and toluene (1.14 L) was added iodine (52.15 g, 0.206 mol) at 70° C. and the resulting mixture was stirred for 2 hours. The supernatant was decanted off and the solvent was removed under reduced pressure. The product was distilled under reduced pressure (0.046 mbar; 88-95° C.) to give D' (47.6 g; 89%).

$^1$H NMR (CDCl$_3$): δ 1.25 (s, 3H), 1.40 (s, 3H), 3.09 (m, 1H), 3.21 (s, 1H), 3.29 (s, 3H), 4.36 (m, 1H), 4.56 (m, 1H), 4.69 (m, 1H), 4.97 (s, 1H) ppm.

Example 4

Preparation of ((3aR,4R,6aR)-6-methoxy-2,2-dimethyltetrahydrofuro[3,4-d][1,3]dioxol-4-yl)methyl 4-methylbenzenesulfonate (C') from distilled B

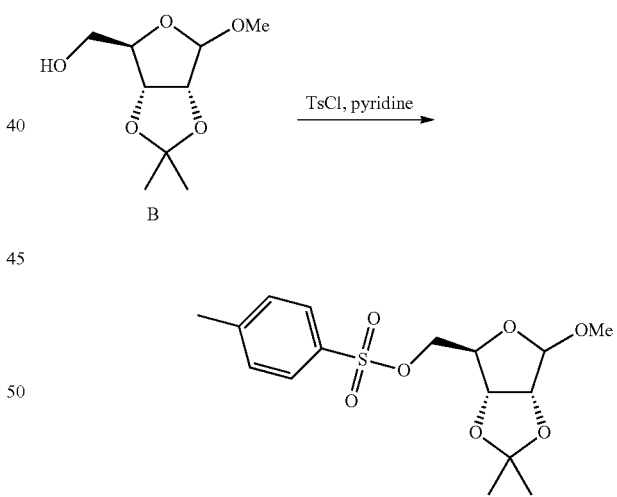

To a mixture of B (20.0 g) and pyridine (50 mL) was added p-toluenesulfonyl chloride (27.6 g, TsCl) at −10° C. The resulting mixture was stirred at −10 to −5° C. for 4 hours and poured into an ice-water mixture (100 g). The precipitated solid (C') was filtered off, washed with water (2×50 mL) and dried to yield C' (32.5 g, 93%).

$^1$H NMR (CD$_3$OD): δ1.27 (s, 3H), 1.41 (s, 3H), 2.47 (s, 3H), 3.20 (s, 3H), 4.01 (m, 2H), 4.24 (m, 1H), 4.52 (d, 1H), 4.60 (d, 1H), 4.89 (s, 1H), 7.47 (m, 2H), 7.82 (m, 2H) ppm.

Example 5

Preparation of ((3aR,4R,6aR)-6-methoxy-2,2-dimethyltetrahydrofuro[3,4-d][1,3]dioxol-4-ylmethyl methanesulfonate (C″) from distilled B

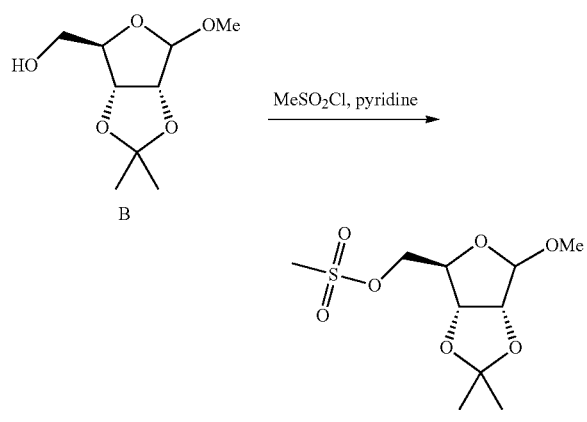

To a mixture of B (30.0 g, 0.15 mol) and pyridine (75 mL) was added methanesulfonyl chloride (24.9 g, TsCl) at 5° C. The resulting mixture was stirred at 0 to 8° C. for 3 hours, then at 25° C. for 16 hours and poured into an ice-water mixture (200 g). The precipitated solid (C″) was filtered off, washed with water and dried. The resulting solid was dissolved in 2-propanol (60 mL) at elevated temperature, cooled and to the mixture was added n-hexane (50 mL). The precipitated solid was filtered off and dried to yield C″ (28.3 g).

$^1$H NMR (CDCl$_3$): δ1.33 (s, 3H), 1.49 (s, 3H), 3.06 (s, 3H), 3.35 (s, 3H), 4.22 (m, 2H), 4.42 (m, 1H), 4.61 (m, 1H), 4.71 (m, 1H), 5.00 (s, 1H) ppm.

Example 6

Preparation of ((3aR,4R,6aR)-6-methoxy-2,2-dimethyltetrahydrofuro[3,4-d][1,3]dioxol-4-ylmethyl 4-methylbenzenesulfonate (C′) from A (D-Ribose) without Distillation

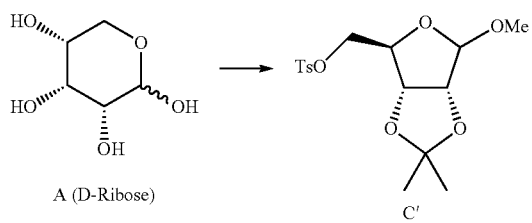 [SMILES: OC1OC[C@@H](O)[C@@H](O)[C@H]1O ; COC1O[C@H](COS(=O)(=O)c2ccc(C)cc2)[C@H]2OC(C)(C)O[C@@H]12]

To a mixture of A (D-ribose) (500 g, 3.34 mol), acetone (10.0 L), 2,2-dimethoxypropane (1.0 L) and methanol (1.4 L) was added a saturated solution of hydrochloride in methanol (0.60 L) and the resulting mixture was stirred at 25° C. for 19 hours. Pyridine (275 mL) was added and the solvents were removed under reduced pressure. To the oily residue was added water (1.5 L) and methyl tert-butyl ether (1.5 mL). Phases were separated and the water phase was extracted two times by 1.5 L of MTBE. All MTBE fractions were combined, dried with magnesium sulfate, filtered and concentrated under reduced pressure to give crude B (661 g).

To a fraction of thus obtained B (227 g) was added pyridine (570 mL). The mixture was cooled to –10° C. and p-toluenesulfonyl chloride (314 g, TsCl) was added. The resulting mixture was stirred at 0-5° C. for 5 hours and poured into cool (18° C.) water (1.5 L). The precipitated solid (C′) was filtered off, washed with water (2×200 mL) and dried. The product was re-crystallized from 2-propanol (600 mL) and dried to yield clean C′ (279 g, 68 from D-ribose).

Example 7

Preparation of (3aS,4S,6aR)-4-(iodomethyl)-6-methoxy-2,2-dimethyltetrahydrofuro[3,4-d][1,3]dioxole (D′)

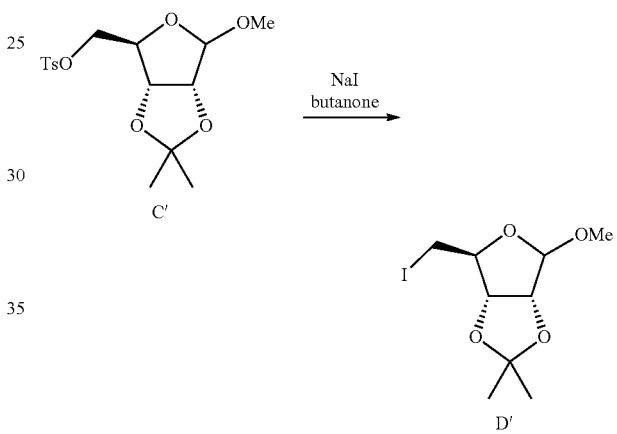

A mixture of C′ (150 g), finely powdered sodium iodide (130 g) and butanone (1.5 L) was stirred at 80° C. for 17 hours. The resulting mixture was cooled to 20-25° C., washed 3 times with saturated aqueous sodium hydrogen carbonate (3×300 mL) and concentrated under reduced pressure to yield D′ (132 g, 100%).

Example 8

Preparation of (3aS,4S,6aR)-4-(iodomethyl)-6-methoxy-2,2-dimethyltetrahydrofuro[3,4-d][1,3]dioxole (D′)

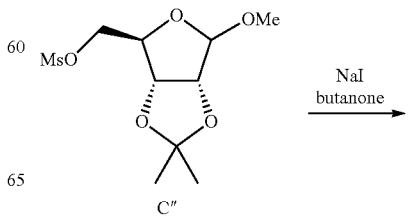

-continued

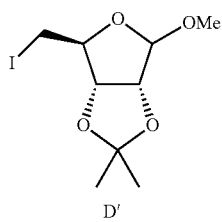

D'

A mixture of C'' (11.8 g), finely powdered sodium iodide (13 g) and butanone (150 mL) was stirred at 80° C. for 22 hours. The resulting mixture was cooled to 20-25° C., washed 3 times with saturated aqueous sodium hydrogen carbonate (3×50 mL), dried over magnesium sulfate and concentrated under reduced pressure to yield D' (100%).

Example 9

Preparation of (3aS,4S,6aR)-4-(bromomethyl)-6-methoxy-2,2-dimethyltetrahydrofuro[3,4-d][1,3]dioxole (D'')

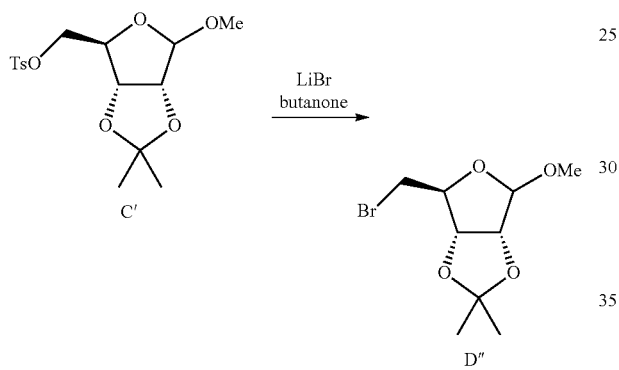

A mixture of C' (6.0 g), lithium bromide (3.0 g) and butanone (60 mL) was stirred at 80° C. for 3 hours and another portion of lithium bromide was added (3.5 g) and stirred at 80° C. for another 19 hours. The resulting mixture was cooled to 20-25° C., washed 3 times with saturated aqueous sodium hydrogen carbonate (3×30 mL) and concentrated under reduced pressure to yield D'' (4.98 g, containing some butanone) as oil.

$^1$H NMR (CDCl$_3$): δ1.30 (s, 3H), 1.46 (s, 3H), 3.27-3.44 (m, 5H), 4.36 (m, 1H), 4.59 (d, 1H), 4.75 (d, 1H), 4.99 (s, 1H) ppm.

Example 10

Preparation of (3aS,4S,6aR)-4-(chloromethyl)-6-methoxy-2,2-dimethyltetrahydrofuro[3,4-d][1,3]dioxole (D''')

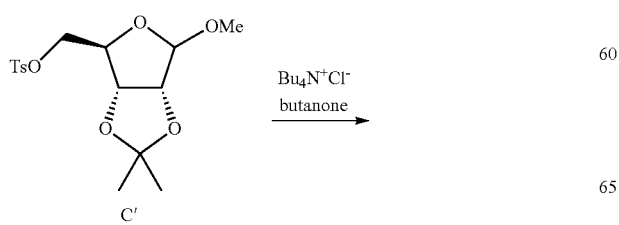

-continued

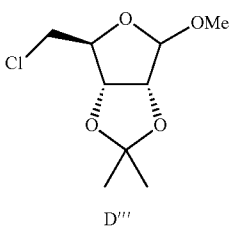

D'''

A mixture of C' (48.0 g), tetrabutylammonium chloride (56.0 g) and butanone (480 mL) was stirred at 80° C. for 20 hours. The resulting mixture was cooled to 20-25° C., washed twice with 1 M aqueous acetic acid saturated with NaCl (2×250 mL), twice with saturated aqueous sodium hydrogen carbonate (2×250 mL) and water (250 mL). The resulting solution was dried over magnesium sulfate, filtered and concentrated under reduced pressure. To the resulting oil was added MTBE (250 mL) and ethyl acetate (100 mL), washed twice with 1 M acetic acid (2×250 mL) and twice with saturated aqueous sodium hydrogen carbonate (2×250 mL). The resulting solution was dried over magnesium sulfate, filtered and concentrated under reduced pressure to yield D''' (27.9 g, 94%) as oil.

$^1$H NMR (CDCl$_3$): δ1.32 (s, 3H), 1.48 (s, 3H), 3.34 (s, 3H), 3.47 (m, 1H), 3.55 (m, 1H), 4.31 (m, 1H), 4.61 (m, 1H), 4.74 (m, 1H), 4.98 (s, 1H) ppm.

Example 11

Preparation of N-(((4S,5R)-2,2-dimethyl-5-vinyl-1,3-dioxolan-4-yl)methylene)-1-phenylmethanamine oxide (F')

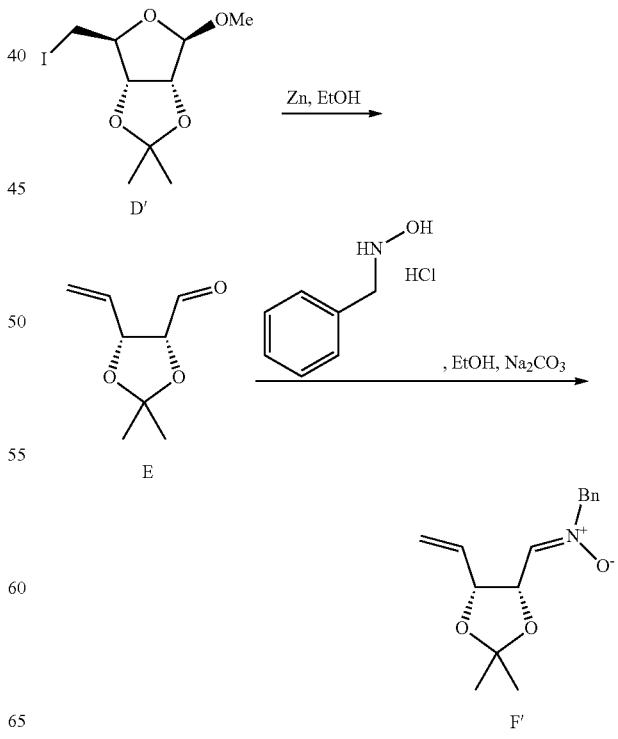

A mixture of zinc (64 g) and ethanol (640 mL) was cooled to 10° C. and 4 M aqueous HCl was added during 10 min. To the resulting mixture was added D' (80 g, 0.26 mol) at 10° C. and the mixture was stirred at 24° C. for 19 hours. The mixture was filtered through Celite. Resulting solution of E was added to a mixture of N-benzylhydroxylamine hydrochloride (41.6 g, 0.26 mol), sodium carbonate (77 g), magnesium sulfate (224 g) and ethanol (640 mL) and stirred at 25° C. for 23 hours. The mixture was filtered through Celite and ethanol was removed under reduced pressure. To the resulting oily residue was added water, the mixture was stirred for 30 min and the precipitated solid was filtered off, washed with water and dried to give F' (64.92 g, 98%).

$^1$H NMR (CDCl$_3$): δ1.37 (s, 3H), 1.48 (s, 3H), 4.79-4.93 (m, 3H), 5.05 (m, 1H), 5.34 (m, 2H), 5.68 (m, 1H), 6.75 (m, 1H), 7.38 (m, 5H) ppm.

Example 12

Preparation of N-(((4S,5R)-2,2-dimethyl-5-vinyl-1, 3-dioxolan-4-yl)methylene)-1-phenylmethanamine oxide (F')

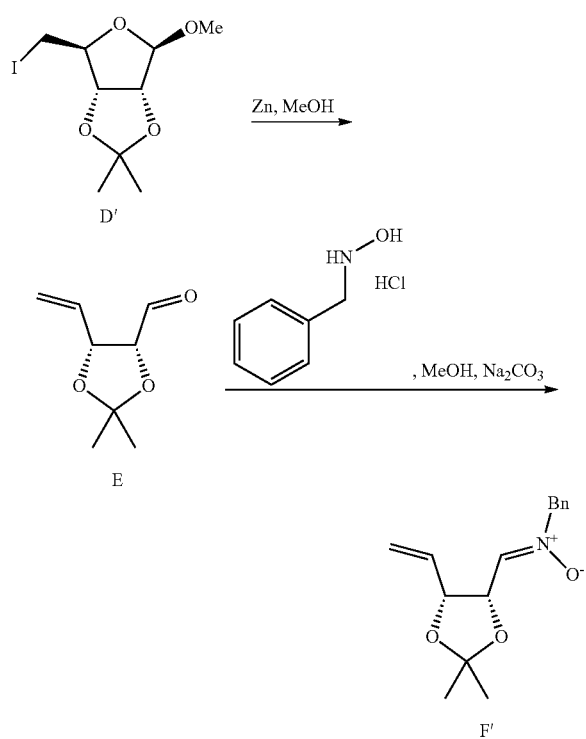

A mixture of finely powdered zinc (109 g) and methanol (1097 mL) was cooled to 20° C. and 4 M aqueous HCl (11 mL) was added during 5 min. To the resulting mixture was added D' (131 g) was stirred for 2.5 hours. The mixture was filtered through Celite. To the resulting solution of E was added water (66 mL), sodium carbonate (66 g) and N-benzylhydroxylamine hydrochloride (66.1 g) stirred at 25° C. for 0.5 hours. The mixture was filtered through Celite and methanol was removed under reduced pressure. To the resulting oily residue was added water, the mixture was stirred for 30 min and the precipitated solid was filtered off, washed with water (200 mL) and dried to give F' (105.8 g, 97%).

$^1$H NMR (CDCl$_3$): δ1.37 (s, 3H), 1.48 (s, 3H), 4.79-4.93 (m, 3H), 5.05 (m, 1H), 5.34 (m, 2H), 5.68 (m, 1H), 6.75 (m, 1H), 7.38 (m, 5H) ppm.

Example 13

Preparation of N-(((4S,5R)-2,2-dimethyl-5-vinyl-1, 3-dioxolan-4-yl)methylene)-1-phenylmethanamine oxide (F')

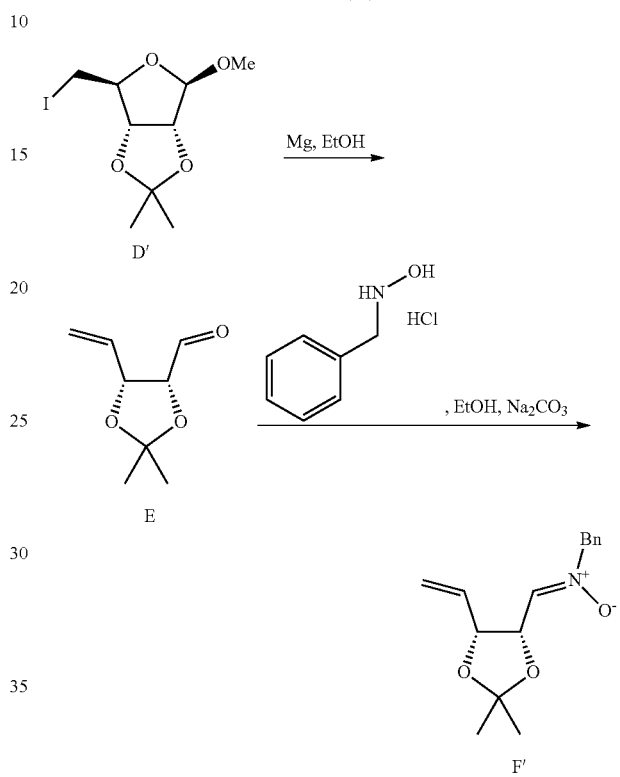

A mixture of D' (5.3 g), magnesium (1.15 g) and ethanol (42 mL) was stirred at 25° C. for 6 hours and the resulting mixture was poured into a mixture of sodium carbonate ((5.1 g), magnesium sulfate (14.8 g), N-benzylhydroxylamine hydrochloride (2.75 g) and ethanol (42 mL). The resulting mixture was stirred at 25° C. for 19 hours and filtered. To the filtrate was added water (0.5 L) and the product was extracted with EtOAc (3×0.3 L). Combined organic phases were concentrated under reduced pressure and the product was purified by chromatography (silica gel; EtOAc, hexane) to give F' (0.62 g, 14%).

Example 14

Preparation of N-(((4S,5R)-2,2-dimethyl-5-vinyl-1, 3-dioxolan-4-yl)methylene)-1-phenylmethanamine oxide (F')

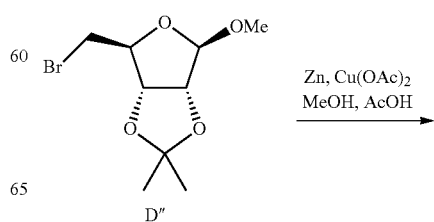

-continued

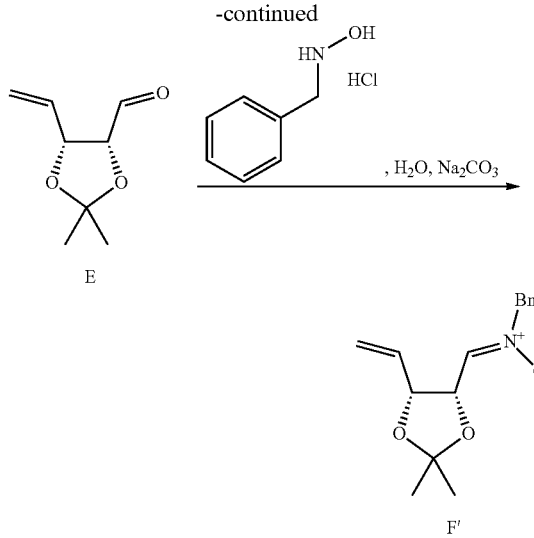

A mixture of zinc (14 g), methanol (160 mL), acetic acid (0.3 mL) and copper (II) acetate (1.4 g) was stirred at 45° C. for 0.5 hour, cooled to 35° C., D" (6.4 g) was added and the resulting mixture was stirred at 35° C. for 4 hours and then at 25° C. for 2 days. The resulting mixture (GC analysis revealed 82 area % of ELMIR) was filtered through Celite and water (10 g), sodium carbonate (3 g) and N-benzylhydroxylamine hydrochloride (2.75 g) were added. The resulting mixture was stirred at 25° C. for 0.5 hour and methanol was removed under reduced pressure, water (200 mL) was added and the mixture was stirred for 30 min, product was filtered off and dried under reduced pressure to yield F' (7.27 g).

Example 15

Preparation of (4R,5R)-2,2-dimethyl-5-vinyl-1,3-dioxolane-4-carbaldehyde (E)

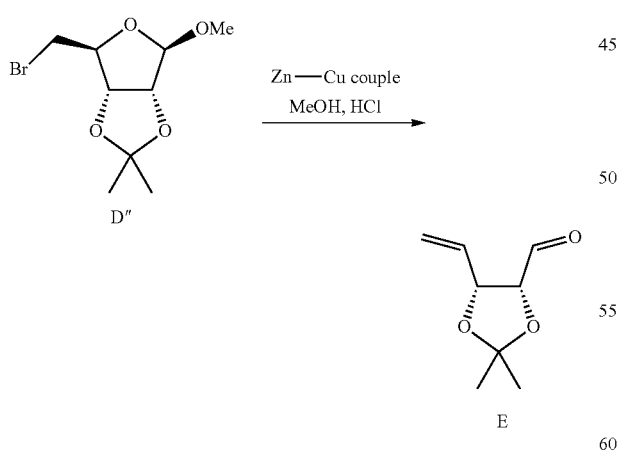

A mixture of zinc-copper couple (6.4 g), methanol (32 mL) and 4M aqueous HCl (0.64 mL) was stirred at 25° C. for 5 minutes, then D" (3.34 g) was added and the resulting mixture was stirred at 25° C. for 18 hours. GC analysis revealed 90 area % (solvent not integrated) of (4R,5R)-2,2-dimethyl-5-vinyl-1,3-dioxolane-4-carbaldehyde.

Example 16

Preparation of (3aS,4S,7R,7aS)-6-benzyl-2,2-dimethyltetrahydro-3aH-4,7-methano[1,3]dioxolo[4,5-d][1,2]oxazine (G')

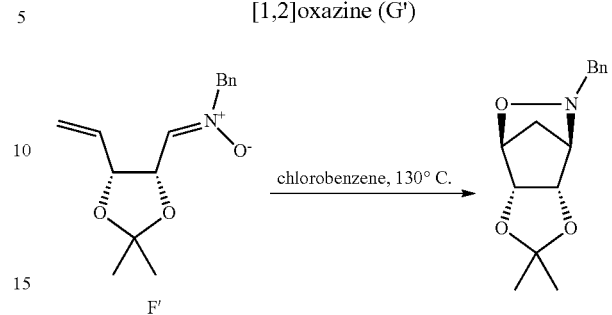

A mixture of F' (9.64 g) and chlorobenzene (0.15 L) was stirred at 130° C. for 1 hour. The resulting mixture was cooled to 60° C. and chlorobenzene was removed by distillation under reduced pressure. The residue was re-crystallized from 2-propanol (70 mL) to give G' (5.23 g, 54%) as dark crystals.
$^1$H NMR (CDCl$_3$): δ1.28 (s, 3H), 1.44 (s, 3H), 2.04 (m, 2H), 3.56 (s, 1H), 3.71 (d, 1H), 4.02 (d, 1H), 4.23 (m, 1H), 4.29 (m, 1H), 4.46 (1H), 7.25-7.36 (m, 5H) ppm.

Example 17

Preparation of (3aS,4S,7R,7aS)-6-benzyl-2,2-dimethyltetrahydro-3aH-4,7-methano[1,3]dioxolo[4,5-d][1,2]oxazine (G')

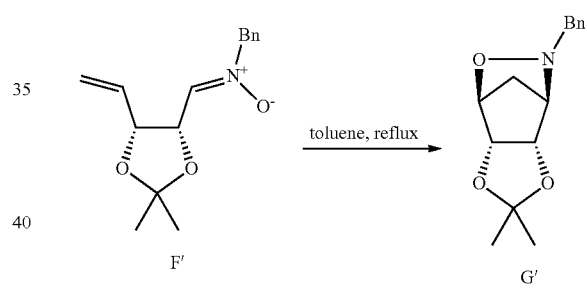

A mixture of F' (35 g) and toluene (0.70 L) was stirred at reflux temperature for 5 hours. The solution was cooled to 90° C., activated charcoal was added (5 g) and the resulting mixture was stirred at 90° C. for 10 minutes. Charcoal was filtered off and the solvent was removed under reduced pressure to give G' (34.36 g, 98%) as yellowish crystals.

Example 18

Preparation of (3aS,4S,7R,7aS)-6-benzyl-2,2-dimethyltetrahydro-3aH-4,7-methano[1,3]dioxolo[4,5-d][1,2]oxazine (G')

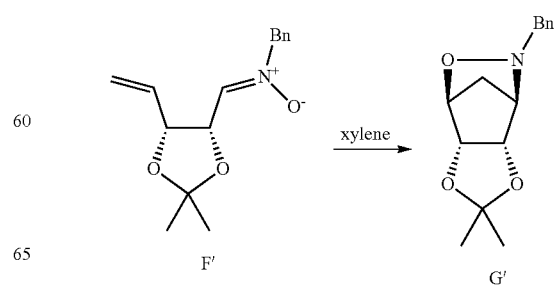

A mixture of F' (16.4 g) and xylenes (0.30 L) was stirred at 130° C. for 2 hours. The solution was cooled to 25° C., activated charcoal was added (6 g) and the resulting mixture was stirred at 25° C. for 20 minutes. Charcoal was filtered off and the solvent was removed under reduced pressure. The obtained residue was re-crystallized from 2-propanol (0.10 L) to give G' (11.9 g, 73%).

Example 19

Preparation of (3aR,4S,6R,6aS)-6-amino-2,2-dimethyltetrahydro-3aH-cyclopenta[d][1,3]dioxol-4-ol (H)

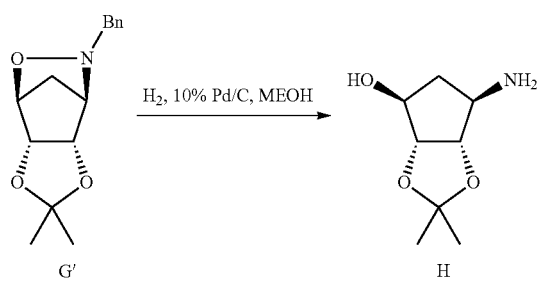

A mixture of G' (60.0 g), 10% Pd/C (6.0 g) and methanol (0.60 L) was stirred under hydrogen (3 bar) at 30° C. for 18 hours. The palladium on charcoal was removed by filtration and the solvent was removed to give H (40 g, 100%).

$^1$H NMR (CDCl$_3$): δ 1.29 (s, 3H), 1.40 (s, 3H), 1.58 (m, 1H), 1.65 (m, 1H), 2.09 (m, 1H), 3.60 (m, 1H), 4.09 (m, 1H), 4.41 (m, 1H), 4.69 (m, 1H) ppm.

Example 20

Preparation of (3aR,4S,6R,6aS)-6-(benzylamino)-2,2-dimethyltetrahydro-3aH-cyclopenta[d][1,3]dioxol-4-ol (I')

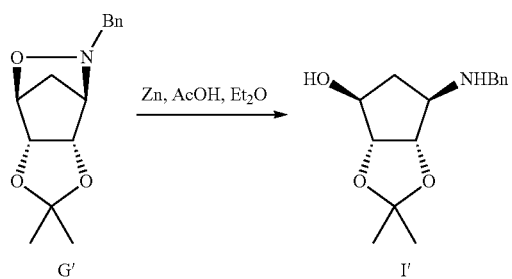

A mixture of G' (20.0 g), zinc (24.9 g) and diethyl ether (1.5 L) was cooled to 0° C. and acetic acid was added slowly during 30 min while stirring. The resulting mixture was stirred at 25° C. for 3 days and filtered through Celite. To the resulting solution was added 2 M aqueous solution of NaOH so that the pH was 7.2 and the phases were separated. The upper organic phase was washed tree times with water (3×100 mL), dried over magnesium sulfate and the solvent was removed under reduced pressure to give I' (18.0 g, 90%). $^1$H NMR (CDCl$_3$): δ 1.27 (s, 3H), 1.39 (s, 3H), 1.80 (m, 1H), 2.02 (m, 1H), 3.29 (m, 1H), 3.72 (d, 1H), 3.82 (d, 1H), 4.07 (d, 1H), 4.47 (d, 1H), 4.61 (m, 1H), 7.21-7.32 (m, 5H) ppm.

Example 21

Preparation of (3aR,4S,6R,6aS)-6-amino-2,2-dimethyltetrahydro-3aH-cyclo-penta[d][1,3]dioxol-4-ol (H)

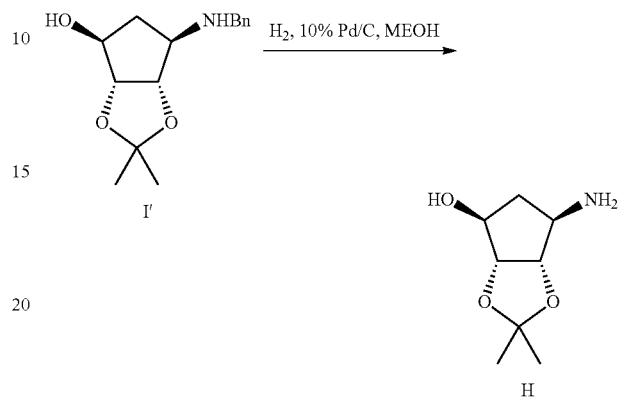

A mixture of I' (1.0 g), 10% Pd/C (0.10 g) and methanol (10 mL) was stirred under hydrogen (3 bar) at 30° C. for 5 hours. The palladium on charcoal was removed by filtration and the solvent was removed to give H (0.59 g, 88%).

Example 22

Preparation of (3aS,4R,6S,6aR)—N-Benzyl-6-(2-(benzyloxy)ethoxy)-2,2-dimethyl-tetrahydro-3aH-cyclopenta[d][1,3]dioxol-4-amine (IIIa)

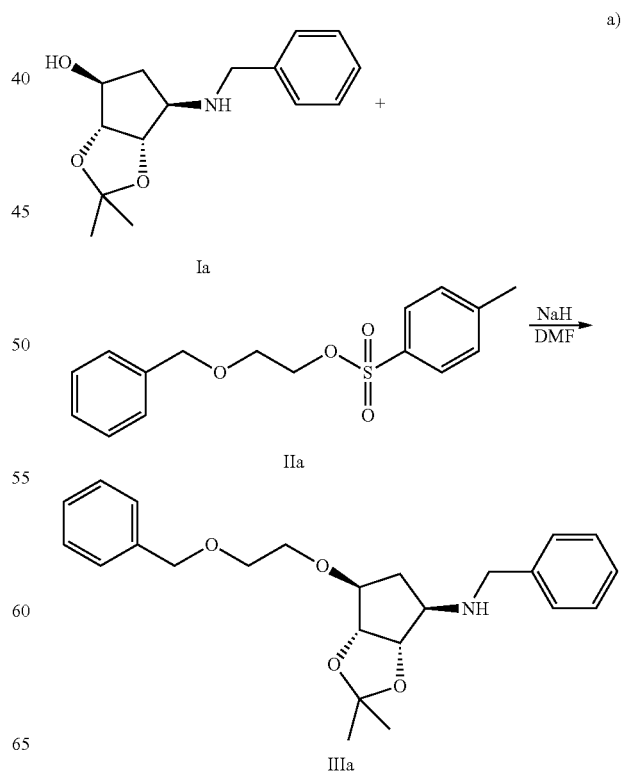

A solution of (3aR,4S,6R,6aS)-6-(benzylamino)-2,2-dimethyltetrahydro-3aH-cyclopenta-[d][1,3]-dioxol-4-ol (1.0 g, 3.8 mmol) in dry DMF (10 mL) under nitrogen atmosphere was cooled at 0° C. followed by addition of NaH (60%, 182 mg, 4.6 mmol). After stirring for 30 min at 0° C., 2-(benzyloxy)ethyl 4-methylbenzenesulfonate (1.2 g, 3.8 mmol) was added and the reaction mixture was allowed to warm at room temperature. After stirring for 4 hours, the reaction mixture was quenched with water (10 mL). To the mixture was extracted 3×10 mL of n-hexane. The combined organic phases were dried over MgSO₄, filtered and evaporated to the dryness.

b)

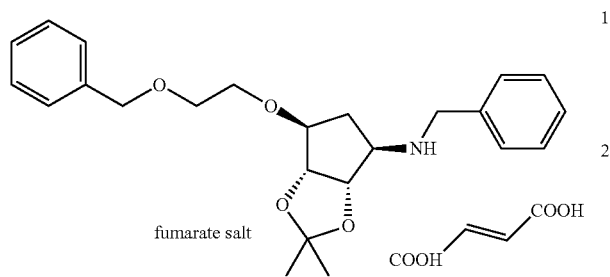

IIIa

Obtained IIIa was isolated from the reaction mixture by salt formation with fumaric acid. The solution of reaction mixture of IIIa (contained about 80% of IIIa) in 2-butanone was warmed to 50° C. 1 eq of fumaric acid (calculated to amount of IIIa) was added and reaction mixture was stirred at 50° C. until fumaric acid dissolution. The reaction mixture was allowed to cool at room temperature followed by addition of n-hexane. After overnight stirring at room temperature, the precipitate white salt of IIIa was sucked off, washed with n-hexane and dried under reduce pressure at 40° C.

c)

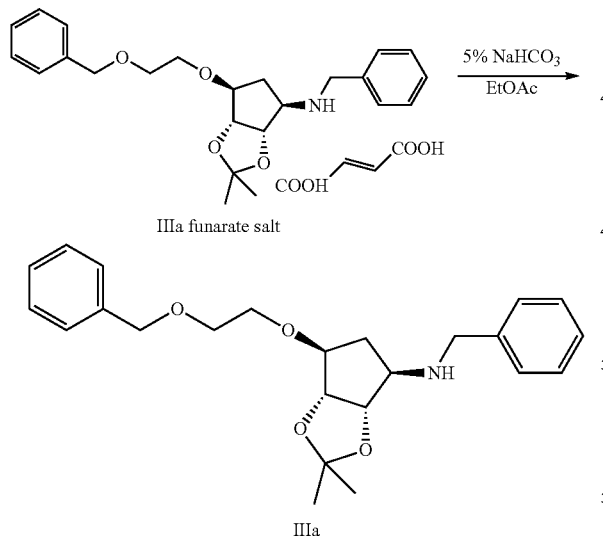

IIIa fumarate salt

IIIa

IIIa fumarate salt was suspended in EtOAc and 5% aqueous solution of NaHCO₃ was added to the suspension. The mixture was stirred vigorously at room temperature for an hour. The two clear phases were separated and organic phase was washed with water, dried over MgSO₄ and evaporated to the dryness to provide pure IIIa.

¹H NMR (CDCl₃) δ=1.30 (s, 3H), 1.40 (s, 3H), 1.90 (d, 1H), 2.15 (m, 1H), 3.17 (m, 1H), 3.60 (m, 2H), 3.68 (m, 2H), 3.80-3.90 (m, 3H), 4.51 (s, 2H), 4.63 (m, 2H), 7.23-7.36 (m, 10H) ppm.

¹³C NMR (CDCl₃) δ=24.0, 26.4, 33.9, 51.6, 63.0, 68.5, 69.2, 73.1, 83.9, 84.6, 84.8 110.4, 126.7, 127.5, 127.53, 128.0, 128.2, 128.3, 138.1, 140.3 ppm.

Example 23

Preparation of (3aS,4R,6S,6aR)—N-Benzyl-6-(2-tert-butoxy)ethoxy)-2,2-dimethyl-tetrahydro-3aH-cyclopenta[d][1,3]dioxol-4-amine (IIIb)

a)

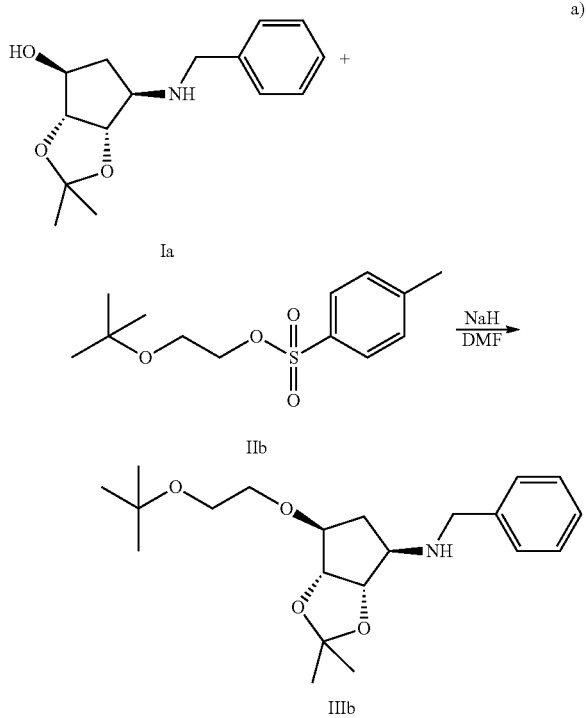

A solution of (3aR,4S,6R,6aS)-6-(benzylamino)-2,2-dimethyltetrahydro-3aH-cyclopenta-[d][1,3]-dioxol-4-ol (10 g, 38 mmol) in dry DMF (100 mL) under nitrogen atmosphere was cooled at 0° C. followed by addition of NaH (60%, 1.8 g, 46 mmol). After stirring for 30 min at 0° C., 2-(tert-butoxy)ethyl 4-methylbenzenesulfonate (10.3 g, 38 mmol) was added and the reaction mixture was allowed to warm at room temperature. After stirring for 4 hours, the reaction mixture was quenched with water (100 mL). The mixture was extracted 3×10 mL of n-hexane. The combined organic phases were dried over MgSO₄, filtered and evaporated to the dryness.

b)

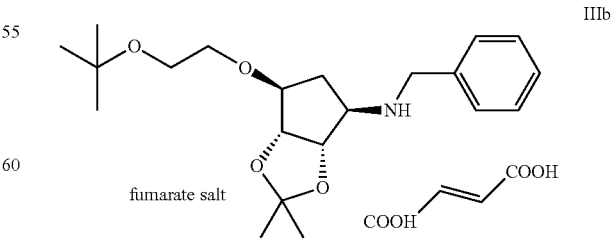

IIIb

Obtained IIIb was isolated from the reaction mixture by salt formation with fumaric acid. The solution of reaction mixture of IIIb (contained about 60% of IIa) in 2-butanone was warmed to 50° C. 1 eq of fumaric acid (calculated to amount of IIIb) was added and reaction mixture was stirred at 50° C. until fumaric acid dissolution. The reaction mixture was allowed to cooled at room temperature followed by addition of n-hexane. After overnight stirring at room temperature, the precipitate white salt of IIIb was sucked off, washed with n-hexane and dried under reduce pressure at 40° C.

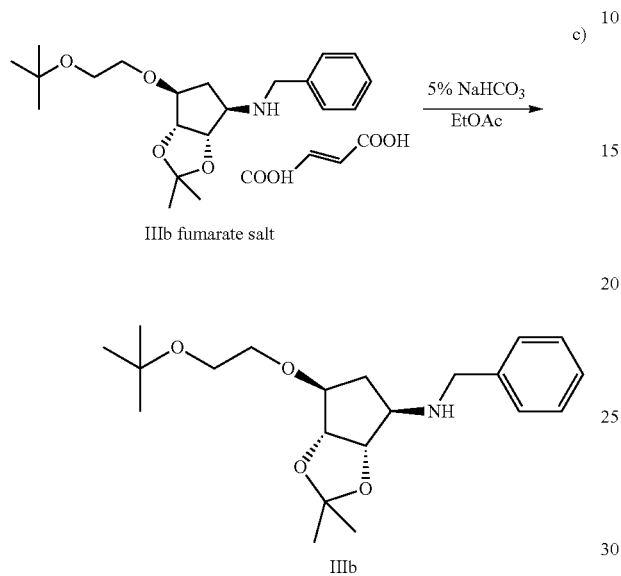

IIb fumarate salt was suspended in EtOAc and 5% aqueous solution of NaHCO3 was added to the suspension. The mixture was stirred vigorously at room temperature for an hour. The two clear phases were separated and organic phase was washed with water, dried over MgSO4 and evaporated to the dryness to provide pure IIIb.

$^1$H NMR (CDCl$_3$) δ=1.14 (s, 9H), 1.30 (s, 3H), 1.40 (s, 3H), 1.88 (d, 1H), 2.10 (m, 1H), 3.14 (m, 1H), 3.45 (m, 2H), 3.59 (m, 2H), 3.80-3.90 (m, 3H), 4.62 (m, 2H), 7.22-7.35 (m, 5H) ppm.

$^{13}$C NMR (CDCl$_3$) δ=24.0, 26.4, 27.4, 33.8, 51.7, 60.1, 63.1, 69.1, 72.9, 83.9, 84.6, 84.8 110.2, 126.7, 128.1, 128.2, 140.3 ppm.

Example 24

Preparation of tert-Butyl ((3aS,4R,6S,6aR)-6-(2-(benzyloxy)ethoxy)-2,2-dimethyl-tetrahydro-3aH-cyclopenta[d][1,3]dioxol-4-yl)carbamate (IIIc)

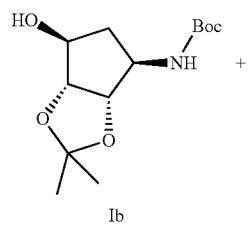

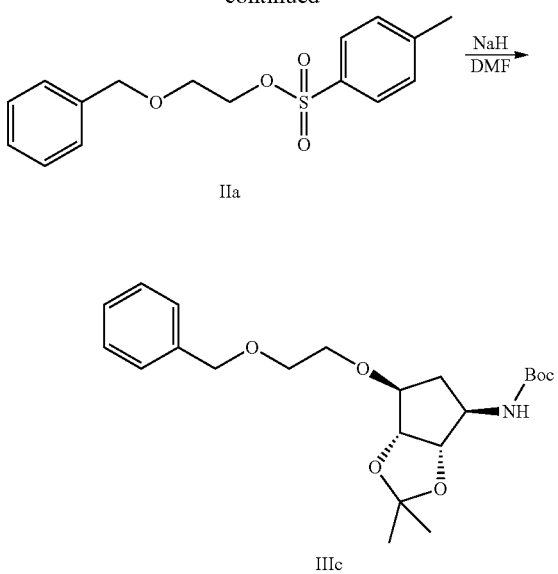

A solution of tert-butyl ((3aS,4R,6S,6aR)-6-hydroxy-2,2-dimethyltetrahydro-3aH-cyclopenta[d]-[1,3]dioxol-4-yl) carbamate (3.0 g, 10.8 mmol) in dry DMF (30 mL) under nitrogen atmosphere was cooled at 0° C. followed by addition of NaH (60%, 530 mg, 13.0 mmol). After stirring for 30 min at 0° C., 2-(benzyloxy)ethyl 4-methylbenzenesulfonate (3.3 g, 10.8 mmol) was added and the reaction mixture was allowed to warm at room temperature. After stirring for 4 hours, the reaction mixture was quenched with water (30 mL). To the mixture was extracted 3×30 mL of n-hexane. The combined organic phases were dried over MgSO$_4$, filtered and evaporated to the dryness. The pure IIIc was isolated from reaction mixture by chromatography on silica gel column (mobile phase: n-hexane/EtOAc).

$^1$H NMR (CDCl$_3$) δ=1.30 (s, 3H), 1.40 (s, 12H), 1.82 (d, 1H), 2.14 (m, 1H), 3.53-3.67 (m, 4H), 3.87 (d, 1H), 4.11 (m, 1H), 4.49-4.58 (m, 3H), 4.65 (m, 1H), 5.73 (d, 1H), 7.27-7.36 (m, 5H) ppm.

$^{13}$C NMR (CDCl$_3$) δ=23.8, 26.2, 28.4, 32.3, 56.4, 68.0, 68.8, 73.2, 79.0, 83.5, 84.9, 86.0, 110.1, 127.7, 128.4, 138.0, 155.2 ppm.

Example 25

Preparation of tert-Butyl ((3aS,4R,6S,6aR)-6-(2-(tert-butoxy)ethoxy)-2,2-dimethyl-tetrahydro-3aH-cyclopenta[d][1,3]dioxol-4-yl)carbamate (IIId)

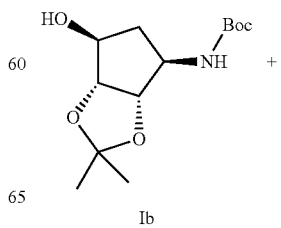

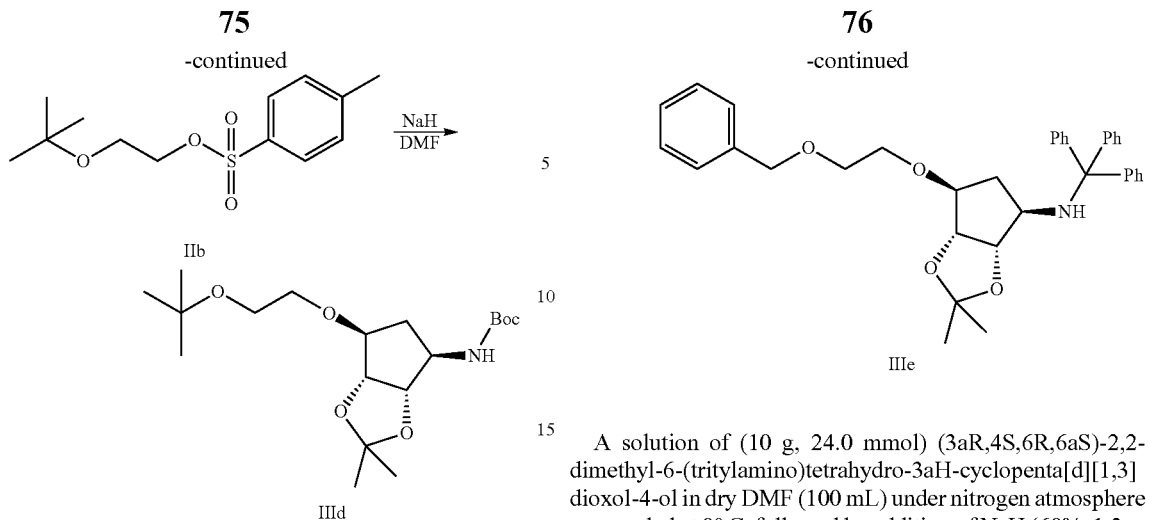

A solution of tert-butyl ((3aS,4R,6S,6aR)-6-hydroxy-2,2-dimethyltetrahydro-3aH-cyclopenta-[d][1,3]dioxol-4-yl)carbamate (7.0 g, 25.6 mmol) in dry DMF (70 mL) under nitrogen atmosphere was cooled at 0° C. followed by addition of NaH (60%, 1.3 g, 30.7 mmol). After stirring for 30 min at 0° C., 2-(tert-butoxy)ethyl 4-methylbenzenesulfonate (7.0 g, 25.6 mmol) was added and the reaction mixture was allowed to warm at room temperature. After stirring for 4 hours, the reaction mixture was quenched with water (70 mL). To the mixture was extracted 3×100 mL of n-hexane. The combined organic phases were dried over MgSO₄, filtered and evaporated to the dryness. The pure IIId was isolated from reaction mixture by chromatography on silica gel column (mobile phase: n-hexane/EtOAc).

¹H NMR (CDCl₃) δ=1.21 (s, 9H), 1.26 (s, 3H), 1.40 (s, 3H), 1.43 (s, 9H), 1.78 (d, 1H), 2.15 (m, 1H), 3.47-3.57 (m, 3H), 3.65 (m, 1H), 3.83 (m, 1H), 4.10 (m, 1H), 4.50 (m, 2H), 4.60 (m, 1H), 5.50 (d, 1H) ppm.

¹³C NMR (CDCl₃) δ=23.8, 26.2, 27.5, 32.7, 56.5, 60.9, 69.2, 73.0, 83.3, 85.1, 86.0, 110.0, 128.0, 129.7, 155.2 ppm.

Example 26

(3aS,4R,6S,6aR)-6-(2-(benzyloxy)ethoxy)-2,2-dimethyl-N-tritytetrahydro-3aH-cyclopenta[d][1,3]dioxol-4-amine (IIIe)

A solution of (10 g, 24.0 mmol) (3aR,4S,6R,6aS)-2,2-dimethyl-6-(tritylamino)tetrahydro-3aH-cyclopenta[d][1,3]dioxol-4-ol in dry DMF (100 mL) under nitrogen atmosphere was cooled at 0° C. followed by addition of NaH (60%, 1.2 g, 29.0 mmol). After stirring for 30 min at 0° C., 2-(benzyloxy)ethyl 4-methylbenzenesulfonate (7.4 g, 24.0 mmol) was added and the reaction mixture was allowed to warm at room temperature. After stirring for 4 hours, the reaction mixture was quenched with water (100 mL). To the mixture was extracted 3×100 mL of EtOAc. The combined organic phases were dried over MgSO₄, filtered and evaporated to the dryness. The pure IIIe was isolated from reaction mixture by chromatography on silica gel column (mobile phase: n-hexane/EtOAc).

¹H NMR (CDCl₃) δ=0.57 (d, 1H), 1.20 (s, 3H), 1.30 (s, 3H), 1.45 (m, 1H), 2.50 (s, 1H), 3.15 (5, 1H), 3.41 (m, 4H), 3.57 (m, 1H), 4.55 (s, 2H), 7.19 (m, 3H), 7.26-7.39 (m, 7H), 7.56 (d, 6H) ppm.

¹³C NMR (CDCl₃) δ=23.8, 26.2, 27.3, 32.5, 59.3, 61.0, 68.8, 71.5, 72.8, 83.7, 85.2, 87.6, 109.4, 126.1, 127.2, 127.8, 128.3, 128.6, 128.7, 146.9 ppm.

Example 27

Preparation of (3aS,4R,6S,6aR)-6-(2-(tert-butoxy)ethoxy)-2,2-dimethyl-N-tritytetrahydro-3aH-cyclopenta[d][1,3]dioxol-4-amine (IIIf)

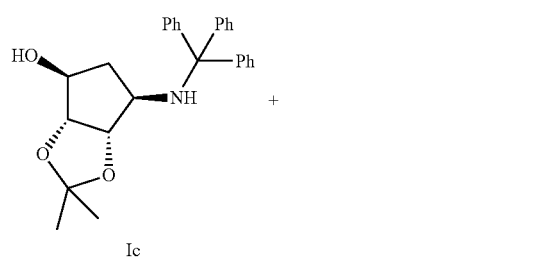

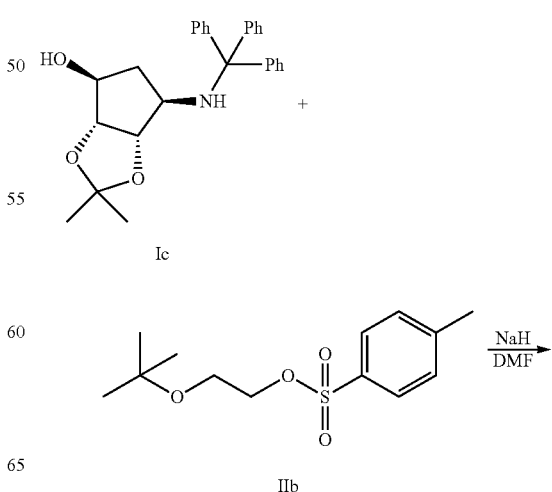

-continued

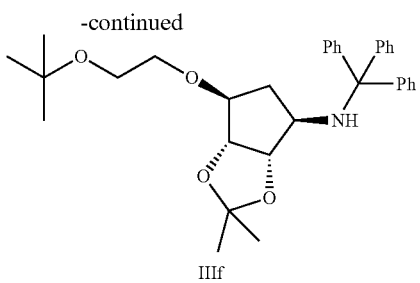

IIIf

A solution of (3aR,4S,6R,6aS)-2,2-dimethyl-6-(tritylamino)tetrahydro-3aH-cyclopenta[d]-[1,3]dioxol-4-ol (10.0 g, 24.0 mmol) in dry DMF (100 mL) under nitrogen atmosphere was cooled at 0° C. followed by addition of NaH (60%, 1.2 g, 29.0 mmol). After stirring for 30 min at 0° C., 2-(tert-butoxy)ethyl 4-methylbenzenesulfonate (6.5 g, 24.0 mmol) was added and the reaction mixture was allowed to warm at room temperature. After stirring for 4 hours, the reaction mixture was quenched with water (100 mL). To the mixture was extracted 3×100 mL of EtOAc. The combined organic phases were dried over MgSO4, filtered and evaporated to the dryness. The pure IIIf was isolated from reaction mixture by chromatography on silica gel column (mobile phase: n-hexane/EtOAc).

1H NMR (CDCl$_3$) δ=0.57 (d, 1H), 1.20 (s, 9H), 1.30 (s, 3H), 1.35 (s, 3H), 1.45 (m, 1H), 2.50 (5, 1H), 3.15 (s, 1H), 3.41 (m, 4H), 3.57 (m, 1H), 4.55 (s, 2H), 7.19 (m, 3H), 7.26-7.39 (m, 7H), 7.56 (d, 6H) ppm.

13C NMR (CDCl$_3$) δ=23.8, 26.2, 27.3, 32.5, 59.3, 61.0, 68.8, 71.5, 72.8, 83.7, 85.2, 87.6, 109.4, 126.1, 127.2, 127.8, 128.3, 128.6, 128.7, 146.9 ppm.

Example 28

Preparation of (1S,2S,3R,5S)-3-(Benzylamino)-5-(2-(benzyloxy)ethoxy)cyclo-pentane-1,2-diol (IVa)

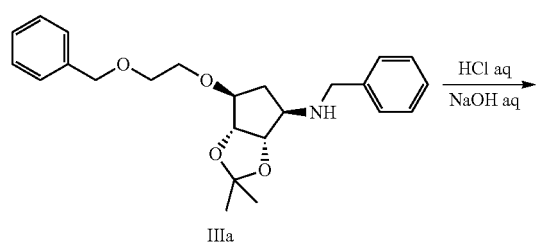

IIIa

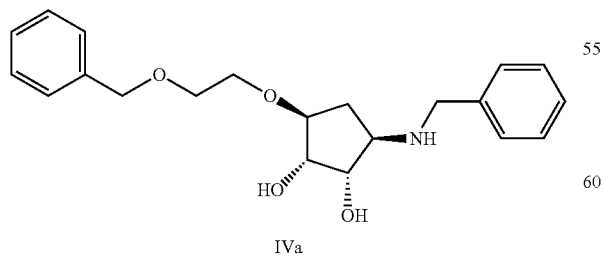

IVa

IIIa (2.0 g, 5 mmol) was treated with 1M HCl (20 mL) at room temperature for 7 hours followed by addition of 1M NaOH (25 mL). The reaction mixture was extracted with 30 mL of EtOAc. Organic phase was washed with water, dried over MgSO4 and evaporated to the dryness to provide IVa.

1H NMR (CDCl$_3$) δ=1.34 (m, 1H), 2.44 (m, 1H), 3.02 (m, 1H), 3.60-3.87 (m, 8H), 4.0 (m, 1H), 4.56 (s, 2H), 7.27-7.37 (m, 10H) ppm.

13C NMR (CDCl$_3$) δ=34.6, 52.3, 61.3, 69.3, 69.8, 73.3, 75.5, 76.2, 83.8, 127.1, 127.8, 128.2, 128.5, 128.6, 137.9, 140.0 ppm.

Example 29

Preparation of (1S,2S,3R,5S)-3-Amino-5-(2-hydroxyethoxy)cyclopentane-1,2-diol (VI)

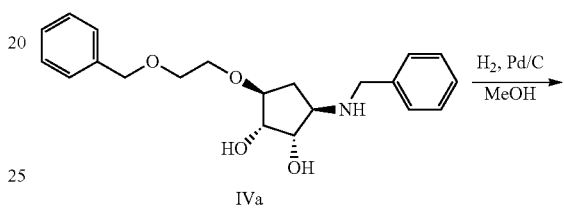

IVa

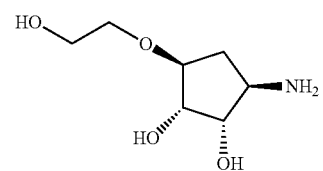

VI

The solution of IVa (1.1 g, 2.8 mmol) in MeOH (15 mL) was hydrogenated at 10 bar of hydrogen for 16 hours in the presence of Pd/C (10%, 0.2 g). The reaction mixture was passed through the pad of celite and evaporated to the dryness to provide VI.

1H NMR (DMSO-d$_6$) δ=1.07 (m, 1H), 2.19 (m, 1H), 2.90 (m, 1H), 3.36-3.60 (m, 6H), 3.74 (m, 1H) ppm.

13C NMR (DMSO-d$_6$) δ=36.4, 55.0, 60.4, 70.7, 75.1, 78.7, 83.4 ppm.

Example 30

Preparation of (3aS,4R,6S,6aR)-6-(2-(tert-butoxy)ethoxy)-2,2-dimethyltetrahydro-3aH-cyclopenta[d][1,3]dioxol-4-amine (Va)

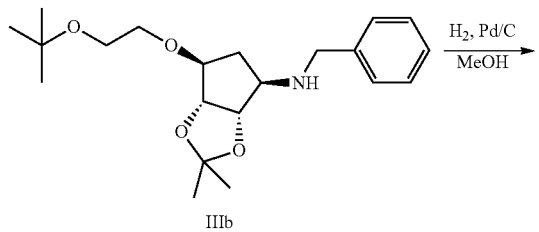

IIIb

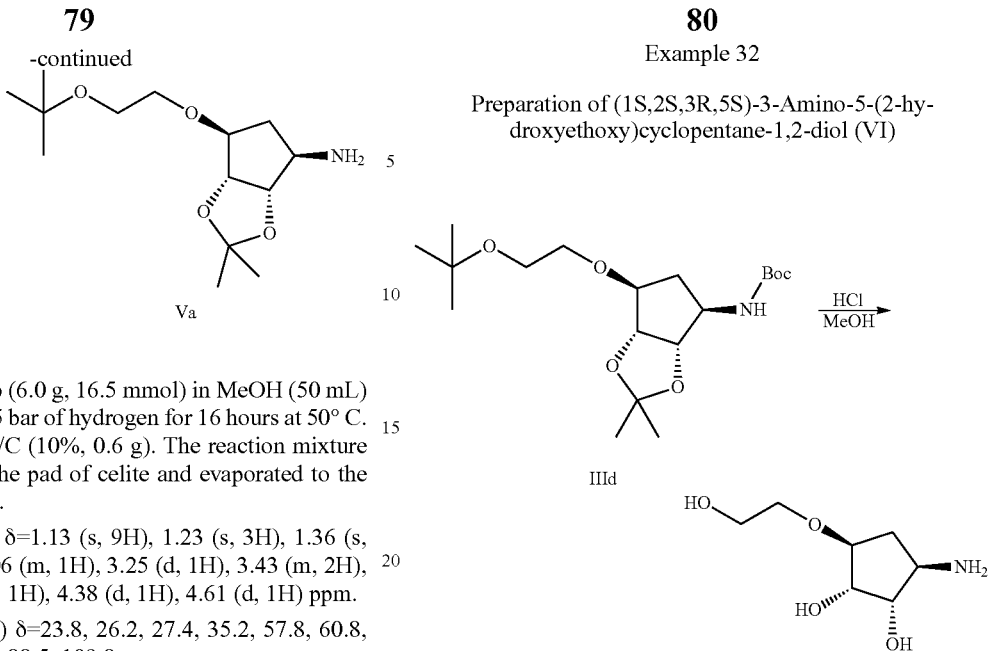

The solution of IIIb (6.0 g, 16.5 mmol) in MeOH (50 mL) was hydrogenated at 5 bar of hydrogen for 16 hours at 50° C. in the presence of Pd/C (10%, 0.6 g). The reaction mixture was passed through the pad of celite and evaporated to the dryness to provide Va.

1H NMR (CDCl$_3$) δ=1.13 (s, 9H), 1.23 (s, 3H), 1.36 (s, 3H), 1.74 (d, 1H), 2.06 (m, 1H), 3.25 (d, 1H), 3.43 (m, 2H), 3.55 (m, 2H), 3.81 (d, 1H), 4.38 (d, 1H), 4.61 (d, 1H) ppm.

13C NMR (CDCl$_3$) δ=23.8, 26.2, 27.4, 35.2, 57.8, 60.8, 68.8, 72.8, 84.0, 85.1, 88.5, 109.8 ppm.

Example 31

Preparation of (1S,2S,3S,5R)-3-(2-(benzyloxy)ethoxy)-5-(tritylamino)cyclo-pentane-1,2-diol (IVb)

IIIe (1.0 g, 1.8 mmol) was treated with konc. HCl (0.5 mL) in THF (5 mL) at room temperature for 7 hours followed by addition of 8M NaOH (pH=8). The reaction mixture was extracted with 20 mL of EtOAc. Organic phase was washed with water, dried over MgSO$_4$ and evaporated to the dryness to provide IVb.

1H NMR (CDCl$_3$) δ=0.85 (m, 1H), 1.62 (m, 1 h), 2.8 (s, 1H), 2.94 (m, 1H), 3.47 (m, 1H), 3.56 (m, 4H), 3.77 (s, 1H9, 3.90 (m, 1H), 4.53 (s, 1H), 7.20 (m, 3H) 7.28 (m, 11H), 7.56 (d, 6H) ppm.

13C NMR (CDCl$_3$) δ=36.2, 57.5, 60.4, 69.0, 70.0, 73.2, 75.2, 78.6, 83.4, 126.4, 127.7, 127.73, 127.9, 128.4, 128.8, 146.7 ppm.

Example 32

Preparation of (1S,2S,3R,5S)-3-Amino-5-(2-hydroxyethoxy)cyclopentane-1,2-diol (VI)

IIId (4.4 g, 11.8 mmol) was treated with conc. HCl (5 mL) in MeOH (20 mL) at reflux for 16 hours. MeOH was removed by evaporation and 10 mL of water was added to the residue. The mixture was washed with EtOAc (20 mL) followed by addition of 2M NaOH (pH=9). Water was removed by evaporation and 30 mL of i-PrOH was added to the residue. After filtration, i-PrOH was removed under reduce pressure to provide VI.

1H NMR (D$_2$O) δ=1.52 (m, 1H), 2.58 (m, 1H), 3.33 (m, 1H), 3.55-3.62 (m, 4H), 3.79 (m, 1H), 3.99 (m, 1H), 4.09 (m, 1H) ppm.

13C NMR (D$_2$O) δ=31.5, 53.9, 60.6, 70.5, 73.9, 74.2, 81.9 ppm.

Example 33

Preparation of (1S,2S,3R,5S)-3-Amino-5-(2-hydroxyethoxy)cyclopentane-1,2-diol (VI)

IIIf (1.0 g, 1.9 mmol) was treated with conc. HCl (2 mL) in MeOH (5 mL) at reflux for 16 hours. MeOH was removed by evaporation and 10 mL of water was added to the residue. The mixture was washed with EtOAc (10 mL) followed by addition of 2M NaOH (pH=9). Water was removed by evaporation and 10 mL of i-PrOH was added to the residue. After filtration, i-PrOH was removed under reduce pressure to provide VI.

1H NMR (D$_2$O) δ=1.35 (m, 1H), 2.51 (m, 1H), 3.22 (m, 1H), 3.60-3.65 (m, 4H), 3.79 (m, 1H), 3.85 (m, 1H), 3.99 (m, 1H) ppm.

13C NMR (D$_2$O) δ=33.5, 53.9, 60.6, 70.5, 74.5, 76.1, 82.5 ppm.

Example 34

Preparation of benzyl N-((1S,4R)-4-(2-(benzyloxy)ethoxy)cyclopent-2-en-1-yl)-N-(hydroxy)carbamate (K')

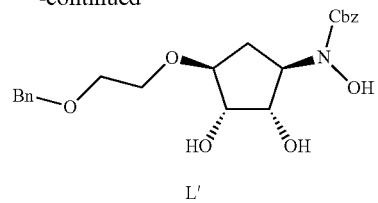

A mixture of J' (8.16 g), CuCl$_2$ (4.7 g), 2-benzyloxyethanol (21.4 g) and toluene (320 mL) was stirred at 25° C. for 16 hours, afterwards a saturated aqueous solution of EDTA disodium salt was added. The two phases were separated and the water phase was re-extracted with toluene (80 mL). The combined toluene phases were dried over sodium sulfate, filtered and the solvent was removed under reduced pressure. The mixture was purified by chromatography (silica gel; dichloromethane:ethyl acetate=100:0→0:100) to give K' together with some 2-benzyloxyethanol (14 g). The product was used in the next step without further purification.

$^1$H NMR (CDCl$_3$): d 1.97 (m, 1H), 2.50 (m, 1H), 3.60 (m, 2H), 3.67 (m, 2H), 4.48 (m, 1H), 4.54 (m, 2H), 5.14 (m, 1H), 5.19 (s, 2H), 5.86 (m, 1H), 6.07 (m, 1H), 7.34 (m, 10H).

Example 35

Preparation of benzyl N-((1S,2R,3R,4R)-4-(2-(benzyloxy)ethoxy)-2,3-dihydroxy cyclopentyl)-N-hydroxycarbamate (L')

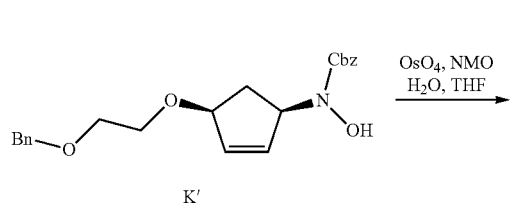

A mixture of K' (14 g; from Example 34), N-methylmorpholine N-oxide (3.0 g), osmium tetroxide (4% in water, 3 mL) water (20 mL) and tetrahydrofuran (200 mL) was stirred at 25° C. for 40 hours. The two phases were separated and the water phase was re-extracted with tetrahydrofuran (100 mL). The tetrahydrofuran phases were combined and the solvent was removed. The product was purified by chromatography (silica gel; dichloromethane-ethyl acetate=70:30→0:100) to give L' (3 g) as an oil. $^1$H NMR (CD$_3$OD): δ 1.74 (m, 1H), 2.26 (m, 1H), 3.62 (m, 2H); 3.67 (m, 2H), 3.72 (m, 1H), 3.90 (m, 1H), 4.20 (m, 1H), 4.50 (m, 1H), 4.55 (s, 2H), 5.17 (m, 2H), 7.33 (m, 10H).

Example 36

Preparation of (1S,2S,3R,5S)-3-Amino-5-(2-hydroxyethoxy)cyclopentane-1,2-diol (VI)

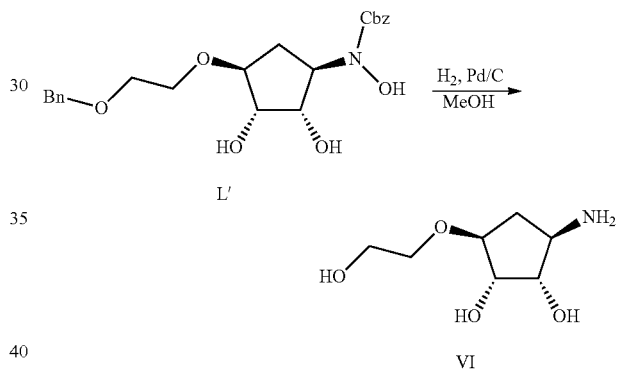

A solution of L' (0.5 g), 5% Pd/C (0.5 g), water (1 mL), acetic acid (0.5 mL) and methanol (20 mL) was stirred under hydrogen atmosphere (10 bar) at 35° C. for 64 hours. The reaction mixture was filtered through Celite® and the solvents were removed under reduced pressure to give VI (OLA) (0.28 g) as an oil. $^1$H NMR (DMSO-d$_6$): δ 1.07 (m, 1H), 2.19 (m, 1H), 2.87 (dd, J=14.7, 7.8 Hz, 1H), 3.00-3.60 (m, 10H), 3.53 (m, 1H), 3.74 (dd, J=5.4, 3.4, 1H). $^{13}$C NMR (DMSO-d$_6$): d 36.4, 55.0, 60.4, 70.7, 75.1, 78.7, 83.3. MS (ESI) m/z: 178 [MH]$^+$.

Example 37

Preparation of (1S,2S,3R,5S)-3-((5-amino-6-chloro-2-(propylthio)pyrimidin-4-yl)-amino)-5-(2-hydroxyethoxy)cyclopentane-1,2-diol (OLACINA)

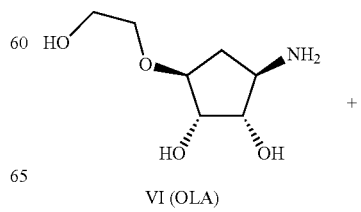

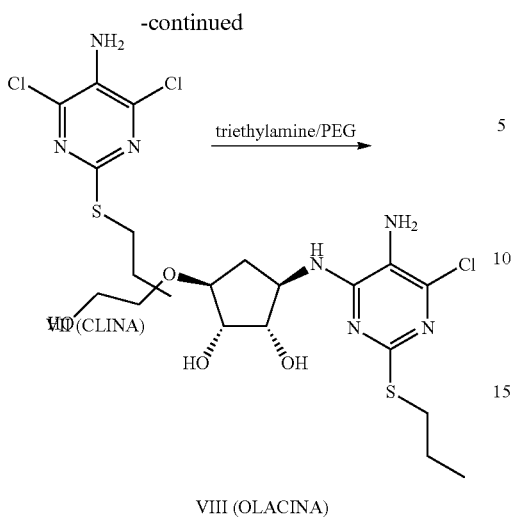

VIII (OLACINA)

A mixture of (1S,2S,3R,5S)-3-amino-5-(2-hydroxyethoxy)cyclopentane-1,2-diol (OLA; 1.06 g, 6 mmol), 4,6-dichloro-2-(propylthio)pyrimidin-5-amine (CLINA; 1.43 g, 6 mmol), triethylamine (1.09 g, 7.8 mmol) and polyethyleneglycol PEG400 (2 mL) was stirred for 48 h at 75° C. The reaction mixture was diluted with ethyl acetate (50 mL), washed with water (25 mL) and evaporated under reduced pressure to give a resinous material which solidified upon trituration in n-hexane (25 mL). After filtration there was obtained OLACINA as a grey powder (2.0 g, 88% yield): $^{13}$C NMR (DMSO-d$_6$, 125 MHz) δ13.3, 22.8, 32.2, 34.7, 54.8, 60.4, 69.8, 72.4, 75.2, 82.4, 119.9, 137.5, 152.5, 155.1.

Example 38

Preparation of (1S,2S,3R,5S)-3-(7-chloro-5-(propylthio)-3H-[1,2,3]triazolo[4,5-d]pyrimidin-3-yl)-5-(2-hydroxyethoxy)cyclopentane-1,2-diol (CLTOL)

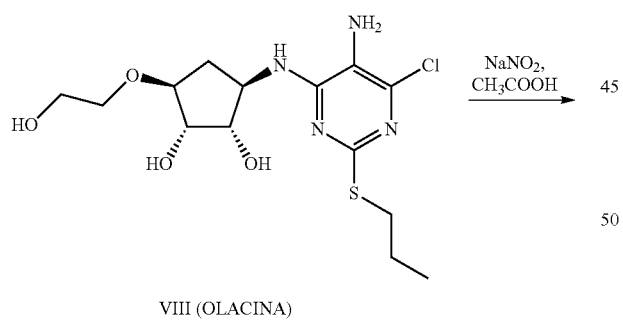

VIII (OLACINA)

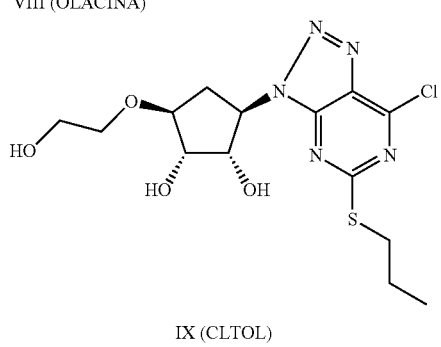

IX (CLTOL)

To a stirring solution of (1S,2S,3R,5S)-3-((5-amino-6-chloro-2-(propylthio)pyrimidin-4-yl)amino)-5-(2-hydroxyethoxy)cyclopentane-1,2-diol (OLACINA; 1.14 g, 3 mmol) in acetic acid (5 mL) was added sodium nitrite (0.23 g, 3.3 mmol) while maintaining the reaction temperature at 20-30° C. The reaction mixture was stirred for 30 minutes. It was then diluted with ethyl acetate (50 mL), washed with water (2×35 mL) and evaporated under reduced pressure. The crude product was triturated in hexane (20 mL) and filtered to give CLTOL as an off-white powder (1.00 g, 86% yield): 98 area % by HPLC; mp 98-107° C.; $^{13}$C NMR (CDCl$_3$, 125 MHz) δ13.4, 22.0, 33.5, 33.7, 61.75, 61.77, 71.1, 74.9, 75.4, 82.0, 131.8, 150.7, 152.9, 171.8.

Example 39

(1S,2S,3R,5S)-3-(7-hydroxy-5-(propylthio)-3H-[1,2,3]triazolo[4,5-d]pyrimidin-3-yl)-5-(2-hydroxyethoxy)cyclopentane-1,2-diol (OHTOL)

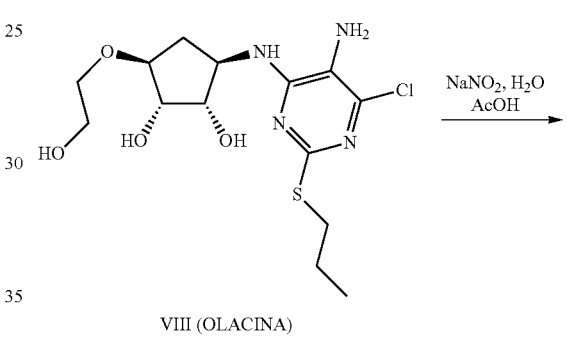

VIII (OLACINA)

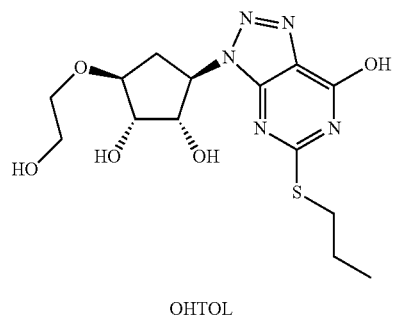

OHTOL

To a mixture of OLACINA (20.0 g) in acetic acid (50 g) and water (25 g) is added 4 M aqueous NaNO$_2$ (39.6 mL) during 16 hours at 25° C. The resulting mixture is stirred for additional 4 hours at 25° C. Solvents were removed under reduced pressure, water (100 mL) was added and the solvents were again removed under reduced pressure (bath temperature 60° C.). Water (100 mL) was added and removed under reduced pressure for the second time. Water was added (100 mL), heated to 60° C. and slowly cooled to 25° C. The precipitate was filtered off, washed with water (100 mL), ethyl acetate (4×10 mL) and dried under reduced pressure to give OHTOL (16.4 g). $^1$H NMR (DMSO-d$_6$): δ 0.97 (m, 3H), 1.70 (m, 2H), 2.04 (m, 1H), 2.65 (m, 1H), 3.17 (m, 2H), 3.48 (m, 4H), 3.74 (m, 1H), 3.93 (m, 1H), 4.56 (m, 1H), 4.95 (m, 1H), 12.86 (m, 1H). $^{13}$C NMR (DMSO-d$_6$): δ 13.1, 22.0, 32.2, 33.2, 60.3, 61.4, 70.9, 73.7, 74.3, 81.7, 127.7, 148.6, 155.5, 161.6.

Example 40

Preparation of (1S,2S,3R,5S)-3-(7-chloro-5-(propylthio)-3H-[1,2,3]triazolo[4,5-d]pyrimidin-3-yl)-5-(2-hydroxyethoxy)cyclopentane-1,2-diol (CLTOL)

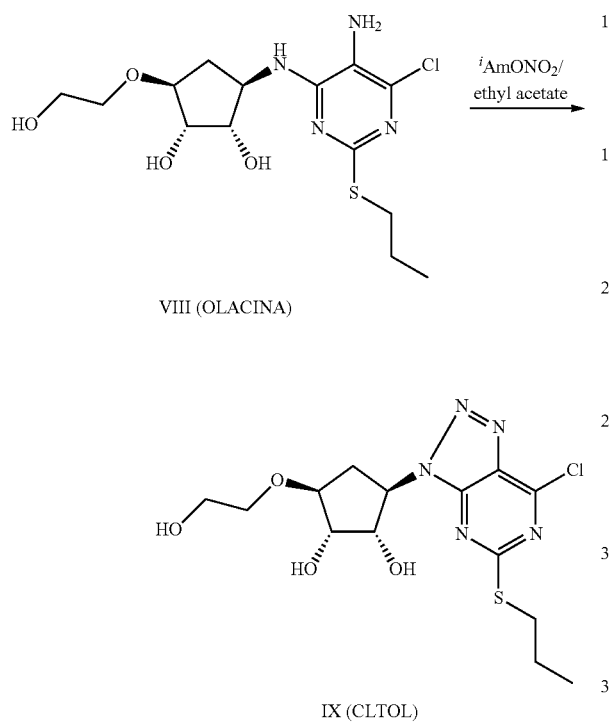

To a stirring solution of (1S,2S,3R,5S)-3-((5-amino-6-chloro-2-(propylthio)pyrimidin-4-yl)amino)-5-(2-hydroxyethoxy)cyclopentane-1,2-diol (OLACINA; 0.38 g, 1 mmol) in ethyl acetate (7 mL) was added isopentyl nitrite (0.16 mL, 1.2 mmol). The reaction mixture was stirred for 1 h at 65° C. and then evaporated under reduced pressure to give a reddish powder which was recrystallized from a mixture of methyl tert-butyl ether/n-hexane to give CLTOL as a crystalline product (0.31 g, 80% yield): 99 area % by HPLC.

Example 41

Preparation of (1S,2S,3R,5S)-3-(7-chloro-5-(propylthio)-3H-[1,2,3]triazolo[4,5-d]pyrimidin-3-yl)-5-(2-hydroxyethoxy)cyclopentane-1,2-diol (CLTOL)

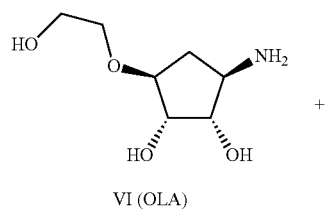

VI (OLA)
+

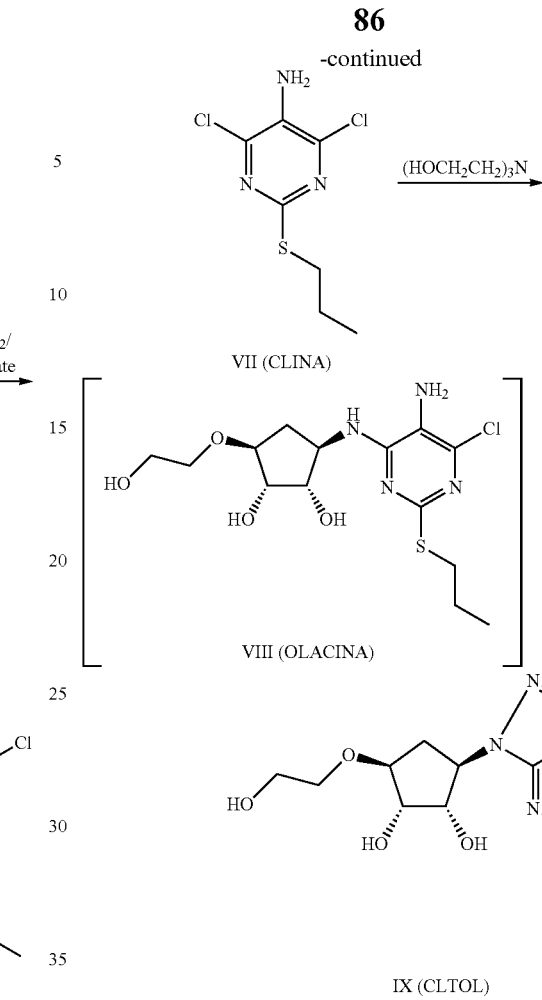

A mixture of (1S,2S,3R,5S)-3-amino-5-(2-hydroxyethoxy)cyclopentane-1,2-diol (OLA; 0.89 g, 5 mmol), 4,6-dichloro-2-(propylthio)pyrimidin-5-amine (CLINA; 1.19 g, 5 mmol) and triethanolamine (1.49 g, 10 mmol) was stirred neat for 24 h at 90° C. After cooling to ambient temperature, the viscous reaction mixture was dissolved by the addition of acetic acid (3 mL). While maintaining the reaction temperature at 15-20° C. there was added sodium nitrite (0.38 g, 5.5 mmol) and the reaction mixture left stirring for 12 h. The reaction mixture was diluted with ethyl acetate (35 mL), washed with water (2×25 mL) and evaporated under reduced pressure. The crude product was triturated in hexane (20 mL) and filtered to give CLTOL as an off-white powder (1.61 g, 83% yield): $^{13}$C NMR (CDCl$_3$, 125 MHz) δ13.4, 22.0, 33.5, 33.7, 61.75, 61.77, 71.1, 74.9, 75.4, 82.0, 131.8, 150.7, 152.9, 171.8.

Example 42

Preparation of (1S,2S,3R,5S)-3-((6-chloro-5-nitro-2-(propylthio)pyrimidin-4-yl)amino)-5-(2-hydroxyethoxy)cyclopentane-1,2-diol (OLACIN)

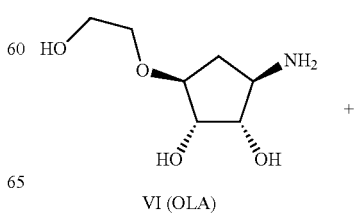

VI (OLA)
+

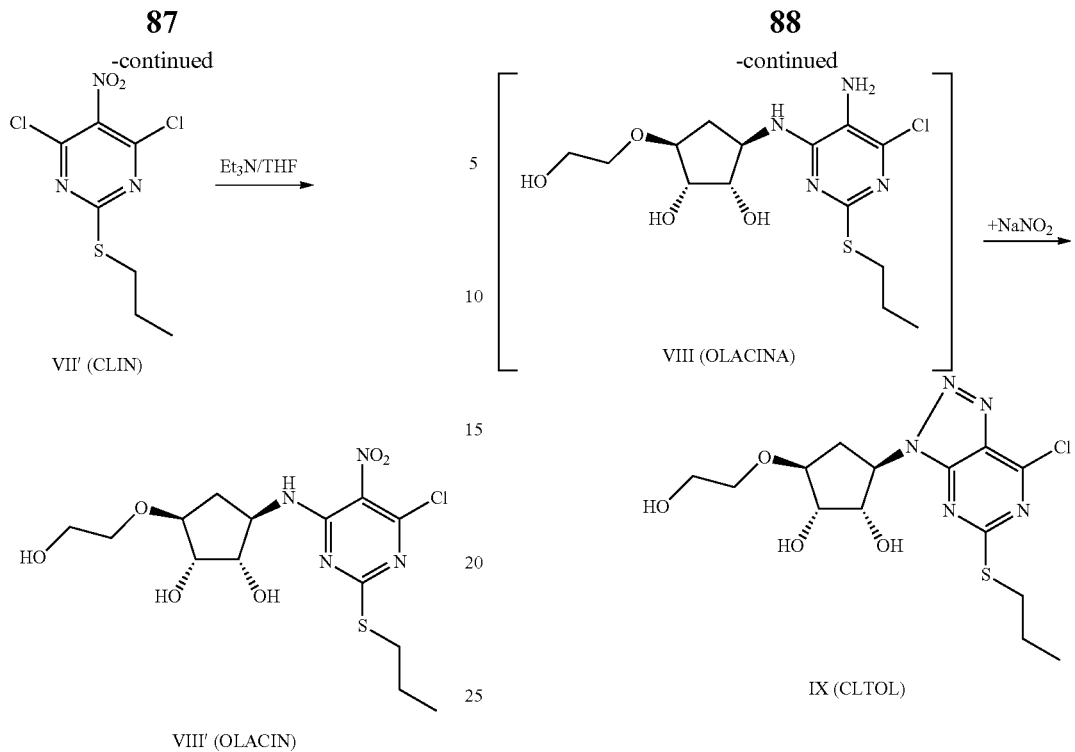

VII' (CLIN)

VIII' (OLACIN)

VIII (OLACINA)

IX (CLTOL)

To a stirring solution of 4,6-dichloro-5-nitro-2-(propylthio)pyrimidine (CLIN; 0.80 g, 3 mmol) in tetrahydrofuran (30 mL) at 0° C. was slowly added a solution of (1S,2S,3R,5S)-3-amino-5-(2-hydroxyethoxy)cyclopentane-1,2-diol (OLA; 0.53 g, 3 mmol) in N-methylpyrrolidin-2-one (5 mL). After 10 min there was added triethylamine (0.42 mL, 3 mmol) and the mixture left stirring for 3 h at 0° C. and then 16 h at 20° C. The reaction mixture was diluted with ethyl acetate (60 mL), washed with water (2×60 mL) and evaporated under reduced pressure. The obtained crude product was triturated under diisopropyl ether (10 mL) and filtered to give OLACIN as a yellow powder (0.86 g, 70% yield): 98 area % by HPLC; mp 94-98° C.; $^{13}$C NMR (CDCl$_3$, 125 MHz) δ13.2, 22.3, 32.7, 33.6, 55.7, 60.3, 70.7, 74.0, 74.6, 82.5, 124.5, 151.6, 153.9, 171.9.

Example 43

Preparation of (1S,2S,3R,5S)-3-(7-chloro-5-(propylthio)-3H-[1,2,3]triazolo[4,5-d]pyrimidin-3-yl)-5-(2-hydroxyethoxy)cyclopentane-1,2-diol (CLTOL)

The solution of (1S,2S,3R,5S)-3-((6-chloro-5-nitro-2-(propylthio)pyrimidin-4-yl)amino)-5-(2-hydroxyethoxy)cyclopentane-1,2-diol (OLACIN; 0.74 g, 1.8 mmol) in acetic acid (15 mL) was hydrogenated for 5 h in the presence of platinum on carbon (5%; 0.11 g, 1.5 mol %) at 10 bar hydrogen pressure. The catalyst was filtered trough celite and washed with ethyl acetate (5 mL). The analysis of the filtrate confirmed complete conversion of the starting material and 95 area % HPLC purity of the intermediate (1S,2S,3R,5S)-3-((5-amino-6-chloro-2-(propylthio)pyrimidin-4-yl)amino)-5-(2-hydroxyethoxy)cyclopentane-1,2-diol (OLACINA). To the filtrate was then added sodium nitrite (0.14 g, 2 mmol) while stirring in a bath at 15-20° C. After 1 h, the reaction mixture was diluted with ethyl acetate (50 mL), washed with water (2×50 mL) and evaporated under reduced pressure. The solid residue was triturated in n-hexane (10 mL) and filtered to give CLTOL as a grey powder (0.50 g, 71% yield): 96 area % by HPLC; mp 91-95° C.

Example 44

Preparation of Ticagrelor (TCG)

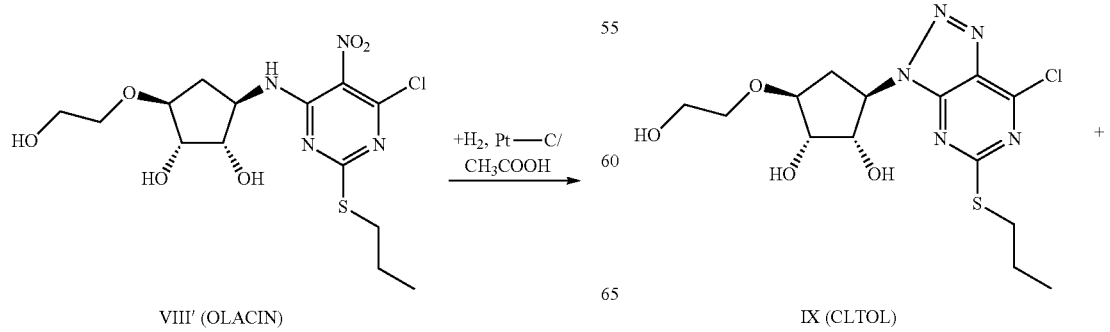

VIII' (OLACIN)

IX (CLTOL)

89

-continued

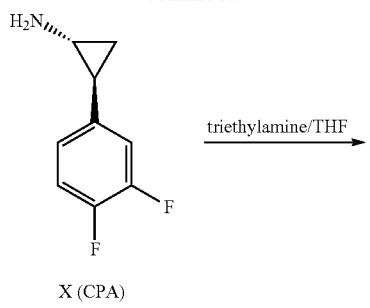

X (CPA)

triethylamine/THF →

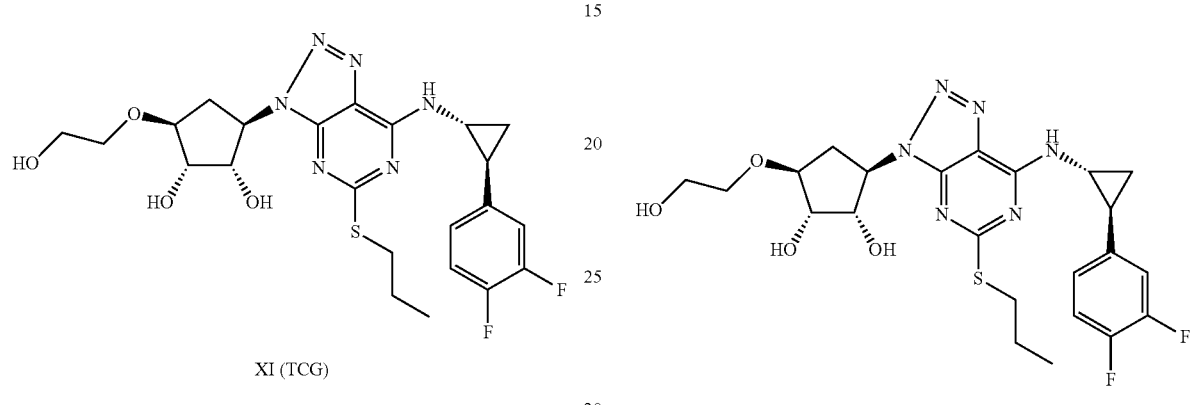

XI (TCG)

To a stirring solution of (1S,2S,3R,5S)-3-(7-(((1R,2S)-2-(3,4-difluorophenyl)cyclopropyl)amino)-5-(propylthio)-3H-[1,2,3]triazolo[4,5-d]pyrimidin-3-yl)-5-(2-hydroxyethoxy)cyclopentane-1,2-diol (CLTOL; 1.56 g, 4 mmol) in tetrahydrofuran (20 mL) at 20° C. was added a mixture of (1R,2S)-2-(3,4-difluorophenyl)cyclopropanamine (CPA; 0.68 g, 4 mmol) and triethylamine (0.70 mL, 5 mmol). After 2 h, the mixture was diluted with methyl tert-butyl ether (30 mL) and washed with 1% aqueous acetic acid (100 mL), water (75 mL) and evaporated under reduced pressure. The residue was triturated under n-hexane (20 mL) and filtered to give ticagrelor (2.00 g, 96% yield): $^{19}$F NMR (CDCl$_3$, 470.5 MHz) δ −142.4 (m, 1F), −139.0 (m, 1F); MS (ESI) m/z: 523 [MH]$^+$.

Example 45

Preparation of Ticagrelor (TCG)

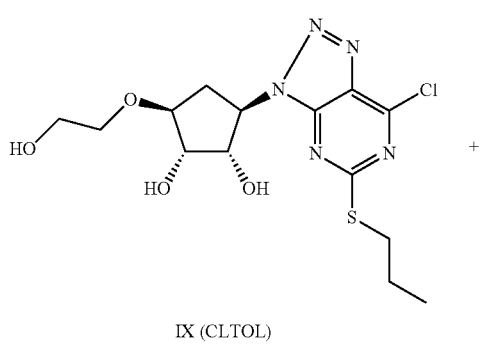

IX (CLTOL)

+

90

-continued

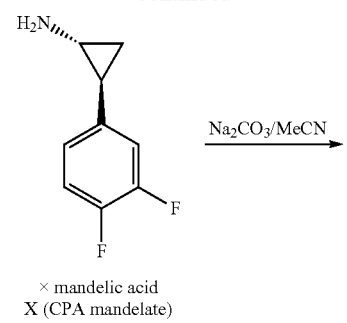

× mandelic acid
X (CPA mandelate)

Na$_2$CO$_3$/MeCN →

XI (TCG)

To a stirring suspension of (1R,2S)-2-(3,4-difluorophenyl)cyclopropanamonium mandelate (0.33 g, 1.03 mmol) and sodium carbonate (0.27 g, 2.5 mmol) in acetonitrile (12 mL) at 20° C. was added (1S,2S,3R,5S)-3-(7-(((1R,2S)-2-(3,4-difluorophenyl)cyclopropyl)amino)-5-(propylthio)-3H-[1,2,3]triazolo[4,5-d]pyrimidin-3-yl)-5-(2-hydroxyethoxy)cyclopentane-1,2-diol (CLTOL; 0.39 g, 1 mmol). The mixture was stirred for 20 h, diluted with water (50 mL) and extracted with ethyl acetate (60 mL). The extract was washed with water (50 mL), 0.1M aqueous acetic acid (50 mL), again water (50 mL) and evaporated under reduced pressure to give ticagrelor (0.50 g, 93% yield): $^{19}$F NMR (CDCl$_3$, 470.5 MHz) δ −142.5 (m, 1F), −139.0 (m, 1F); MS (ESI) m/z: 523 [MH]$^+$.

Example 46

Preparation of Ticagrelor (TCG)

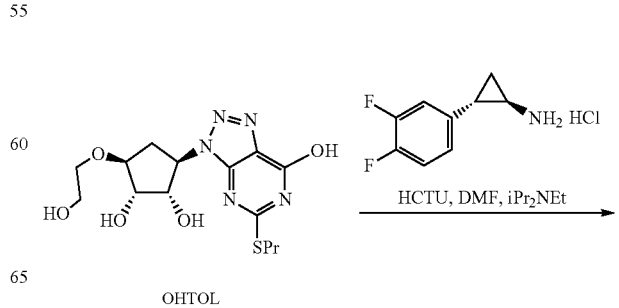

OHTOL

HCTU, DMF, iPr$_2$NEt →

-continued

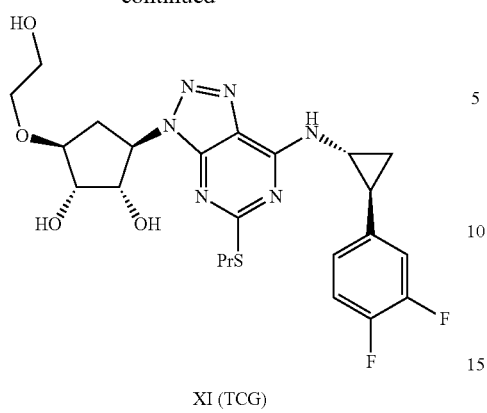

XI (TCG)

To a solution of OHTOL (0.74 g), O-(6-chlorobenzotriazol-1-yl)-N,N,N',N'-tetramethyluronium hexafluorophosphate (HCTU, 0.99 g) in dry DMF (2.5 mL) under nitrogen atmosphere was added N,N-diisopropylethylamine at 25° C., stirred for 15 min and (1R,2S)-2-(3,4-difluorophenyl)cyclopropanamine hydrochloride (0.50 g) was added. The resulting solution was stirred at 25° C. for 16 hours and the solvent was removed under reduced pressure. The product was purified by chromatography (silica gel; ethyl acetate) to give ticagrelor (0.9 g).

The invention claimed is:

1. A process for the preparation of a compound of formula XI or a salt thereof

XI

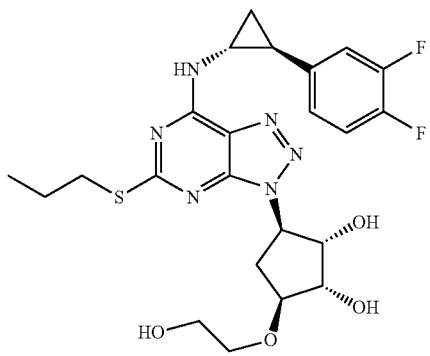

comprising the steps of:
(i) contacting a compound of formula VI or a salt thereof

VI

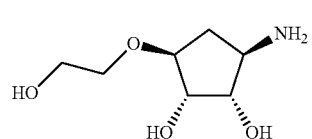

with a compound of formula VII or VII'

VII

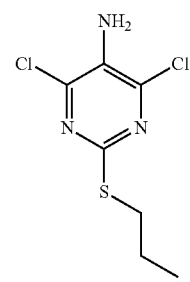

VII'

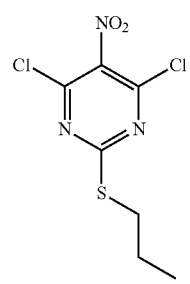

to obtain a compound of formula VIII or VIII', respectively

VIII

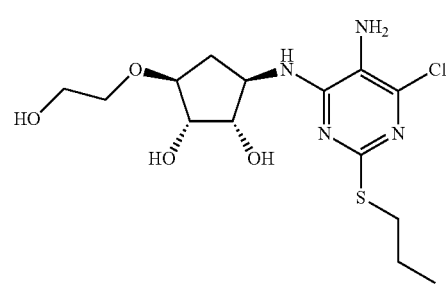

VIII'

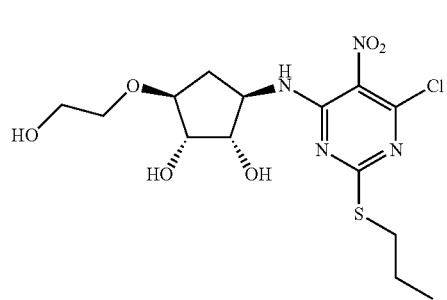

(ii) optionally, if a compound of formula VIII' is obtained, reducing the compound of formula VIII' to a compound of formula VIII, (iii) converting a compound of formula VIII by nitrosation to a compound of formula IX or a compound of formula IX'

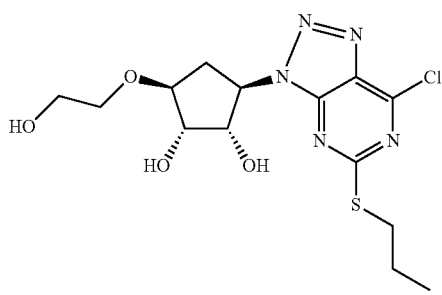
IX

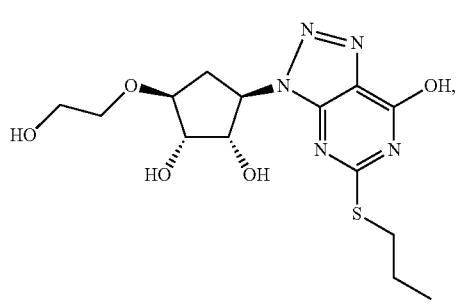
IX' and
(iv) coupling the compound of formula IX or IX' with a compound of formula X

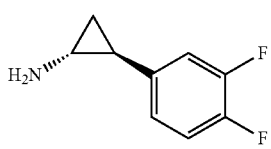
X or a salt thereof in a presence of a base to provide a compound of formula XI or a salt thereof
wherein the compound of formula VI or a salt thereof is prepared by a process comprising the steps of either
(0-1) providing a compound of formula III or a salt thereof

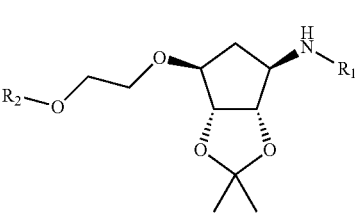
III wherein $R_1$ is Boc, Cbz, TFA, Tr, TCA, CHO, Ac, Bz, Fmoc, $C_4$-$C_5$-tert-alkyl, or mono, di- or triphenyl substituted methyl, and $R_2$ is Bn, t-Bu, TBDMS, MOM, Tr, Ac or Bz;
(0-2) directly converting a compound of formula III to a compound of formula VI, and
(0-3) optionally converting a compound of formula VI to a salt thereof;
or (0-1') providing a compound of formula III or a salt thereof

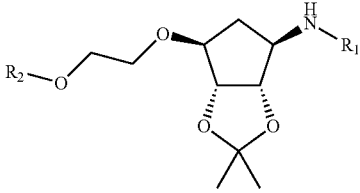
III wherein $R_1$ and $R_2$ is as defined above,
(0-2') converting a compound of formula III to a compound of formula IV

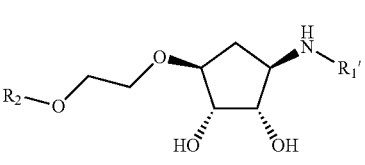
IV wherein $R_1'$ is hydrogen, Boc, Cbz, TFA, Tr, TCA, CHO, Ac, Bz, Fmoc, $C_4$-$C_5$-tert-alkyl, or mono, di- or triphenyl substituted methyl and $R_2$ is as defined above, and
(0-3') converting a compound of formula IV to a compound of formula VI,
(0-4') optionally converting a compound of formula VI to a salt thereof;
or
(0-1") providing a compound of formula III or a salt thereof

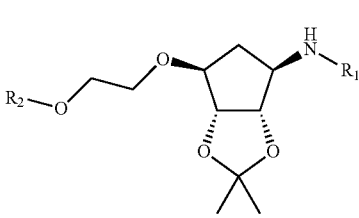
III wherein $R_1$ and $R_2$ is as defined above,
(0-2") converting a compound of formula III to a compound of formula V

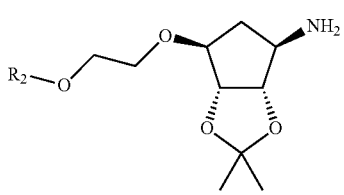
V wherein $R_2$ is as defined above, and
(0-3") converting a compound of formula V to a compound of formula VI,
(0-4") optionally converting a compound of formula VI to a salt thereof;
or (0-1''') providing a compound of formula J

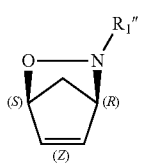

J wherein $R_1''$ is Boc, Cbz, TFA, TCA, CHO, Ac, Bz, Fmoc, (0-2''') reacting the compound of formula J with the compound of formula Z

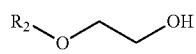

Z wherein $R_2$ is Bn, t-Bu, TBDMS, MOM, Tr, Ac or Bz, to yield a compound of formula K

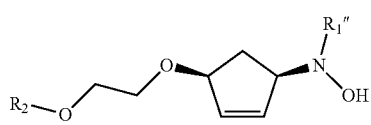

K wherein $R_1''$ and $R_2$ are as defined above, (0-3''') oxidising the compound of formula K to obtain a compound of formula L

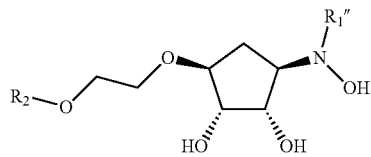

L wherein $R_1''$ and $R_2$ are as defined above, (0-4''') converting the compound of formula L to the compound of formula VI, and (0-5''') optionally converting a compound of formula VI to a salt thereof.

2. The process according to claim 1, wherein step (i), optional step (ii) and step (iii) are carried out in one pot.

3. The process according to claim 1, wherein in step (iii) the compound of formula IX' is obtained and step (iv) is conducted in a presence of a coupling reagent.

4. The process according to claim 1, wherein the compound of formula III or a salt thereof is prepared by comprising the steps of:

(i) providing a compound of formula I

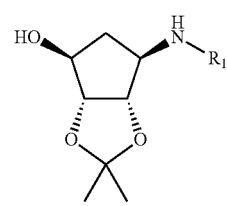

I wherein $R_1$ is Boc, Cbz, TFA, Tr, TCA, CHO, Ac, Bz, Fmoc, $C_4$-$C_5$-tert-alkyl, or mono, di- or triphenyl substituted methyl, (ii) reacting the compound of formula I with a compound of formula II

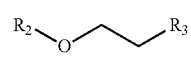

II wherein $R_2$ is Bn, t-Bu, TBDMS, MOM, Tr, Ac or Bz, and $R_3$ is TsO, MsO, Br or Cl to yield a compound of formula III, and (iii) optionally converting the compound of formula III to a salt thereof.

5. The process according to claim 4, wherein the compound of formula I is prepared by comprising the steps of:

(iv) providing a compound of formula A

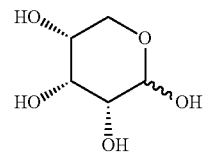

A (v) contacting the compound of formula A with acetone or acetone ketals and methanol in acidic medium to obtain a compound of formula B

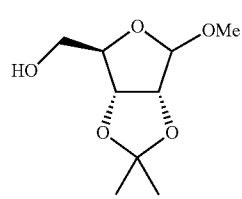

B (vi) contacting the compound of formula B with chlorides or anhydrides of sulfonic acids to give a compound of formula C

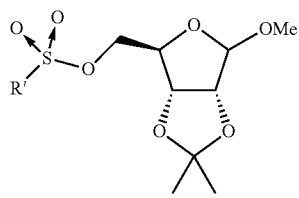

C wherein R' is unsubstituted or fluoro substituted $C_1$-$C_4$-alkyl, unsubstituted or methyl, methoxy, bromo, nitro substituted phenyl, or 10-camphoryl;

(vii) optionally purifying the compound of formula C by recrystallization, (viii) treating the compound of formula C with metal or quaternary ammonium halides thereby converting it into a compound of formula D

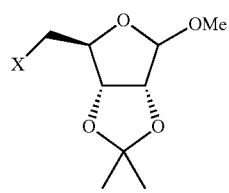

D wherein X is iodo, bromo or chloro, (ix) reducing the compound of formula D with activated zinc, optionally in the presence of copper to give the compound of formula E

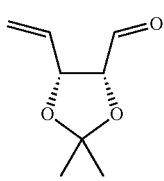

E (x) treating the compound of formula E with N-monosubstituted hydroxylamines to give a compound of formula F

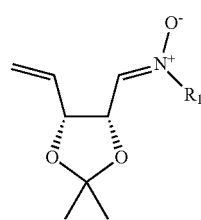

F wherein $R_1$ is $C_4$-$C_5$-tert-alkyl or mono, di- or triphenyl substituted methyl, (xi) thermally transforming the obtained compound of formula F to yield a compound of formula G

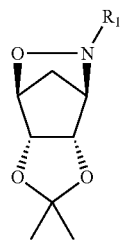

G wherein $R_1$ is as defined above, and either (xii) reducing the compound of formula G to yield the compound of formula I, wherein $R_1$ is $C_4$-$C_5$-tert-alkyl or mono, di- or triphenyl substituted methyl, or (xiii) reducing the compound of formula G to yield the compound of formula H

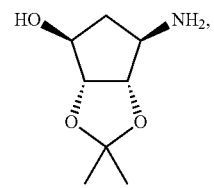

H and

N-substituting the compound of formula H to yield the compound of formula I.

6. The process according to claim 1, wherein in step (0-4''') both de-protection of groups $R_1$'' and $R_2$ and reduction of the hydroxylamine moiety are performed simultaneously in the same reaction mixture to obtain the compound of formula VI.

7. A process for the preparation of a pharmaceutical composition comprising a compound of formula XI or a pharmaceutically acceptable salt thereof

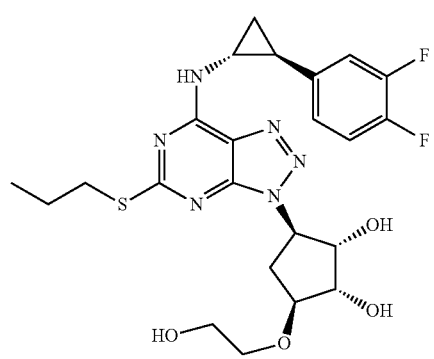

XI comprising the steps of:

(i) preparing a compound of formula XI or a salt thereof according to claim 1, optionally converting the salt into a pharmaceutically acceptable salt, and (ii) mixing the compound of formula XI or a pharmaceutically acceptable salt thereof with a pharmaceutically acceptable carrier and/or excipient.

* * * * *